(12) United States Patent
Lopato et al.

(10) Patent No.: US 9,499,831 B2
(45) Date of Patent: Nov. 22, 2016

(54) PLANT TRANSCRIPTION FACTORS, PROMOTERS AND USES THEREOF

(71) Applicants: Australian Centre for Plant Functional Genomics, South Australia (AU); E I DU PONT DE NEMOURS AND COMPANY, Wilmington, DE (US); PIONEER HI BRED INTERNATIONAL INC, Johnston, IA (US)

(72) Inventors: Sergiy Lopato, Morphett Valve (AU); Sobhana Sivasankar, Adel, IA (US); Maria Hrmova, South Australia (AU); Peter Langridge, Teringie (AU); Omid Eini Gandomani, Kensington (AU); Scott V Tingey, Rockdale, TX (US)

(73) Assignees: PIONEER HI-BRED INTERNATIONAL, INC., Johnston, IA (US); E. I. Du Pont De Nemours & Company, Wilmington, DE (US)

( * ) Notice: Subject to any disclaimer, the term of this patent is extended or adjusted under 35 U.S.C. 154(b) by 97 days.

(21) Appl. No.: 14/372,968

(22) PCT Filed: Jan. 17, 2013

(86) PCT No.: PCT/US2013/021939
§ 371 (c)(1),
(2) Date: Jul. 17, 2014

(87) PCT Pub. No.: WO2013/109754
PCT Pub. Date: Jul. 25, 2013

(65) Prior Publication Data
US 2015/0197768 A1    Jul. 16, 2015

Related U.S. Application Data

(60) Provisional application No. 61/587,342, filed on Jan. 17, 2012.

(51) Int. Cl.
*A01H 5/00*      (2006.01)
*C07K 14/415*    (2006.01)
*C12N 15/82*     (2006.01)
*A01H 1/00*      (2006.01)
*C07H 21/04*     (2006.01)
*C12N 15/00*     (2006.01)

(52) U.S. Cl.
CPC ......... *C12N 15/8273* (2013.01); *C07K 14/415* (2013.01); *C12N 15/8237* (2013.01); *C12N 15/8261* (2013.01); *C12N 15/8271* (2013.01)

(58) Field of Classification Search
None
See application file for complete search history.

(56) References Cited

U.S. PATENT DOCUMENTS 7,244,879 B2 *  7/2007  Christensen ....... C12N 15/8273
                                                         435/320.1
2009/0241208 A1  9/2009  Christensen et al.

FOREIGN PATENT DOCUMENTS

WO    2010039750 A2    4/2010
WO    2010064934 A1    4/2010

OTHER PUBLICATIONS

Zhang, "Isolation and characterization of a novel EAR-motif-containing gene GmERF4 from Soybean (Glycine max L.)," Mol Biol Rep, 2010, vol. 37: 809-818.
Kagale, "EAR motif-mediated transcriptional repression in plants" Epigenetics, 2011, vol. 6 (2): 141.

* cited by examiner

*Primary Examiner* — Phuong Bui
(74) *Attorney, Agent, or Firm* — Pioneer Hi-Bred Intl. Inc.

(57) ABSTRACT

Polynucleotide molecules encoding transcription factors, promoter elements, binding partners and methods of use in increasing drought tolerance, yield, and abiotic stress tolerance are disclosed. ERF transcription factors and Cor410b promoter sequences are disclosed.

4 Claims, 14 Drawing Sheets

Figure 1:
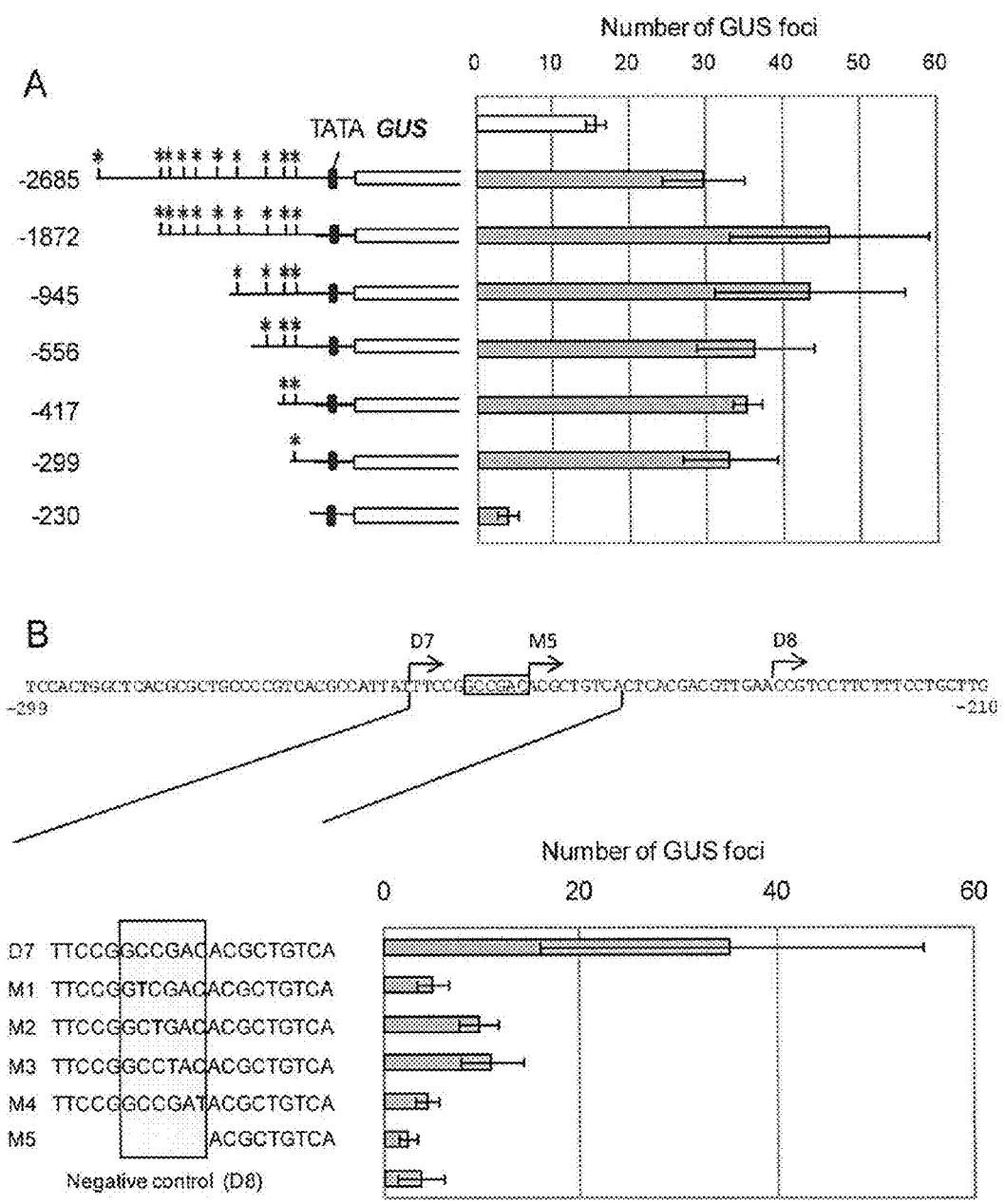

```
         D1>(-2685)
-2685    ATGGATGT GGATTTTTGA ACGCCTGAAC CTGTCCGGCT TAATTTGATT ATCCACATTG AATGGTTAAA ATGTTCAAAT GGTCTGATCA GGACCCAAGA
-2585    TCATAATCTC TTCTTTCCCC TCATGCTAAG GTGGCTACGG CAAAGTACTC CTCCCCTCGA AGCTCCACCG GCCAACCAGT GGATTCTCCT CTCCTCCATC
-2485    TGCCGCTCTA GCGGCTGGTG ACGGAGGAG AACCCCGGTG CCTTGACTCC GGCTAATAGT CTAGGTTAGC ATTTTTTCCT TGCACGGGTG ACGCTCAGAT
-2385    GGATGACAAC GCTTCATCTT CAAGTTGGTC TTCCATTGTT CGTTCCTCCT CGAAATCGCT CGTCAGGGTG AAGTCGCCGA AGCTCTGGCA TAGATTACTG
-2285    CAGTCTCTTC GGGCACAAG GTTAGAATTT CTCGCCAAGT GTGTGCGATG GCGAGATCG GTGTGAGGTG CTTCAAATCA ATTTAAGGGT TCAACGGCGC
-2185    TGACCACGGC TCCCTGACGC TGGTTCTTAG GGGCACGTTC ATGAAGACTT CGTGGCTCAT CGACAAGTTT AGGCGGACTC CATTATCAGG GCGGCGATAC
-2085    CGATGCCTCA TCGGCTCTTC TGACGGCGAC AGTGGTCGTT CGGTGTCCA AAGACCTTGA TCTAATTTTT ATTATGTTTA GGGTACTTTG TAATTCCAAT
-1985    GAACTTTTAT TCGATATCTG GGTATTAAAA AAATATCTAA ACCTTTTTT AACATAGTAC AATTGGAGAT GCTCACATGC ACTCACCCCA TAAACACATG
         D2>(-1872)
-1885    CACGCACTTT CTATACCTAT GAGAGCCTTC AAGAACACTGA GCCGGATAA AATCTTAAAA TTGACGAAAT CGTCATAAAC ACCTTTATAG TCAACGAAAA
-1785    CATCTCCTCA CACCGAATGC AGTCACTAAA GTACACATCG GCGCATCTGG GTACACATCG TGACGCACATA AAAATCACG ACCACCGGTG TCCGTGCGGT CATGAACTCC GGTATCCACC
-1685    GCAAGAAATC AAAACATCTC GGCCCACGTA GTCGGAAAT CGTACGTGTG GGTGGGTGGG TGCCCGGGG AGCGAGCTAG ATGCGCTGAA GGCACAGTCT CGCCCTGTGC
-1585    GATTCCGGGT CGGGGGCAG CAGCCATCGA GCGATCGCCT CCGGTCCCGC TGAACTGAAT CGATCCATGA GTCATGTCTG CCCGTGTCTA CGACCCATGT
-1485    AGCCATGTGG CGGGGGCAG GAGCCCTTGC TATACACTGT TCACCGATT GCCAGGACGA GGAAGGAGGC GTTTTGCATC TCCGTCGCG TCGATGCC GAGGGCCGAT
-1385    GCAGAGGACG GCGAGCTGGT TATACACTGA TCACGGATTT GCCAGGACA GGAAGGAGGC GTTTTGCATC TCCGTCGCG GCGAATCCCAC TTTCCACCGC
-1285    AGTACGTCCG GGCATCCCGT GCACCGAAAG TAGCCAATAA TGACTCCAGC TAGTCTCGTA CGCTCGATGG CCGGTGAGTT TTCTTCCCAG
-1185    TGGCTGTCAC GAATGACGG TGAAAAGAA ACCAAGAGTC CCGGCATTTG CCCACGAAAG CGCTCATCAA AGCGAGAAG CAGAAACAAA AGAACGGCCA
-1085    
         D3>(-945)
-985     GCCCGATCGA TCTGATTAGA AGCCCTGGAC ATCGGGGCGG ATCGGGGTGG AGTTTAATC AGTCCGCTCA CCCCGCCGA CTCCACTCGA GCAAGGAAAC CCCACCCGCT
-885     TTGCTAGGTT CGGCACGACG GGGCCGGTGAG CGGATAGTCG TTTCGACCCC ACATGTCAAC CCACGACTC TTATCTTCGT CGGCTACCGG TGATTGAGCA GTCCTAGTCA
-785     TGTGCTATCA CTCCCGCGAG GTGCACCCCT TGATTTAGTA ACGAAATCCA ATCAATGTTA ATGCCACACA ACCGGTAAAA TAAACCCCGG CCAAACATTT GTGGACAAGA
-685     TCGATGTTAA TGCTTCCTCA TCCCTCAAAAA AAAAAAAGA
         D4>(-556)
-585     TGGCTCACGC CACTGTTTCA AAAATCGATG GATCACTTAA TCAATCGGTC GAATTATCTC AACCTAAAGT ATTGCCCGGAG AGCGACGGGC GTGGACAAGC
         D5>(-417)
-485     GTCCCGTCGG CAGGGGATGC GGAGGAGAGG CCACGGAGGG AGGCACCCCA CCCGGACCATTC GCACCGGCGC ACGCCTCGGT GAGGTACT ACCCACCACT
         D6>(-299)
-385     CCACATGGCG CCCGGCTAC TCTCCGATG CCGTGCGATGG CGGCGTCCGCC ACGTCGGACT GACCGCCCCA CGACATGCGT CGGGGCCCA CTGGCTCACG
         D7>(-263)                         D8>(-230)
-285     CCGTGCCCCG TCACGCCATT ATTTCCCCGCA ACGGCTGT CACTCACGAC GTTGACCGT CCTTCTTTCC TGCTTGTATT GTCCTACGT ACAGGCTAC
-185     AGGGACAGA TGTACACCTC TCGCCAGCGG CTCCGGATCG ACCTCCTTGA CAGCGGCTAT ATAAGGAAGC CTCTTGCCA GGACACCTTC ATCAGTCACA
-85      AAGCCACAAG CCAAGAACCA ATACTTGATC TGTTGTTTCC GGAAGACCTT TTAGCTCCC CGATCGATCT TTAGCTGCAC CGATCGATCT CGATCATG
```

FIGURE 10

A

| | | | |
|---|---|---|---|
| AtERF8 | 33 | -------GVRKRPWGRYAAEIRDPVKKTRVWLGTFDTAQQAARAYDAAARDFRGVKAKTNF | 86 |
| GmERF4 | 28 | -------GVRKRPSGRYAAEIRDPGKESRVWLSTFDTAEEARARAYDAAAREFRSPKAFTNF | 81 |
| NsERF3 | 29 | -------GVRKRPWGRYAAEIRDPGKKSRVWLSTFDTAEEAARAYDTAAREFRGPRAKTNF | 83 |
| AtERF9 | 35 | -------GVRKRPWGRYAAEIRDPGKKTRVWLSTFDTAEEAARAYDIAAREFRSSKAFTNF | 88 |
| AtERF4 | 27 | -------GVRKRPWGRYAAEIRDPGKNTRVWLGTFDTAEEAARAYDTAARDFRGAKAKTNF | 80 |
| AtERF11 | 22 | -------GVRKRPWGRYAAEIRDPFKKSRVWLGTFDTPEEAARAIDKEAIRFRGAKAKTNF | 75 |
| AtERF12 | 14 | -------GVRKRPWGRYAAEIRDPWKKTRVWLGTFDTPEEAALAYDGAARFLRGIKAKTNF | 67 |
| TaERF4b | 24 | -------GVRKRPSGRYAAEIRDPAKKTVWLGTFDCAEDAARAYDSAARSLRGFTARTNF | 77 |
| TaERF4a | 21 | -------GVRKRPSGRYAAEIRDPAKKTIWLGTFDCAEDAARAYDAAARSLRGPTARTNF | 74 |
| HvERF4 | 21 | -------GVRKRPSGPYAAEIRDPAFKTIWLGTFDSAEAAARAYDAAARNLRGAAARTNF | 74 |
| AtERF7 | 29 | -------GVRKRPWGRFAAEIRDPLKKSRVWLGTFDSAVDAARAIDTAAPNLRGPKAFTNF | 82 |
| AtERF3 | 30 | -------GVRKRPWGRFAAEIRDPWKASVWLGTFDSAEDAARAYISAARSILRGPFAKTNF | 83 |
| AtERF10 | 49 | KEVRYRGVRRRPSGRYAAEIRDPVKKFRVWLGSFWTGEEAARAYDSAAIRFRGSKATTNF | 108 |

B

| | | |
|---|---|---|
| AtERF8 | LDLNLRLAPPA------ | 184 |
| GmERF4 | FDLNLNKPPPH------ | 219 |
| NsERF3 | IDLDLNLAPPTNF---- | 227 |
| AtERF9 | LNLDLNLAPPV------ | 197 |
| AtERF4 | LDLDLNLRPPS------ | 219 |
| AtERF11 | LDLNLNFPPPNR----- | 166 |
| AtERF12 | LAIDLNFPPPLWG---- | 189 |
| TaERF4b | LPFDLNMPPPQLGALDA | 181 |
| TaERF4a | LPFDLNFPPPQDGALDA | 177 |
| HvERF4 | LPFDLNLPPPA------ | 183 |
| AtERF7 | FQFDLNFPPLDGV--DL | 229 |
| AtERF3 | FQFDLNFPPLDCV---D | 210 |
| AtERF10 | FDLDLNASP-------- | 245 |

FIGURE 14

SEQUENCE LISTING

```
<160> NUMBER OF SEQ ID NOS: 90

<210> SEQ ID NO 1
<211> LENGTH: 195
<212> TYPE: PRT
<213> ORGANISM: Triticum aestivum

<400> SEQUENCE: 1

Met Arg Arg Ala Arg Pro Pro Gln Pro Gln Pro Gln Pro Ser Pro Glu
1               5                   10                  15

Ile Arg Tyr Arg Gly Val Arg Lys Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Cys Ala Glu Asp Ala Ala Arg Ala Tyr Asp Ser Ala Ala Arg Ser
    50                  55                  60

Leu Arg Gly Pro Thr Ala Arg Thr Asn Phe Pro Pro Ser Ser Ala Thr
65                  70                  75                  80

Gln Pro Pro Pro Arg Pro Pro Pro Pro Ala Ala Ala Ala Ala Ala Thr
                85                  90                  95

Ala Thr Thr Ser Gln Ser Ser Thr Val Glu Ser Trp Ser Gly Gly Gly
            100                 105                 110

Pro Arg Ala Pro Ala Arg Ala Arg Ser Ala Ala Arg Ala Gly Thr Ala
        115                 120                 125

Glu Glu Gly Glu Glu Asp Cys Arg Ser Tyr Cys Gly Ser Ser Ser Ser
    130                 135                 140

Val Leu Leu Cys Glu Asp Gly Asp Ala Ala Ala Ser Arg Thr Pro
145                 150                 155                 160

Leu Pro Phe Asp Leu Asn Met Pro Pro Gln Asp Gly Ala Leu Asp
                165                 170                 175

Ala Ala Ala Ala Glu Ala Asp Gln Met Thr Cys Arg Tyr Asp Thr Leu
            180                 185                 190

Leu Arg Leu
        195

<210> SEQ ID NO 2
```

```
<211> LENGTH: 989
<212> TYPE: DNA
<213> ORGANISM: Triticum aestivum

<400> SEQUENCE: 2
gcacgcacgc cactgtgacc aaaccctagg ccggccgcga tgcgcagggc gaggccgccg      60
cagccccagc cgcagccgtc gccggagatc cggtaccgcg gcgtgcggaa gcgcccctcg     120
ggccgctacg ccgccgagat ccgggacccg gccaagaaga cgccgatctg gctgggcacc     180
ttcgactgcg ccgaggacgc cgcccgcgca tacgactccg ccgcccgatc cctccgcggg     240
cccaccgccc gcaccaactt cccgccctcc tccgccacgc agccgccgcc gcgccctccc     300
cctcccccg cggcggccgc cgcgaccgcc acgaccagcc agagcagcac cgtcgagtcc      360
tggagcggcg gcgggccccg cgcccccgcc agggccgca gcgccgcccg agcgggcacg     420
gccgaggaag gggaggagga ctgccgcagc tactgcggct cctcctcctc cgtcctcctc     480
tgcgaggatg gggacgacgc ggccgcctcc cgcaccccgc tgcccttcga tctgaacatg     540
ccgcccccac aggacggggc ccttgacgcc gcggccgccg aggctgatca gatgacctgc     600
cgctacgaca cgctgctccg cctctagctc gacaacgacg acgagaatag caaggattcg     660
tgggagggg gactggggaa aggaacgaga aaagcgcttg ccccgctcc gctttgcttt      720
ggtccgtctt ccgatgatct tgtggtgttc tcttttgcta gaaatggaga attcttgcca     780
cttttttct tactttcttt ccttcttctt ttttcttct taccactttg atttgatatg     840
tgaataattc agtcatgtaa gctgcgagca aggaaatttt agcttttcct tatctttctc     900
tgtggtattt caagagtgat tgctgctgt tgttgtttca ttaattggaa aagggtaatc     960
gaaggaatga agaaaaagta tttgacgaa                                      989

<210> SEQ ID NO 3
<211> LENGTH: 268
<212> TYPE: PRT
<213> ORGANISM: tricticum durum

<400> SEQUENCE: 3

Met Glu Asp Glu Arg Ser Thr Gln Ser Tyr Gln Gly Gly Glu Ala Ala
1               5                   10                  15

Glu Gln Val Glu Val Thr Asp Arg Gly Leu Leu Gly Asn Leu Leu Gly
            20                  25                  30

Lys Lys Lys Ala Glu Glu Asp Lys Glu Lys Glu Glu Glu Leu Val
        35                  40                  45

Thr Gly Met Glu Lys Val Ser Val Glu Glu Pro Glu Val Lys Lys Glu
    50                  55                  60

Glu His Val Asp Gly Glu Lys Lys Glu Thr Leu Phe Ser Lys Leu His
65                  70                  75                  80

Arg Ser Ser Ser Ser Ser Ser Ser Asp Glu Glu Glu Glu
                85                  90                  95

Val Ile Asp Asp Asn Gly Glu Val Ile Lys Arg Lys Lys Lys Gly
            100                 105                 110

Leu Lys Glu Lys Leu Gln Glu Lys Leu Pro Gly His Lys Asp Thr Glu
        115                 120                 125

Gly Glu His Val Thr Gly Leu Pro Ala Pro Ala Pro Ala Ser Val
    130                 135                 140

Gln Thr His His Asp Thr Asp Val Val Glu Lys Ile Asp Gly Asp
145                 150                 155                 160

Val Lys Thr Glu Ala Thr Pro Ala Val Pro Glu Glu Glu Lys Lys Gly
```

```
                165                 170                 175
Phe Leu Glu Lys Ile Lys Glu Lys Leu Pro Gly Gly His Lys Lys Pro
            180                 185                 190

Glu Asp Ala Ala Val Pro Val Thr His Ala Ala Pro Ala Pro Val
            195                 200                 205

Thr His Ala Ala Pro Ala Pro Val His Ala Pro Ala Pro Ala Ala Glu
            210                 215                 220

Glu Val Ser Ser Pro Asp Ala Lys Glu Lys Gly Leu Leu Gly Lys
225                 230                 235                 240

Ile Met Asp Lys Leu Pro Gly Tyr His Lys Thr Gly Glu Glu Asp Lys
                245                 250                 255

Ala Ala Ala Ala Thr Gly Glu His Lys Pro Ser Ala
            260                 265
```

<210> SEQ ID NO 4
<211> LENGTH: 2688
<212> TYPE: DNA
<213> ORGANISM: Tricticum durum

<400> SEQUENCE: 4

| | | | | | |
|---|---|---|---|---|---|
| gtcggtttgt | ggatttttga | acgcctgaac | ctgtccggct | taatttgatt | atccacattg | 60 |
| aatggttaaa | atgttcaaat | ggtctgatca | ggacccaaga | tcataatctc | ttctttcccc | 120 |
| tcatgctaag | gtggctacgg | caaagtactc | ctccctcga | agctccaccg | gccaaccagt | 180 |
| ggattctcct | ctcctccatc | tgccgctcta | gcggctggtg | acgggaggag | aaccccggtg | 240 |
| ccttgactcc | ggctaatagt | ctaggttagc | atttttcct | tgcacgggtg | acgctcagat | 300 |
| ggatgacaac | gcttcatctt | caagttggtc | ttccattgtt | cgttcctcct | cgaaatcgct | 360 |
| cgtcagggtg | aagtcgccga | agctctggca | tagattactg | cagtctcttc | gggcgacaag | 420 |
| gttagaattt | ctcgccaagt | gtgtgcgatg | gcgagatccg | gtgtgaggtg | cttcaaatca | 480 |
| atttaagggt | tcaacggcgc | tgaccacggc | tccctgacgc | tggttcttag | ggcacgttc | 540 |
| atgaagactt | cgtggctcat | cgacaagttt | aggcggactc | cattatcagg | gcggcgatac | 600 |
| cgatgcctca | tcggctcttc | tgacggcgac | agtggtcgtt | cggtggtcca | aagaccttga | 660 |
| tctaattttt | attatgttta | gggtactttg | taattccaat | gaacttttat | tcgatatctg | 720 |
| ggtattaaaa | aaatatctaa | accttttttt | aacatagtac | aattggagat | gctcacatgc | 780 |
| actcacccca | taaacacatg | cacgcacttt | ctacacctat | gagagccttc | aagacactga | 840 |
| gccgacataa | aatcttaaaa | ttgacgaaat | cgtcataaac | accttttatag | tcaacgaaaa | 900 |
| catctcctca | caccgaatgc | acatagtcgg | agtcactaaa | aataaattca | aaaaatcacg | 960 |
| accaccggtg | tcaagtataa | catgaactcc | ggtatccacc | gcaagaaatc | aaaacatctc | 1020 |
| gcgcatctgg | gtacacatcg | tgacgtccac | cgtcgacata | gccccctggg | tgcgtgcggt | 1080 |
| cgcgcagtta | acgacgcagc | gattccgggt | ggcccacgta | gtcggcaaat | cgtacgtgtg | 1140 |
| ggtgggtggg | tgcgccgggg | agcgagctag | atgcgctgaa | gcacagtct | cgccctgtgc | 1200 |
| agccatgtgg | cgggggcag | cagccatcga | gcgatcgcct | cgcgtgccgc | tgaactgaat | 1260 |
| cgatccatga | gtcatgtctg | ccgcgtcgta | cgacccatgt | gcagaggacg | gagcccttgc | 1320 |
| cactgcccgc | ccaggcagga | tccgatgctg | ctgactagtt | tatccgccga | tccgttcgcg | 1380 |
| tcccgacgac | gagggccgat | agtacgtccg | gcgagctggt | tatacactga | tcacggattt | 1440 |
| gccaggacca | ggaaggaggc | gttttgcatc | gcgatcccac | ggcgcaaac | tttccaccgc | 1500 |
| tggctgtcac | ggcatcccgt | gcaccgaaag | tagccaataa | tgactccagc | tagtctcgta | 1560 |

-continued

```
cggtcggtgg ccgggcttgg ccggtgagtt ttcttcccag gaatggacgg tgaaaagaa      1620 accaaaaggc cgacacgcca ccggcatttg cccacgaaag cgctcatcaa agcgagaaag     1680
cagaaacaaa agaacggcca gcccgatcga tctgattaga agccctggac atcggggtgg    1740
cagtttaatc agtccgctca ccccgccgga ctccactcga gcaaggaaac cccacccgct    1800
ttgctaggtt cggcacgacg ggccggtgag cggatagtcg tttcgacccc acatgtcaac    1860
atcgggctct ctttctagag ccctctcgtc gtcctagtca tgtgctatca ctcccccgac    1920
gtgcacccct tgatttagta acgaaatcca ccacgaactc ttatcttcgt ccgctaccgg    1980
tgattgagca tccggaagaa tcgatgttaa tgcttcctca tcctcaaaaa aaaaaaagaa    2040
atcaatgtta atgccacaca accgctaaaa taaaccccgg ccaaacattt gtggacaaaa    2100
tggctcacgc cactgtttca aaaatcgatc gatcacttaa tcaatcggtc gaattatctc    2160
aacctaaagt attgccggag agcgacgggc gtggacaagc gtcccgtcgg cagcggatgc    2220
ggaggagagg ccacggaggg aggcacccca ccgaccattc gcaccgggcc acgcctcggt    2280
gagcgtaact acccaccact ccacatggcg cccgccgacc tctcccgatg ccgtcgatgg    2340
cgcgtccgcc acgtcggact gaccgcccca cgacatgcgt cggggctcca ctggctcacg    2400
cgctgccccg tcacgccatt atttccggcc gacacgctgt cactcacgac gttgaaccgt    2460
ccttctttcc tgcttgtatt gtcctcacgt acagcgctac agggcacaga tgtacacctc    2520
tcgccagcgg ctccggatcg acctccttga cagcggctat ataaggaagc tcttggcca    2580 ggacaccttc atcagtcaca aagccacaag ccaagaacca atacttgatc tgttgtttcc    2640
tttagctccc ggaagacctt ttagctgcac cgatcgatct cgatcatg               2688
```

<210> SEQ ID NO 5
<211> LENGTH: 199
<212> TYPE: PRT
<213> ORGANISM: Triticum aestivum

<400> SEQUENCE: 5

```
Met Arg Lys Ala Arg Pro Pro Gln Pro Gln Pro Ser Gln Gln
1               5                   10                  15

Ser Pro Glu Ile Arg Tyr Arg Gly Val Arg Lys Arg Pro Ser Gly Arg
                20                  25                  30

Tyr Ala Ala Glu Ile Arg Asp Pro Ala Lys Lys Thr Pro Ile Trp Leu
            35                  40                  45

Gly Thr Phe Asp Cys Ala Glu Asp Ala Ala Arg Ala Tyr Asp Ser Ala
        50                  55                  60

Ala Arg Ser Leu Arg Gly Pro Thr Ala Arg Thr Asn Phe Pro Pro Ser
65                  70                  75                  80

Ser Ala Thr Gln Pro Pro Arg Pro Pro Pro Ala Ala Ala
                85                  90                  95

Ala Ala Ala Thr Val Thr Ser Ser His Ser Ser Thr Val Glu Ser Trp
            100                 105                 110

Ser Gly Gly Gly Pro Arg Ala Pro Ala Arg Ala Arg Ser Ala Ala Arg
        115                 120                 125

Ala Gly Thr Ala Glu Glu Gly Glu Glu Asp Cys Arg Ser Tyr Cys Gly
    130                 135                 140

Ser Ser Ser Ser Val Leu Leu Cys Glu Asp Gly Asp Ala Ala
145                 150                 155                 160

Ser Arg Ser Pro Leu Pro Phe Asp Leu Asn Met Pro Pro Pro Gln Asp
                165                 170                 175
```

Gly Ala Leu Asp Ala Ala Ala Ala Glu Ala Asp Gln Met Thr Cys Arg
            180                 185                 190

Tyr Asp Thr Leu Leu Arg Leu
        195

<210> SEQ ID NO 6
<211> LENGTH: 858
<212> TYPE: DNA
<213> ORGANISM: Triticum aestivum

<400> SEQUENCE: 6

```
ggccggccgc gatgcgcaag gcgaggccgc cgcagcccca gccgcagccg tcgcagcagt      60
cgccggagat ccggtaccgc ggcgtgcgga agcgcccctc gggccgctac gccgccgaga     120
tccgggaccc ggccaagaag acgccgatct ggctcggcac cttcgactgc ccgaggacg      180
ccgcccgcgc ctacgactcc gccgcccgat ccctccgcgg gcccaccgcc cgcaccaact     240
tcccgccttc ctccgccacg cagccgccgc cgcggcctcc cctccccccc gcggcggccg     300
ccgccgcgac cgtcacgtcc agccacagca gcaccgtcga gtcctggagc ggcggcgggc     360
cccgcgcccc cgccagggcc cgcagcgccg cccgagctgg cacggccgag gaggggggagg    420
aggactgccg cagctactgc ggctcctcgt cctccgtcct cctctgcgag gatggggacg     480
acgcggccgc ctcccgctcc ccgctgccct cgatctgaa catgccgccc cgcaggacg       540
gggcccttga cgccgcggcc gccgaggccg atcagatgac ctgccgctac gacacgctgc     600
tccgcctcta gctcgacggc gacgagaata gcaaggattc gtgggagggg gaactgggga     660
aaggaacgag aaaagcgctt gccccgctc cgctctgctc tgcgtttctt ctttcaagct      720
accggtgtta ttttagagaa aaggctaccg atgttgtatc aatggttttg cgttttgctg     780
ttccttcgaa gcactcgtgt ataagagcca ttgcttcact ggatcacatt ttgtaggctt     840
gaagcaatat ccttcaaa                                                  858
```

<210> SEQ ID NO 7
<211> LENGTH: 199
<212> TYPE: PRT
<213> ORGANISM: Hordeum vulgare

<400> SEQUENCE: 7

Met Arg Arg Ala Arg Pro Pro Ala Gly Pro Gly Leu Glu Gly Asp Glu
1               5                   10                  15

Val Lys Tyr Arg Gly Val Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Ser Ala Glu Ala Ala Arg Ala Tyr Asp Ala Ala Ala Arg Asn
    50                  55                  60

Leu Arg Gly Ala Ala Ala Arg Thr Asn Phe Pro Ala Ser Pro Ala Ala
65                  70                  75                  80

Ala Pro Pro Arg Ala Ala Pro Pro Ala Pro Val Ala Ala Pro Ala Met
                85                  90                  95

Ala Ala Ala Ala Thr Ser Ser His Ser Ser Thr Ile Glu Ser Trp Ser
            100                 105                 110

Gly Gly Val Pro Ala Ala Gly Ile Leu Leu Arg Pro Ala Ala Ala Ile
        115                 120                 125

Gly Ala Pro Ala Val Glu Glu Asp Cys Arg Ser Tyr Cys Gly Ser Ser
    130                 135                 140

Ser Ser Ala Leu Cys Glu Asp Gly Ala Ser Gly Ala Ala Asp Glu
145                 150                 155                 160

Ala Ala Ala Pro Pro Arg Pro Ser Ser Ser Ser Leu Pro Phe Asp
            165                 170                 175

Leu Asn Leu Pro Asp Pro Ala Ala Ala Asp Glu Met Asp Trp Arg
        180                 185                 190

Cys Asp Thr Leu Leu Arg Leu
        195

<210> SEQ ID NO 8
<211> LENGTH: 850
<212> TYPE: DNA
<213> ORGANISM: Hordeum vulgare

<400> SEQUENCE: 8

```
ggcgaggcga gggcgatgcg gcgcgcgagg ccgcctgcgg ggccggggct ggagggggac      60
gaggtgaagt accgcggggt gcggcggcgc ccgtcgggcc ggtacgcggc cgagatccgc     120
gacccggcca agaagacccc gatctggctc ggcaccttcg actccgccga ggccgccgcg     180
cgcgcctacg acgcagccgc caggaacctc cgcggcgccg ccgcgcgcac caacttcccc     240
gcctcccccg ccgcggcgcc cccgcgcgcg cgccacccg ccccgtcgc cgcgccggcg       300
atggccgccg ctgccacgtc tagccacagc agcacgatcg agtcctggag cggcggcgtc     360
ccggccgccg ggatcctcct ccgccccgca gccgcgatcg gcgctccggc cgtcgaggag     420
gactgccgca gctactgcgg ctcctcctcg tccgcgctgt gcgaggacgg cgcgtccggg     480
gccgccgcag acgaggccgc cgcgcctccg cgccctcgt cctcgtcctc gctgcccttc      540
gatctgaacc tgccggaccc cgcggccgcc gccgacgaga tggactggcg ctgcgacacg     600
ctgctccgcc tctgatcgcg gtgcctgctg ccggcttcgg atgcgtcgca actcccccctt    660
cctcctcccc gctcccggac taacgcggcg gcgcggctgc ctactgccaa gtgcttttac     720
tatctcgata gaattggatt tttggtctct gttttactac cacaagttct ccatatctga     780
tactctgtct ttatgtgata atgtgaataa gttcatcatc atcatcatat ccacgggaaa     840
tagactgaaa                                                             850
```

<210> SEQ ID NO 9
<211> LENGTH: 386
<212> TYPE: PRT
<213> ORGANISM: triticum aestivum

<400> SEQUENCE: 9

Met Cys Gly Gly Ala Ile Leu Ala Gly Phe Ile Pro Pro Ser Ala Ala
1               5                   10                  15

Ala Ala Ala Ala Lys Ala Ala Ala Lys Lys Gln Gln Gln Gln Gln
            20                  25                  30

Gln Gln Gln Gln Arg Ser Val Thr Ala Asp Ser Leu Trp Pro Gly Leu
        35                  40                  45

Arg Lys Lys Pro Ala Glu Glu Glu Asp Phe Glu Ala Asp Phe Arg Asp
    50                  55                  60

Phe Glu Arg Asp Ser Asn Asp Asp Asp Ala Val Glu Glu Val Pro
65                  70                  75                  80

Pro Pro Pro Ala Thr Ala Gly Phe Ala Phe Ala Ala Ala Glu Val
                85                  90                  95

Ala Leu Pro Ala Pro Thr Arg Leu Asp Ala Ile Gln His Asp Gly Pro
            100                 105                 110

Ala Ala Lys Ser Val Lys Arg Val Arg Lys Asn Gln Tyr Arg Gly Ile
            115                 120                 125

Arg Gln Arg Pro Trp Gly Lys Trp Ala Ala Glu Ile Arg Asp Pro Ser
        130                 135                 140

Lys Gly Val Arg Val Trp Leu Gly Thr Tyr Asp Thr Ala Glu Glu Ala
145                 150                 155                 160

Ala Arg Ala Tyr Asp Ala Glu Ala Arg Lys Ile Arg Gly Lys Lys Ala
                165                 170                 175

Lys Val Asn Phe Pro Glu Glu Ala Pro Thr Val Gln Lys Ser Thr Leu
            180                 185                 190

Lys Pro Thr Ala Val Lys Ser Ala Lys Leu Ala Pro Pro Lys Thr
        195                 200                 205

Cys Glu Asp Glu Pro Phe Asn His Leu Ser Arg Gly Asp Asn Asp Leu
    210                 215                 220

Phe Ala Met Phe Ala Phe Asn Asp Lys Lys Val Ser Ala Lys Pro Ala
225                 230                 235                 240

Glu Ser Val Asp Ser Leu Leu Pro Val Lys Pro Leu Val Pro Thr Glu
                245                 250                 255

Thr Phe Gly Met Asn Met Leu Ser Asp Gln Ser Ser Asn Ser Phe Gly
            260                 265                 270

Ser Thr Asp Phe Gly Trp Asp Asp Glu Ala Met Thr Pro Asp Tyr Thr
        275                 280                 285

Ser Val Phe Val Pro Asn Ala Ala Ala Met Pro Ala Tyr Gly Glu Pro
    290                 295                 300

Ala Tyr Leu Gln Gly Gly Ala Pro Lys Arg Met Arg Asn Asn Phe Gly
305                 310                 315                 320

Val Ala Val Leu Pro Gln Gly Asn Gly Ala Gln Asp Ile Pro Ala Phe
                325                 330                 335

Asp His Glu Met Lys Tyr Ser Leu Pro Tyr Val Glu Ser Ser Ser Asp
            340                 345                 350

Gly Ser Met Asp Ser Leu Leu Leu Asn Gly Ala Met Gln Asp Gly Ala
        355                 360                 365

Ser Ser Gly Asp Leu Trp Ser Leu Asp Glu Leu Phe Met Ala Ala Gly
    370                 375                 380

Gly Tyr
385

<210> SEQ ID NO 10
<211> LENGTH: 1161
<212> TYPE: DNA
<213> ORGANISM: Triticum aestivum

<400> SEQUENCE: 10
atgtgcggcg gagccatcct cgcgggcttc atcccgccgt cggcggccgc cgcggcggcc      60
aaggcggcgg cagccaagaa gcagcagcag cagcagcagc agcagcagcg cagcgtgacg     120
gccgactcgc tctggccggg cctgcggaag aagccggccg aagaggagga cttcgaggcc     180
gacttccgcg acttcgagcg ggactccaac gacgacgacg acgcggtcga ggaggtcccc     240
ccaccgccgg ccacgcgggg cttcgccttc gccgccgcgg ccgaggtcgc gctcccggct     300
ccgacccgcc tagatgctat tcaacatgat ggacctgctg ccaaatcagt gaagcgcgtt     360
cggaagaatc agtacagagg gatccgccag cgtccctggg ggaaatgggc agctgaaatc     420
cgtgacccta gcaagggtgt ccgggtttgg ctcgggacat acgacactgc tgaggaggca     480

```
gccagggcat atgacgctga agcccgcaag atccgtggca agaaggccaa ggtcaatttt    540
cctgaggagg ctccaactgt tcagaagtcc accctgaagc caactgctgt gaaatcagca    600
aagctggctc cacctccgaa gacctgcgag gatgagccct caatcacctg gagcagagga    660
gacaatgatt tgttcgcgat gtttgccttc aatgacaaga aggtttctgc aaagccagct    720
gaaagtgtgg attcccttct tccagtgaaa cctcttgtgc ccactgagac attcgggatg    780
aacatgctct tgaccagag cagcaattca tttggctcca ctgactttgg gtgggacgac    840
gaggccatga ccccagacta cacatccgtc ttcgttccga atgctgctgc catgccggca    900
tacggcgagc ccgcttacct gcaaggtgga gctccaaaga gaatgaggaa caactttggt    960
gtagccgtgc tgcctcaggg aaatggtgca caagacatcc ctgcttttga ccatgagatg   1020
aagtactcgt tgccttatgt cgagagcagc tcggacggat cgatggacag ccttctgctg   1080
aatggtgcga tgcaggacgg ggcaagcagt ggggatctct ggagccttga tgagctcttc   1140
atggcggccg gtggttactg a                                             1161
```

<210> SEQ ID NO 11
<211> LENGTH: 383
<212> TYPE: PRT
<213> ORGANISM: triticum aestivum

<400> SEQUENCE: 11

```
Met Cys Gly Gly Ala Ile Leu Ala Gly Phe Ile Pro Pro Ser Ala Ala
1               5                   10                  15

Ala Ala Ala Ala Lys Ala Ala Ala Lys Lys Gln Gln Gln Gln Gln Gln
            20                  25                  30

Gln Arg Ser Val Thr Ala Asp Ser Leu Trp Pro Gly Leu Arg Lys Lys
        35                  40                  45

Pro Ala Glu Glu Glu Asp Phe Glu Ala Asp Phe Arg Asp Phe Glu Arg
    50                  55                  60

Asp Ser Asn Asp Asp Asp Ala Val Glu Glu Val Pro Pro Pro
65                  70                  75                  80

Ala Thr Ala Gly Phe Ala Phe Ala Ala Ala Glu Val Ala Leu Pro
                85                  90                  95

Ala Pro Thr Arg Leu Asp Ala Ile Gln His Asp Gly Pro Ala Ala Lys
            100                 105                 110

Ser Val Lys Arg Val Arg Lys Asn Gln Tyr Arg Gly Ile Arg Gln Arg
        115                 120                 125

Pro Trp Gly Lys Trp Ala Ala Glu Ile Arg Asp Pro Ser Lys Gly Val
    130                 135                 140

Arg Val Trp Leu Gly Thr Tyr Asp Thr Ala Glu Glu Ala Ala Arg Ala
145                 150                 155                 160

Tyr Asp Ala Glu Ala Arg Lys Ile Arg Gly Lys Lys Ala Lys Val Asn
                165                 170                 175

Phe Pro Glu Glu Ala Pro Thr Val Gln Lys Ser Thr Leu Lys Pro Thr
            180                 185                 190

Ala Val Lys Ser Ala Lys Leu Ala Pro Pro Lys Thr Cys Glu Asp
        195                 200                 205

Glu Pro Phe Asn His Leu Ser Arg Gly Asp Asn Asp Leu Phe Ala Met
    210                 215                 220

Phe Ala Phe Asn Asp Lys Lys Val Ser Ala Lys Pro Ala Glu Ser Val
225                 230                 235                 240

Asp Ser Leu Leu Pro Val Lys Pro Leu Val Pro Thr Glu Thr Phe Gly
                245                 250                 255
```

Met Asn Met Leu Ser Asp Gln Ser Ser Asn Ser Phe Gly Ser Thr Asp
                260                 265                 270

Phe Gly Trp Asp Asp Glu Ala Met Thr Pro Asp Tyr Thr Ser Val Phe
            275                 280                 285

Val Pro Asn Ala Ala Met Pro Ala Tyr Gly Glu Pro Ala Tyr Leu
        290                 295                 300

Gln Gly Gly Ala Pro Lys Arg Met Arg Asn Asn Phe Gly Val Ala Val
305                 310                 315                 320

Leu Pro Gln Gly Asn Gly Ala Gln Asp Ile Pro Ala Phe Asp His Glu
                325                 330                 335

Met Lys Tyr Ser Leu Pro His Val Glu Ser Ser Asp Gly Ser Met
            340                 345                 350

Asp Ser Leu Leu Leu Asn Gly Ala Met Gln Asp Gly Ala Ser Ser Gly
        355                 360                 365

Asp Phe Trp Ser Leu Asp Glu Leu Phe Met Ala Ala Gly Gly Tyr
    370                 375                 380

<210> SEQ ID NO 12
<211> LENGTH: 1532
<212> TYPE: DNA
<213> ORGANISM: triticum aestivum

<400> SEQUENCE: 12
aaagctcccc cgcctcctcc ttcactgtgc cgcccgtgct tcccctccgc tccccgcgcc      60
gatccaaagc ccagaccctc gccttgatcc gcatctcgcc atgtgcggcg gagccatcct     120
cgcgggcttc atcccgccgt cggcggccgc cgcggcggcc aaggcggcgg cagccaagaa     180
gcagcagcag cagcagcagc gcagcgtgac ggccgactcg ctctggccgg gcctgcggaa     240
gaagccggcc gaagaggagg acttcgaggc cgacttccgc gacttcgagc gggactccaa     300
cgacgacgac gacgcggtcg aggaggtccc cccaccgccg gccacggcgg gcttcgcctt     360
cgccgccgcg gccgaggtcg cgctcccggc tccgacccgc ctagatgcta ttcaacatga     420
tggacctgct gccaaatcag tgaagcgcgt tcggaagaat cagtacagag ggatccgcca     480
gcgtccctgg gggaaatggg cagctgaaat ccgtgaccct agcaagggtg tccgggtttg     540
gctcgggaca tacgcactg ctgaggaggc agccagggca tatgacgctg aagcccgcaa     600
gatccgtggc aagaaggcca aggtcaattt tcctgaggag gctccaactg ttcagaagtc     660
caccctgaag ccaactgctg tgaaatcagc aaagctggct ccacctccga agacctgcga     720
ggatgagccc ttcaatcacc tgagcagagg agacaatgat ttgttcgcga tgtttgcctt     780
caatgacaag aaggtttctg caaagccagc tgaaagtgtg gattcccttc ttccagtgaa     840
acctcttgtg cccactgaga cattcgggat gaacatgctc tctgaccaga gcagcaattc     900
atttggctcc actgactttg ggtgggacga cgaggccatg ccccagact acacatccgt     960 cttcgttccg aatgctgctg ccatgccggc atacggcgag cccgcttacc tgcaaggtgg    1020
agctccaaag agaatgagga caaactttgg tgtagccgtg ctgcctcagg gaaatggtgc    1080
acaagacatc cctgcttttg accatgagat gaagtactcg ttgcctcatg tcgagagcag    1140
ctcggacgga tcgatggaca gccttctgct gaatggtgcg atgcaggacg gggcaagcag    1200
tggggatttc tggagccttg atgagctctt catggcggct ggtggttatt gatggttctt    1260
gtcagtgtgg tctgcggata gcacaaatgt cccttgcatg tggccaagat gaagaagtgg    1320
tggtgcatgt ggccaggatg aaggataggt tgcatctgtt atgcttggta gcggatcaaa    1380

```
cctagctat gctaaagact gtatgctgct agcagtggaa ccgtatgtca tgtttataag    1440
tattttgttg ttgtatatcg cctctatgat tgggtgcatg ttggagactg gagtttaata    1500
aataaataca ttggtcatat gcctgatgca aa                                  1532

<210> SEQ ID NO 13
<211> LENGTH: 192
<212> TYPE: PRT
<213> ORGANISM: triticum aestivum

<400> SEQUENCE: 13

Ala Arg Gly Phe Phe Pro Ala Ser Lys Glu Ala Cys Ser Ala Cys Gly
1               5                   10                  15

Met Asp Gly Cys Leu Gly Cys Glu Phe Phe Gly Ala Glu Ala Thr Gly
            20                  25                  30

Ala Ile Ala Ala Ser Asp Ala Pro Arg Ala Ala Thr Ala Gly Gly Pro
        35                  40                  45

Gln Arg Arg Arg Arg Asn Lys Lys Asn Gln Tyr Arg Gly Val Arg Gln
    50                  55                  60

Arg Pro Trp Gly Lys Trp Ala Ala Glu Ile Arg Asp Pro Arg Arg Ala
65                  70                  75                  80

Ala Arg Val Trp Leu Gly Thr Phe Asp Thr Ala Glu Asp Ala Ala Arg
                85                  90                  95

Ala Tyr Asp Arg Ala Ala Val Glu Phe Arg Gly Pro Cys Ala Lys Leu
            100                 105                 110

Asn Phe Ser Phe Pro Glu Gln Gln Gln Leu Gly Gly Ser Gly Asn Ala
        115                 120                 125

Ala Ala Lys Ser Asp Ala Cys Ser Pro Ser Pro Ser Pro Arg Ser Gly
    130                 135                 140

Asp Gly Glu Glu Thr Gly Asp Leu Leu Trp Asp Gly Leu Val Asp Leu
145                 150                 155                 160

Met Lys Leu Asp Glu Ser Asp Leu Cys Leu Leu Pro Val Asp Asn
                165                 170                 175

Thr Leu Asp Met Leu His Ala Pro Gly Gln Arg Arg Leu Asp Ala Tyr
            180                 185                 190

<210> SEQ ID NO 14
<211> LENGTH: 707
<212> TYPE: DNA
<213> ORGANISM: triticum aestivum

<400> SEQUENCE: 14
gcacgaggct ttttcccggc gagcaaggag gcgtgctcgg cgtgcgggat ggacgggtgc      60
ctcgggtgcg agttcttcgg cgcggaggcc accggcgcga tcgcggcatc ggacgcgccg    120
agagcggcga ccgctggcgg gccgcagagg aggcggagga acaagaagaa ccagtaccgt    180
ggcgtcaggc agcggccctg ggcaagtggg cggcggagat ccgcgacccg cgccgcgcc     240 gcgcgggtgt ggctcgggac cttcgacacg gccgaggacg ccgccaggc ctacgaccgc     300 gccgccgtcg agttccgcgg cccgtgcgcc aagctcaact tctccttccc cgagcagcag    360
cagctgggtg gcagcggcaa tgccgcggcc aagtccgacg cgtgctcgcc gtcgccttcg    420
ccacgcagcg gagacgggga ggaaacaggt gacctgcttt gggacggctt ggtggacttg    480
atgaagctgg acgagagcga cctttgcttt ctgctcccgg tcgacaacac cttggacatg    540
cttcacgcac cggacagag acgattggat gcctatagt gctagacaaa tgttagacca     600
gtgtcactgt gcagcagatc aatcaacaca cattgtacga cggtcctgga tcctggttag    660
```

```
cacacgtcct agcttcggtt gtaaatatcc acccgatcaa tggaaaa                    707
```

<210> SEQ ID NO 15
<211> LENGTH: 251
<212> TYPE: PRT
<213> ORGANISM: tricticum durum

<400> SEQUENCE: 15

```
Met Lys Ala Ser Arg Glu Tyr Met Ile Arg Phe Glu Gly His Phe Glu
1               5                   10                  15

Glu Asp Pro Ser Ser Thr Thr Ala Glu Pro Pro Leu Pro Phe Ala Gly
            20                  25                  30

Arg Val Phe Ser Pro Glu Gln Glu Gln Ser Val Leu Val Ala Ala Leu
        35                  40                  45

Leu His Val Val Ser Gly Tyr Thr Thr Pro Ala Pro Ala Phe Phe
    50                  55                  60

Pro Ala Ser Lys Glu Ala Cys Ser Ala Cys Gly Met Asp Gly Cys Leu
65                  70                  75                  80

Gly Cys Glu Phe Phe Gly Ala Glu Ala Thr Gly Ala Ile Ala Ala Ser
                85                  90                  95

Asp Ala Pro Arg Ala Ala Thr Ala Gly Gly Pro Gln Arg Arg Arg Arg
            100                 105                 110

Asn Lys Lys Asn Gln Tyr Arg Gly Val Arg Gln Arg Pro Trp Gly Lys
        115                 120                 125

Trp Ala Ala Glu Ile Arg Asp Pro Arg Arg Ala Val Arg Val Trp Leu
130                 135                 140

Gly Thr Phe Asp Thr Ala Glu Asp Ala Ala Arg Ala Tyr Asp Arg Ala
145                 150                 155                 160

Ala Val Glu Phe Arg Gly Pro Cys Ala Lys Leu Asn Phe Ser Phe Pro
                165                 170                 175

Glu Gln Gln Gln Leu Gly Gly Ser Gly Asn Ala Ala Ala Lys Ser Asp
            180                 185                 190

Ala Cys Ser Pro Ser Pro Ser Pro Arg Ser Gly Asp Glu Glu Glu Thr
        195                 200                 205

Gly Asp Leu Leu Trp Asp Gly Leu Val Asp Leu Met Lys Leu Asp Glu
    210                 215                 220

Ser Asp Leu Cys Leu Leu Leu Pro Val Asp Asn Thr Leu Asp Met Leu
225                 230                 235                 240

His Ala Pro Gly Gln Arg Arg Leu His Ala Tyr
                245                 250
```

<210> SEQ ID NO 16
<211> LENGTH: 753
<212> TYPE: DNA
<213> ORGANISM: tricticum durum

<400> SEQUENCE: 16

```
atgaaggcga gccgggagta catgatccgc ttcgaaggcc acttcgagga ggacccgagc     60
tccacgacag ccgagccacc actgccgttc gccggcaggg ttttctcgcc agagcaggag    120
cagagcgtcc tggtcgccgc gctgctgcac gtcgtctccg gtacaccac gccggcaccg    180 gccttctttt tcccggcgag caaggaggcg tgctcggcgt gcgggatgga cgggtgcctc    240
gggtgcgagt tcttcggcgc ggaggccacc ggcgcgatcg cggcatcgga cgcgccgaga    300
gcggcgaccg ctggcgggcc gcagaggagg cggaggaaca agaagaacca gtaccgtggc    360
```

```
gtcaggcagc ggccctgggg caagtgggcg gcggagatcc gcgacccgcg ccgcgccgtg     420
cgggtgtggc tcgggacctt cgacacggcc gaggacgccg ccagggccta cgaccgcgcc     480
gccgtcgagt tccgcggccc gtgcgccaag ctcaacttct ccttccccga gcagcagcag     540
ctgggtggca gcggcaatgc cgcggccaag tccgacgcgt gctcgccgtc gccttcgcca     600
cgcagcgggg acgaggagga aacaggtgac ctgctctggg acggcttggt ggacttgatg     660
aagctggacg agagcgacct ctgcttgctg ctcccggtcg acaacacctt ggacatgctt     720
cacgcaccgg gacagagacg attggatgcc tat                                  753

<210> SEQ ID NO 17
<211> LENGTH: 197
<212> TYPE: PRT
<213> ORGANISM: zea mays

<400> SEQUENCE: 17

Met Arg Arg Ala Lys Pro Gln Gln Pro Ser Pro Ser Pro Glu Ile Arg
1               5                   10                  15

Tyr Arg Gly Val Arg Arg Arg Pro Ser Gly Arg Tyr Ala Ala Glu Ile
            20                  25                  30

Arg Asp Pro Ala Lys Lys Thr Pro Ile Trp Leu Gly Thr Phe Asp Ser
        35                  40                  45

Ala Glu Ala Ala Ala Ser Ala Tyr Asp Ala Ala Ala Arg Ser Leu Arg
    50                  55                  60

Gly Pro Thr Ala Arg Thr Asn Phe Pro Gly Ala Ala Ala Ser Ala Pro
65                  70                  75                  80

Arg His Arg Ala Arg Ser Ala Ser Ala Ser Ala Ala Ala Ala Ala Pro
                85                  90                  95

Ala Ala Val Pro Ala Thr Ser Ser His Ser Ser Thr Val Glu Ser Trp
            100                 105                 110

Ser Gly Gly Ala Pro Arg Val Ala Ala Pro Pro Arg Ser Ala Ala Ala
        115                 120                 125

Pro Met Glu Glu Asp Asp Asp Glu Asp Cys His Ser Tyr Cys Gly Ser
    130                 135                 140

Ser Ser Ser Val Leu Cys Glu Asp Ala Arg Gly Asp Asp Asp Asp Asp
145                 150                 155                 160

Ala Ala Ala Ser His Ala Pro Leu Pro Phe Asp Leu Asn Leu Pro Pro
                165                 170                 175

Pro Ile Asp Ala Ala Ala Glu Ala Asp Gln Met Gly Ala Arg Tyr Asp
            180                 185                 190

Thr Leu Leu His Leu
        195

<210> SEQ ID NO 18
<211> LENGTH: 914
<212> TYPE: DNA
<213> ORGANISM: zea mays

<400> SEQUENCE: 18
agtggccaaa ccctagcccg ccgagctccc gcgtgcgctc tccgccgccc gcctactcct     60
ctctgtccgc gatgcgccgg gcgaagccgc agcagccctc gccgtcgccc gagattcggt    120
accgcggcgt gcggaggcgg ccgtcgggc gctacgccgc cgagatccgg acccggcca      180 agaagacccc gatctggctc ggcaccttcg actccgccga ggccgccgcg agcgcctacg    240
acgccgccgc ccgatccctc cgtgggccca ccgcccgcac caacttcccc ggcgccgcgg    300
```

-continued

| | |
|---|---|
| cttccgcgcc gcggcacagg gcccgctccg cctccgcctc cgccgccgcc gcagccccg | 360 |
| cggcggtgcc ggccacgtct agccacagca gcaccgtcga gtcgtggagc ggcggcgcgc | 420 |
| cccgcgtcgc cgccccgccg cggagcgccg ccgcgcccat ggaggaggac gacgacgagg | 480 |
| actgccacag ctactgcgga tcctcgtcgt ccgtgctctg cgaagacgcc cgcggggacg | 540 |
| acgacgacga cgcggcggcg tcccacgcgc ccctgccgtt cgatctgaac ctgccgccgc | 600 |
| cgatcgacgc ggctgctgag gccgatcaga tgggtgcccg ctacgacacg ctactccacc | 660 |
| tctagctcgc gacgacggcc aggaattaga ggaagggatc gagaccgtct gtccttcttc | 720 |
| ggctgctgat ccggtggtgt tctatcgcta gatggataat tcttgccttt ttcccccttc | 780 |
| ttttcttctg ctactttttt tgttttcttc tcttaccacc acgatgatga tgattcgata | 840 |
| ttatgtgaat aattcagtta tgtccatgta agctgtgagg aaggaaatct gagcttttcc | 900 |
| ttatcttcct atgg | 914 |

<210> SEQ ID NO 19
<211> LENGTH: 3851
<212> TYPE: DNA
<213> ORGANISM: Triticum durum

<400> SEQUENCE: 19

| | |
|---|---|
| gtcggtttgt ggattttga acgcctgaac ctgtccggct taatttgatt atccacattg | 60 |
| aatggttaaa atgttcaaat ggtctgatca ggacccaaga tcataatctc ttctttcccc | 120 |
| tcatgctaag gtggctacgg caaagtactc ctcccctcga agctccaccg gccaaccagt | 180 |
| ggattctcct ctcctccatc tgccgctcta gcggctggtg acgggaggag aaccccggtg | 240 |
| ccttgactcc ggctaatagt ctaggttagc atttttttcct tgcacgggtg acgctcagat | 300 |
| ggatgacaac gcttcatctt caagttggtc ttccattgtt cgttcctcct cgaaatcgct | 360 |
| cgtcagggtg aagtcgccga agctctggca tagattactg cagtctcttc gggcgacaag | 420 |
| gttagaattt ctcgccaagt gtgtgcgatg gcgagatccg gtgtgaggtg cttcaaatca | 480 |
| atttaagggt tcaacggcgc tgaccacggc tccctgacgc tggttcttag gggcacgttc | 540 |
| atgaagactt cgtggctcat cgacaagttt aggcggactc cattatcagg gcggcgatac | 600 |
| cgatgcctca tcggctcttc tgacggcgac agtggtcgtt cggtggtcca aagaccttga | 660 |
| tctaattttt attatgttta gggtactttg taattccaat gaacttttat tcgatatctg | 720 |
| ggtattaaaa aaatatctaa accttttttt aacatagtac aattggagat gctcacatgc | 780 |
| actcacccca taaacacatg cacgcacttt ctacacctat gagagccttc aagacactga | 840 |
| gccgacataa aatcttaaaa ttgacgaaat cgtcataaac acctttatag tcaacgaaaa | 900 |
| catctcctca caccgaatgc acatagtcgg agtcactaaa aataaattca aaaaatcacg | 960 |
| accaccggtg tcaagtataa catgaactcc ggtatccacc gcaagaaatc aaaacatctc | 1020 |
| gcgcatctgg gtacacatcg tgacgtccac cgtcgacata gcccctgggt gcgtgcggt | 1080 |
| cgcgcagtta acgacgcagc gattccgggt ggcccacgta gtcggcaaat cgtacgtgtg | 1140 |
| ggtgggtggg tgcgccgggg agcgagctag atgcgctgaa ggcacagtct cgccctgtgc | 1200 |
| agccatgtgg cggggggcag cagccatcga gcgatcgcct cgcgtgccgc tgaactgaat | 1260 |
| cgatccatga gtcatgtctg ccgcgtcgta cgacccatgt gcagaggacg gagcccttgc | 1320 |
| cactgcccgc ccaggcagga tccgatgctg ctgactagtt tatccgccga tccgttcgcg | 1380 |
| tcccgacgac gagggccgat agtacgtccg gcgagctggt tatacactga tcacggattt | 1440 |
| gccaggacca ggaaggaggc gttttgcatc gcgatccac ggcgccaaac tttccaccgc | 1500 |

```
tggctgtcac ggcatcccgt gcaccgaaag tagccaataa tgactccagc tagtctcgta   1560
cggtcggtgg ccgggcttgg ccggtgagtt ttcttcccag gaatggacgg tgaaaaagaa   1620
accaaaaggc cgacacgcca ccggcatttg cccacgaaag cgctcatcaa agcgagaaag   1680
cagaaacaaa agaacggcca gcccgatcga tctgattaga agccctggac atcggggtgg   1740
cagtttaatc agtccgctca ccccgccgga ctccactcga gcaaggaaac cccacccgct   1800
ttgctaggtt cggcacgacg ggccggtgag cggatagtcg tttcgacccc acatgtcaac   1860
atcgggctct ctttctagag ccctctcgtc gtcctagtca tgtgctatca ctcccccgac   1920
gtgcacccct tgatttagta acgaaatcca ccacgaactc ttatcttcgt ccgctaccgg   1980
tgattgagca tccggaagaa tcgatgttaa tgcttcctca tcctcaaaaa aaaaaaaga   2040 atcaatgtta atgccacaca accgctaaaa taaaccccgg ccaaacattt gtggacaaaa   2100
tggctcacgc cactgtttca aaaatcgatc gatcacttaa tcaatcggtc gaattatctc   2160
aacctaaagt attgccggag agcgacgggc gtggacaagc gtcccgtcgg cagcggatgc   2220
ggaggagagg ccacggaggg aggcacccca ccgaccattc gcaccgggcc acgcctcggt   2280
gagcgtaact acccaccact ccacatggcg cccgccgacc tctcccgatg ccgtcgatgg   2340
cgcgtccgcc acgtcggact gaccgcccca cgacatgcgt cggggctcca ctggctcacg   2400
cgctgccccg tcacgccatt atttccggcc gacacgctgt cactcacgac gttgaaccgt   2460
ccttctttcc tgcttgtatt gtcctcacgt acagcgctac agggcacaga tgtacacctc   2520
tcgccagcgg ctccggatcg acctccttga cagcggctat ataaggaagc ctcttggcca   2580
ggacaccttc atcagtcaca aagccacaag ccaagaacca atacttgatc tgttgtttcc   2640
tttagctccc ggaagacctt ttagctgcac cgatcgatct cgatcatgga ggatgagagg   2700
agcacccagt cgtaccaggg aggtgaggcc gccgagcagg tggaggtgac ggacagggc   2760 ctcctcggca acctcctcgg caagaagaag gcggaggagg acaaggagaa gaaggaggag   2820
gagctggtca ccggcatgga gaaggtctcc gtggaagagc ccgaggtcaa gaaggaggag   2880
cacgtggatg gcgagaagaa ggagaccctc ttctccaagc tgcaccgatc cagctccagc   2940
tccagctcgg taagtgcaaa catgatttaa ttagtagcgt tttgctgtat tatttaggag   3000
attattagga tatggcacgg ttgttgcgat ttctgacctc gtgagtgatc gtctgtacag   3060
tctagtgacg aggaagagga ggaggtgatc gacgacaacg cgcaggtgat caagaggaag   3120
aagaagaagg gtctcaagga gaagctccag gagaagctgc ccggccacaa ggacaccgag   3180
ggtgagcacg tgacgggcct acccgcaccg gcggcccccg cgtccgtgca gacccaccat   3240
gacaccgacg tcgtcgtcga gaagatcgac ggtgacgtga agacagaggc gacaccggca   3300
gtgcccgagg aggagaagaa aggcttcttg gaaaagatca aggagaagct gcccggcggc   3360
cacaagaagc cggaggacgc tgctgcggtg cccgtcacgc acgctgctcc ggcgcccgtc   3420
acgcacgctg ctccagcacc ggtgcacgcg ccggcgccgg ccgccgagga ggtgagcagc   3480
cctgacgcga aggagaagaa gggcctgctg gcaagatca tggacaagct gcctggttac   3540
cacaagacag gggaggagga caaggccgcc gccgctacag gcgagcacaa gcccagcgct   3600
tgatcgccgc cgtgcccgag acccgtgacc ggacctcgat tgaattgttg gcgtgtgttg   3660 tgtttgctttt acgtctaagt tggtgtcaag gtgggagggg ttgatcgtct ttgaaggtcc   3720
ggtccgtgaa gcccgttgag tgacgggtgc ttctgtttca gtctttgaag gtcctggata   3780
ttgttaagct tgtttactta tgggcacttg tgtattggtt tattgctggg cattatgcct   3840
```

```
                                                          -continued
tgatattaaa g                                                      3851
```

<210> SEQ ID NO 20
<211> LENGTH: 10
<212> TYPE: PRT
<213> ORGANISM: Triticum aestivum

<400> SEQUENCE: 20

Lys Thr Pro Ile Trp Leu Gly Thr Phe Asp
1               5                   10

<210> SEQ ID NO 21
<211> LENGTH: 16
<212> TYPE: PRT
<213> ORGANISM: Arabidopsis thaliana
<220> FEATURE:
<221> NAME/KEY: VARIANT
<222> LOCATION: (4)..(4)
<223> OTHER INFORMATION: P or R
<220> FEATURE:
<221> NAME/KEY: VARIANT
<222> LOCATION: (8)..(11)
<223> OTHER INFORMATION: X = any amino acid

<400> SEQUENCE: 21

Pro Lys Lys Pro Ala Gly Arg Xaa Lys Phe Xaa Glu Thr Arg His Pro
1               5                   10                  15

<210> SEQ ID NO 22
<211> LENGTH: 5
<212> TYPE: PRT
<213> ORGANISM: Arabidopsis thaliana

<400> SEQUENCE: 22

Asp Ser Ala Trp Arg
1               5

<210> SEQ ID NO 23
<211> LENGTH: 57
<212> TYPE: PRT
<213> ORGANISM: Triticum aestivum

<400> SEQUENCE: 23

Arg Tyr Arg Gly Val Arg Lys Arg Pro Ser Gly Arg Tyr Ala Ala Glu
1               5                   10                  15

Ile Arg Asp Pro Ala Lys Lys Thr Pro Ile Trp Leu Gly Thr Phe Asp
                20                  25                  30

Cys Ala Glu Asp Ala Ala Arg Ala Tyr Asp Ser Ala Ala Arg Ser Leu
            35                  40                  45

Arg Gly Pro Thr Ala Arg Thr Asn Phe
        50                  55

<210> SEQ ID NO 24
<211> LENGTH: 57
<212> TYPE: PRT
<213> ORGANISM: Triticum aestivum

<400> SEQUENCE: 24

Arg Tyr Arg Gly Val Arg Lys Arg Ser Gly Arg Tyr Ala Ala Glu
1               5                   10                  15

Ile Arg Asp Pro Ala Lys Lys Thr Pro Ile Trp Leu Gly Thr Phe Asp
                20                  25                  30

Cys Ala Glu Asp Ala Ala Arg Ala Tyr Asp Ser Ala Ala Arg Ser Leu
            35                  40                  45

Arg Gly Pro Thr Ala Arg Thr Asn Phe
    50                  55

<210> SEQ ID NO 25
<211> LENGTH: 57
<212> TYPE: PRT
<213> ORGANISM: Triticum asestivum

<400> SEQUENCE: 25

Arg Tyr Arg Gly Val Arg Lys Arg Pro Ser Gly Arg Tyr Ala Ala Glu
1               5                   10                  15

Ile Arg Asp Pro Ala Lys Lys Thr Arg Ile Trp Leu Gly Thr Phe Asp
            20                  25                  30

Cys Ala Glu Asp Ala Ala Arg Ala Tyr Asp Ser Ala Ala Arg Ser Leu
        35                  40                  45

Arg Gly Pro Thr Ala Arg Thr Asn Phe
    50                  55

<210> SEQ ID NO 26
<211> LENGTH: 57
<212> TYPE: PRT
<213> ORGANISM: Triticum aestivum

<400> SEQUENCE: 26

Arg Tyr Arg Gly Val Arg Lys Arg Ser Gly Arg Tyr Ala Ala Glu
1               5                   10                  15

Ile Arg Asp Pro Ala Lys Lys Thr Arg Ile Trp Leu Gly Thr Phe Asp
            20                  25                  30

Cys Ala Glu Asp Ala Ala Arg Ala Tyr Asp Ser Ala Ala Arg Ser Leu
        35                  40                  45

Arg Gly Pro Thr Ala Arg Thr Asn Phe
    50                  55

<210> SEQ ID NO 27
<211> LENGTH: 7
<212> TYPE: PRT
<213> ORGANISM: Triticum aestivum
<220> FEATURE:
<221> NAME/KEY: VARIANT
<222> LOCATION: (1)..(1)
<223> OTHER INFORMATION: L or F
<220> FEATURE:
<221> NAME/KEY: VARIANT
<222> LOCATION: (5)..(5)
<223> OTHER INFORMATION: L or F
<220> FEATURE:
<221> NAME/KEY: VARIANT
<222> LOCATION: (6)..(6)
<223> OTHER INFORMATION: X = any amino acid

<400> SEQUENCE: 27

Leu Asp Leu Asn Phe Xaa Pro
1               5

<210> SEQ ID NO 28
<211> LENGTH: 13
<212> TYPE: DNA
<213> ORGANISM: Triticum aestivum

<400> SEQUENCE: 28
gctagccgcc agc                                                      13

<210> SEQ ID NO 29

```
<211> LENGTH: 16
<212> TYPE: DNA
<213> ORGANISM: Triticum aestivum

<400> SEQUENCE: 29
ttccggccga cacgct                                                        16

<210> SEQ ID NO 30
<211> LENGTH: 90
<212> TYPE: DNA
<213> ORGANISM: Triticum durum

<400> SEQUENCE: 30
tccactggct cacgcgctgc cccgtcacgc cattatttcc ggccgacacg ctgtcactca        60
cgacgttgaa ccgtccttct ttcctgcttg                                         90

<210> SEQ ID NO 31
<211> LENGTH: 20
<212> TYPE: DNA
<213> ORGANISM: Artificial Sequence
<220> FEATURE:
<223> OTHER INFORMATION: D7 promoter fragment per FIG 1B

<400> SEQUENCE: 31
ttccggccga cacgctgtca                                                    20

<210> SEQ ID NO 32
<211> LENGTH: 20
<212> TYPE: DNA
<213> ORGANISM: Artificial Sequence
<220> FEATURE:
<223> OTHER INFORMATION: M1 per FIG 1B

<400> SEQUENCE: 32
ttccggtcga cacgctgtca                                                    20

<210> SEQ ID NO 33
<211> LENGTH: 20
<212> TYPE: DNA
<213> ORGANISM: Artificial Sequence
<220> FEATURE:
<223> OTHER INFORMATION: M2 per FIG 1B

<400> SEQUENCE: 33
ttccggctga cacgctgtca                                                    20

<210> SEQ ID NO 34
<211> LENGTH: 20
<212> TYPE: DNA
<213> ORGANISM: Artificial Sequence
<220> FEATURE:
<223> OTHER INFORMATION: M3 per FIG 1B

<400> SEQUENCE: 34
ttccggccta cacgctgtca                                                    20

<210> SEQ ID NO 35
<211> LENGTH: 20
<212> TYPE: DNA
<213> ORGANISM: Artificial Sequence
<220> FEATURE:
<223> OTHER INFORMATION: M4 per FIG 1B

<400> SEQUENCE: 35
ttccggccga tacgctgtca                                                    20
```

<210> SEQ ID NO 36
<211> LENGTH: 2688
<212> TYPE: DNA
<213> ORGANISM: Triticum durum

<400> SEQUENCE: 36

| | | | | | |
|---|---|---|---|---|---|
| gtcggtttgt | ggattttga | acgcctgaac | ctgtccggct | taatttgatt | atccacattg | 60 |
| aatggttaaa | atgttcaaat | ggtctgatca | ggacccaaga | tcataatctc | ttctttcccc | 120 |
| tcatgctaag | gtggctacgg | caaagtactc | ctcccctcga | agctccaccg | gccaaccagt | 180 |
| ggattctcct | ctcctccatc | tgccgctcta | gcggctggtg | acgggaggag | aaccccggtg | 240 |
| ccttgactcc | ggctaatagt | ctaggttagc | attttttcct | tgcacgggtg | acgtcagat | 300 |
| ggatgacaac | gcttcatctt | caagttggtc | ttccattgtt | cgttcctcct | cgaaatcgct | 360 |
| cgtcagggtg | aagtcgccga | agctctggca | tagattactg | cagtctcttc | gggcgacaag | 420 |
| gttagaattt | ctcgccaagt | gtgtgcgatg | gcgagatccg | gtgtgaggtg | cttcaaatca | 480 |
| atttaagggt | tcaacggcgc | tgaccacggc | tccctgacgc | tggttcttag | ggcacgttc | 540 |
| atgaagactt | cgtggctcat | cgacaagttt | aggcggactc | cattatcagg | gcggcgatac | 600 |
| cgatgcctca | tcggctcttc | tgacggcgac | agtggtcgtt | cggtggtcca | aagaccttga | 660 |
| tctaattttt | attatgttta | gggtactttg | taattccaat | gaactttat | tcgatatctg | 720 |
| ggtattaaaa | aaatatctaa | acctttttt | aacatagtac | aattggagat | gctcacatgc | 780 |
| actcacccca | taaacacatg | cacgcacttt | ctacacctat | gagagccttc | aagacactga | 840 |
| gccgacataa | aatcttaaaa | ttgacgaaat | cgtcataaac | acctttatag | tcaacgaaaa | 900 |
| catctcctca | caccgaatgc | acatagtcgg | agtcactaaa | aataaattca | aaaaatcacg | 960 |
| accaccggtg | tcaagtataa | catgaactcc | ggtatccacc | gcaagaaatc | aaaacatctc | 1020 |
| gcgcatctgg | gtacacatcg | tgacgtccac | cgtcgacata | gccccctggg | tgcgtgcggt | 1080 |
| cgcgcagtta | acgacgcagc | gattccgggt | ggcccacgta | gtcggcaaat | cgtacgtgtg | 1140 |
| ggtgggtggg | tgcgccgggg | agcgagctag | atgcgctgaa | ggcacagtct | cgccctgtgc | 1200 |
| agccatgtgg | cggggggcag | cagccatcga | gcgatcgcct | cgcgtgccgc | tgaactgaat | 1260 |
| cgatccatga | gtcatgtctg | ccgcgtcgta | cgacccatgt | gcagaggacg | gagcccttgc | 1320 |
| cactgcccgc | caggcagga | tccgatgctg | ctgactagtt | tatccgccga | tccgttcgcg | 1380 |
| tcccgacgac | gagggccgat | agtacgtccg | gcgagctggt | tatacactga | tcacggattt | 1440 |
| gccaggacca | ggaaggaggc | gttttgcatc | gcgatcccac | ggcgccaaac | tttccaccgc | 1500 |
| tggctgtcac | ggcatcccgt | gcaccgaaag | tagccaataa | tgactccagc | tagtctcgta | 1560 |
| cggtcggtgg | ccgggcttgg | ccggtgagtt | ttcttcccag | gaatgacgg | tgaaaagaa | 1620 |
| accaaaaggc | cgacacgcca | ccggcatttg | cccacgaaag | cgctcatcaa | agcgagaaag | 1680 |
| cagaaacaaa | agaacggcca | gcccgatcga | tctgattaga | agccctggac | atcggggtgg | 1740 |
| cagtttaatc | agtccgctca | ccccgccgga | ctccactcga | gcaaggaaac | cccacccgct | 1800 |
| ttgctaggtt | cggcacgacg | ggccggtgag | cggatagtcg | tttcgacccc | acatgtcaac | 1860 |
| atcgggctct | ctttctagag | ccctctcgtc | gtccagtca | tgtgctatca | ctcccccgac | 1920 |
| gtgcacccct | tgatttagta | acgaaatcca | ccacgaactc | ttatcttcgt | ccgctaccgg | 1980 |
| tgattgagca | tccggaagaa | tcgatgttaa | tgcttcctca | tcctcaaaaa | aaaaaaaga | 2040 |
| atcaatgtta | atgccacaca | accgctaaaa | taaaccccgg | ccaaacattt | gtggacaaaa | 2100 |

```
tggctcacgc cactgtttca aaaatcgatc gatcacttaa tcaatcggtc gaattatctc    2160
aacctaaagt attgccggag agcgacgggc gtggacaagc gtcccgtcgg cagcggatgc    2220
ggaggagagg ccacggaggg aggcacccca ccgaccattc gcaccgggcc acgcctcggt    2280
gagcgtaact acccaccact ccacatggcg cccgccgacc tctcccgatg ccgtcgatgg    2340
cgcgtccgcc acgtcggact gaccgcccca cgacatgcgt cggggctcca ctggctcacg    2400
cgctgccccg tcacgccatt atttccggcc gacacgctgt cactcacgac gttgaaccgt    2460
ccttctttcc tgcttgtatt gtcctcacgt acagcgctac agggcacaga tgtacacctc    2520
tcgccagcgg ctccggatcg acctccttga cagcggctat ataaggaagc tcttggcca    2580 ggacaccttc atcagtcaca aagccacaag ccaagaacca atacttgatc tgttgtttcc    2640
tttagctccc ggaagacctt ttagctgcac cgatcgatct cgatcatg            2688
```

```
<210> SEQ ID NO 37
<211> LENGTH: 454
<212> TYPE: DNA
<213> ORGANISM: Triticum durum

<400> SEQUENCE: 37
ggagggaggc accccaccga ccattcgcac cgggccacgc ctcggtgagc gtaactaccc     60
accactccac atggcgcccg ccgacctctc ccgatgccgt cgatggcgcg tccgccacgt    120
cggactgacc gccccacgac atgcgtcggg gctccactgg ctcacgcgct gccccgtcac    180
gccattattt ccggccgaca cgctgtcact cacgacgttg aaccgtcctt ctttcctgct    240
tgtattgtcc tcacgtacag cgctacaggg cacagatgta cacctctcgc cagcggctcc    300
ggatcgacct ccttgacagc ggctatataa ggaagcctct ggccaggac accttcatca    360 gtcacaaagc cacaagccaa gaaccaatac ttgatctgtt gtttccttta gctcccggaa    420
gaccttttag ctgcaccgat cgatctcgat catg                                454
```

```
<210> SEQ ID NO 38
<211> LENGTH: 453
<212> TYPE: DNA
<213> ORGANISM: Hordeum vulgare

<400> SEQUENCE: 38
ggagggagca ccccaccgac cattcgcacc cggccacgcc tcggtgaccg taactgccca     60
ccgctccaca tggcgcccgc cgacctcccc cgatgccgtc gatcgcgcgt ccgccacgtc    120
ggactgaccg ccccacgaca tgcgtcgggg ctccactggc tcacgcgctg ccccgtcacg    180
ccattatttc cggccgacac gctgtcactc gcaacgccga gccgtccttc tttcttgctt    240
gtgtcctcac gtacagcgcc actgatgtgc acctttcggc accggctctc gatctcgatc    300
ggtctacttg acagcggcta tataaggacg agtcatagct gggcacctt catcattcag    360 aaagccacaa gccaagaacc aatagtcttt gctgatccgc tgttttctct agctcccacg    420
agtctttagc tgcaccgacc gatctcgatc atg                                 453
```

```
<210> SEQ ID NO 39
<211> LENGTH: 75
<212> TYPE: PRT
<213> ORGANISM: Triticum aestivum

<400> SEQUENCE: 39

Arg Tyr Arg Gly Val Arg Lys Arg Pro Ser Gly Arg Tyr Ala Ala Glu
1               5                   10                  15
```

```
Ile Arg Asp Pro Ala Lys Lys Thr Pro Ile Trp Leu Gly Thr Phe Asp
             20                  25                  30

Cys Ala Glu Asp Ala Ala Arg Ala Tyr Asp Ser Ala Ala Arg Ser Leu
         35                  40                  45

Arg Gly Pro Thr Ala Arg Thr Asn Phe Pro Ser Ser Ala Thr Gln
     50                  55                  60

Pro Pro Pro Arg Pro Pro Pro Pro Ala Ala
65                  70                  75

<210> SEQ ID NO 40
<211> LENGTH: 74
<212> TYPE: PRT
<213> ORGANISM: Triticum aestivum

<400> SEQUENCE: 40

Arg Tyr Arg Gly Val Arg Lys Arg Pro Ser Gly Arg Tyr Ala Ala Glu
1               5                   10                  15

Ile Arg Asp Pro Ala Lys Lys Thr Pro Ile Trp Leu Gly Thr Phe Asp
             20                  25                  30

Cys Ala Glu Asp Ala Ala Arg Ala Tyr Asp Ser Ala Ala Arg Ser Leu
         35                  40                  45

Arg Gly Pro Thr Ala Arg Thr Asn Phe Pro Ser Ser Ala Thr Gln
     50                  55                  60

Pro Pro Pro Arg Pro Pro Pro Pro Ala
65                  70

<210> SEQ ID NO 41
<211> LENGTH: 76
<212> TYPE: PRT
<213> ORGANISM: Hordeum vulgare

<400> SEQUENCE: 41

Lys Tyr Arg Gly Val Arg Arg Arg Pro Ser Gly Arg Tyr Ala Ala Glu
1               5                   10                  15

Ile Arg Asp Pro Ala Lys Lys Thr Pro Ile Trp Leu Gly Thr Phe Asp
             20                  25                  30

Ser Ala Glu Ala Ala Ala Arg Ala Tyr Asp Ala Ala Ala Arg Asn Leu
         35                  40                  45

Arg Gly Ala Ala Ala Arg Thr Asn Phe Pro Ala Ser Pro Ala Ala Ala
     50                  55                  60

Pro Pro Arg Ala Ala Pro Pro Ala Pro Val Ala Ala
65                  70                  75

<210> SEQ ID NO 42
<211> LENGTH: 76
<212> TYPE: PRT
<213> ORGANISM: Triticum aestivum

<400> SEQUENCE: 42

Gln Tyr Arg Gly Ile Arg Gln Arg Pro Trp Gly Lys Trp Ala Ala Glu
1               5                   10                  15

Ile Arg Asp Pro Ser Lys Gly Val Arg Val Trp Leu Gly Thr Tyr Asp
             20                  25                  30

Thr Ala Glu Glu Ala Ala Arg Ala Tyr Asp Ala Glu Ala Arg Lys Ile
         35                  40                  45

Arg Gly Lys Lys Ala Lys Val Asn Phe Pro Glu Glu Ala Pro Thr Val
     50                  55                  60

Gln Lys Ser Thr Leu Lys Pro Thr Ala Val Lys Ser
```

```
<210> SEQ ID NO 43
<211> LENGTH: 76
<212> TYPE: PRT
<213> ORGANISM: Triticum aestivum

<400> SEQUENCE: 43

Gln Tyr Arg Gly Ile Arg Gln Arg Pro Trp Gly Lys Trp Ala Ala Glu
1               5                   10                  15

Ile Arg Asp Pro Ser Lys Gly Val Arg Val Trp Leu Gly Thr Tyr Asp
                20                  25                  30

Thr Ala Glu Glu Ala Ala Arg Ala Tyr Asp Ala Glu Ala Arg Lys Ile
            35                  40                  45

Arg Gly Lys Lys Ala Lys Val Asn Phe Pro Glu Glu Ala Pro Thr Val
        50                  55                  60

Gln Lys Ser Thr Leu Lys Pro Thr Ala Val Lys Ser
65                  70                  75

<210> SEQ ID NO 44
<211> LENGTH: 76
<212> TYPE: PRT
<213> ORGANISM: Triticum aestivum

<400> SEQUENCE: 44

Gln Tyr Arg Gly Val Arg Gln Arg Pro Trp Gly Lys Trp Ala Ala Glu
1               5                   10                  15

Ile Arg Asp Pro Arg Arg Ala Ala Arg Val Trp Leu Gly Thr Phe Asp
                20                  25                  30

Thr Ala Glu Asp Ala Ala Arg Ala Tyr Asp Arg Ala Ala Val Glu Phe
            35                  40                  45

Arg Gly Pro Cys Ala Lys Leu Asn Phe Ser Phe Pro Glu Gln Gln Gln
        50                  55                  60

Leu Gly Gly Ser Gly Asn Ala Ala Ala Lys Ser Asp
65                  70                  75

<210> SEQ ID NO 45
<211> LENGTH: 80
<212> TYPE: PRT
<213> ORGANISM: Arabidopsis thaliana

<400> SEQUENCE: 45

Arg Tyr Arg Gly Val Arg Lys Arg Pro Trp Gly Arg Phe Ala Ala Glu
1               5                   10                  15

Ile Arg Asp Pro Leu Lys Lys Ser Arg Val Trp Leu Gly Thr Phe Asp
                20                  25                  30

Ser Ala Val Asp Ala Ala Arg Ala Tyr Asp Thr Ala Ala Arg Asn Leu
            35                  40                  45

Arg Gly Pro Lys Ala Lys Thr Asn Phe Pro Ile Asp Cys Ser Pro Ser
        50                  55                  60

Ser Pro Leu Gln Pro Leu Thr Tyr Leu His Asn Gln Asn Leu Cys Ser
65                  70                  75                  80

<210> SEQ ID NO 46
<211> LENGTH: 77
<212> TYPE: PRT
<213> ORGANISM: Arabidopsis thaliana

<400> SEQUENCE: 46
```

```
Arg Phe Arg Gly Val Arg Lys Arg Pro Trp Gly Arg Phe Ala Ala Glu
1               5                   10                  15

Ile Arg Asp Pro Trp Lys Lys Ala Arg Val Trp Leu Gly Thr Phe Asp
            20                  25                  30

Ser Ala Glu Glu Ala Ala Arg Ala Tyr Asp Ser Ala Ala Arg Asn Leu
        35                  40                  45

Arg Gly Pro Lys Ala Lys Thr Asn Phe Pro Ile Asp Ser Ser Ser Pro
    50                  55                  60

Pro Pro Pro Asn Leu Arg Phe Asn Gln Ile Arg Asn Gln
65                  70                  75
```

<210> SEQ ID NO 47
<211> LENGTH: 75
<212> TYPE: PRT
<213> ORGANISM: Arabidopsis thaliana

<400> SEQUENCE: 47

```
His Tyr Arg Gly Val Arg Lys Arg Pro Trp Gly Arg Tyr Ala Ala Glu
1               5                   10                  15

Ile Arg Asp Pro Trp Lys Lys Thr Arg Val Trp Leu Gly Thr Phe Asp
            20                  25                  30

Thr Pro Glu Glu Ala Ala Leu Ala Tyr Asp Gly Ala Ala Arg Phe Leu
        35                  40                  45

Arg Gly Ile Lys Ala Lys Thr Asn Phe Pro Ser Pro Leu Ser Leu Asp
    50                  55                  60

Leu Asn His Leu Pro Ser Ala Pro Ser Ala Ala
65                  70                  75
```

<210> SEQ ID NO 48
<211> LENGTH: 68
<212> TYPE: PRT
<213> ORGANISM: Arabidopsis thaliana

<400> SEQUENCE: 48

```
Arg Tyr Arg Gly Val Arg Lys Arg Pro Trp Gly Arg Tyr Ala Ala Glu
1               5                   10                  15

Ile Arg Asp Pro Phe Lys Lys Ser Arg Val Trp Leu Gly Thr Phe Asp
            20                  25                  30

Thr Pro Glu Glu Ala Ala Arg Ala Tyr Asp Lys Arg Ala Ile Glu Phe
        35                  40                  45

Arg Gly Ala Lys Ala Lys Thr Asn Phe Pro Cys Tyr Asn Ile Asn Ala
    50                  55                  60

His Cys Leu Ser
65
```

<210> SEQ ID NO 49
<211> LENGTH: 70
<212> TYPE: PRT
<213> ORGANISM: Arabidopsis thaliana

<400> SEQUENCE: 49

```
Arg Tyr Arg Gly Val Arg Lys Arg Pro Trp Gly Arg Tyr Ala Ala Glu
1               5                   10                  15

Ile Arg Asp Pro Val Lys Lys Thr Arg Val Trp Leu Gly Thr Phe Asp
            20                  25                  30

Thr Ala Gln Gln Ala Ala Arg Ala Tyr Asp Ala Ala Ala Arg Asp Phe
        35                  40                  45

Arg Gly Val Lys Ala Lys Thr Asn Phe Gly Val Ile Val Gly Ser Ser
```

-continued

```
                50                  55                  60

Pro Thr Gln Ser Ser Thr
 65                  70

<210> SEQ ID NO 50
<211> LENGTH: 71
<212> TYPE: PRT
<213> ORGANISM: Arabidopsis thaliana

<400> SEQUENCE: 50

His Phe Arg Gly Val Arg Lys Arg Pro Trp Gly Arg Tyr Ala Ala Glu
  1               5                  10                  15

Ile Arg Asp Pro Gly Lys Lys Thr Arg Val Trp Leu Gly Thr Phe Asp
                20                  25                  30

Thr Ala Glu Glu Ala Ala Arg Ala Tyr Asp Thr Ala Ala Arg Glu Phe
            35                  40                  45

Arg Gly Ser Lys Ala Lys Thr Asn Phe Pro Leu Pro Gly Glu Ser Thr
        50                  55                  60

Thr Val Asn Asp Gly Gly Glu
 65                  70

<210> SEQ ID NO 51
<211> LENGTH: 87
<212> TYPE: PRT
<213> ORGANISM: Arabidopsis thaliana

<400> SEQUENCE: 51

Arg Tyr Arg Gly Val Arg Lys Arg Pro Trp Gly Arg Tyr Ala Ala Glu
  1               5                  10                  15

Ile Arg Asp Pro Gly Lys Lys Thr Arg Val Trp Leu Gly Thr Phe Asp
                20                  25                  30

Thr Ala Glu Glu Ala Ala Arg Ala Tyr Asp Thr Ala Ala Arg Asp Phe
            35                  40                  45

Arg Gly Ala Lys Ala Lys Thr Asn Phe Pro Thr Phe Leu Glu Leu Ser
        50                  55                  60

Asp Gln Lys Val Pro Thr Gly Phe Ala Arg Ser Pro Ser Gln Ser Ser
 65                  70                  75                  80

Thr Leu Asp Cys Ala Ser Pro
                85

<210> SEQ ID NO 52
<211> LENGTH: 76
<212> TYPE: PRT
<213> ORGANISM: Arabidopsis thaliana

<400> SEQUENCE: 52

Arg Tyr Arg Gly Val Arg Arg Pro Trp Gly Arg Tyr Ala Ala Glu
  1               5                  10                  15

Ile Arg Asp Pro Val Lys Lys Lys Arg Val Trp Leu Gly Ser Phe Asn
                20                  25                  30

Thr Gly Glu Glu Ala Ala Arg Ala Tyr Asp Ser Ala Ala Ile Arg Phe
            35                  40                  45

Arg Gly Ser Lys Ala Thr Thr Asn Phe Pro Leu Ile Gly Tyr Tyr Gly
        50                  55                  60

Ile Ser Ser Ala Thr Pro Val Asn Asn Asn Leu Ser
 65                  70                  75

<210> SEQ ID NO 53
```

```
<211> LENGTH: 76
<212> TYPE: PRT
<213> ORGANISM: Hordeum vulgare

<400> SEQUENCE: 53

Gln Tyr Arg Gly Ile Arg Gln Arg Pro Trp Gly Lys Trp Ala Ala Glu
1               5                   10                  15

Ile Arg Asp Pro Ser Lys Gly Val Arg Val Trp Leu Gly Thr Tyr Asp
            20                  25                  30

Thr Ala Glu Glu Ala Ala Arg Ala Tyr Asp Ala Glu Ala Arg Lys Ile
        35                  40                  45

Arg Gly Lys Lys Ala Lys Val Asn Phe Pro Glu Asp Ala Pro Thr Val
    50                  55                  60

Gln Lys Ser Thr Leu Lys Pro Thr Ala Ala Lys Ser
65                  70                  75

<210> SEQ ID NO 54
<211> LENGTH: 76
<212> TYPE: PRT
<213> ORGANISM: Arabidopsis thaliana

<400> SEQUENCE: 54

His Tyr Arg Gly Val Arg Gln Arg Pro Trp Gly Lys Phe Ala Ala Glu
1               5                   10                  15

Ile Arg Asp Pro Ala Lys Asn Gly Ala Arg Val Trp Leu Gly Thr Phe
            20                  25                  30

Glu Thr Ala Glu Asp Ala Ala Leu Ala Tyr Asp Arg Ala Ala Phe Arg
        35                  40                  45

Met Arg Gly Ser Arg Ala Leu Leu Asn Phe Pro Leu Arg Val Asn Ser
    50                  55                  60

Gly Glu Pro Asp Pro Val Arg Ile Lys Ser Lys Arg
65                  70                  75

<210> SEQ ID NO 55
<211> LENGTH: 75
<212> TYPE: PRT
<213> ORGANISM: Arabidopsis thaliana

<400> SEQUENCE: 55

Ser Phe Arg Gly Val Arg Gln Arg Ile Trp Gly Lys Trp Val Ala Glu
1               5                   10                  15

Ile Arg Glu Pro Asn Arg Gly Ser Arg Leu Trp Leu Gly Thr Phe Pro
            20                  25                  30

Thr Ala Gln Glu Ala Ala Ser Ala Tyr Asp Glu Ala Ala Lys Ala Met
        35                  40                  45

Tyr Gly Pro Leu Ala Arg Leu Asn Phe Pro Arg Ser Asp Ala Ser Glu
    50                  55                  60

Val Thr Ser Thr Ser Ser Gln Ser Glu Val Cys
65                  70                  75

<210> SEQ ID NO 56
<211> LENGTH: 76
<212> TYPE: PRT
<213> ORGANISM: Triticum aestivum

<400> SEQUENCE: 56

Ala Tyr Arg Gly Val Arg Gln Arg Thr Trp Gly Lys Trp Val Ala Glu
1               5                   10                  15

Ile Arg Glu Pro Asn Arg Gly Asn Arg Leu Trp Leu Gly Ser Phe Pro
```

```
                 20                  25                  30

Thr Ala Val Glu Ala Ala Arg Ala Tyr Asp Asp Ala Ala Arg Ala Met
             35                  40                  45

Tyr Gly Ala Lys Ala Arg Val Asn Phe Ser Glu Gln Ser Pro Asp Ala
         50                  55                  60

Ser Ser Gly Cys Thr Leu Ala Pro Pro Leu Leu Met
65                  70                  75

<210> SEQ ID NO 57
<211> LENGTH: 76
<212> TYPE: PRT
<213> ORGANISM: Triticum aestivum

<400> SEQUENCE: 57

Ser Tyr Arg Gly Val Arg Met Arg Ala Trp Gly Lys Trp Val Ser Glu
1               5                  10                  15

Ile Arg Glu Pro Arg Lys Lys Ser Arg Ile Trp Leu Gly Thr Phe Pro
             20                  25                  30

Cys Pro Glu Met Ala Ala Arg Ala His Asp Ala Ala Ala Leu Ser Ile
             35                  40                  45

Lys Gly Ala Arg Ala Val Leu Asn Phe Pro Asp Leu Ala Pro Ala Leu
         50                  55                  60

Pro Arg Pro Ala Ser Leu Ala Pro Cys Asp Val Gln
65                  70                  75

<210> SEQ ID NO 58
<211> LENGTH: 76
<212> TYPE: PRT
<213> ORGANISM: Arabidopsis thaliana

<400> SEQUENCE: 58

Ile Tyr Arg Gly Val Arg Arg Arg Asn Ser Gly Lys Trp Val Cys Glu
1               5                  10                  15

Val Arg Glu Pro Asn Lys Lys Thr Arg Ile Trp Leu Gly Thr Phe Gln
             20                  25                  30

Thr Ala Glu Met Ala Ala Arg Ala His Asp Val Ala Ala Leu Ala Leu
             35                  40                  45

Arg Gly Arg Ser Ala Cys Leu Asn Phe Ala Asp Ser Ala Trp Arg Leu
         50                  55                  60

Arg Ile Pro Glu Ser Thr Cys Ala Lys Asp Ile Gln
65                  70                  75

<210> SEQ ID NO 59
<211> LENGTH: 79
<212> TYPE: PRT
<213> ORGANISM: Triticum aestivum

<400> SEQUENCE: 59

Leu Tyr Arg Gly Val Arg Arg Arg Gly Ala Gly Arg Trp Val Cys
1               5                  10                  15

Glu Val Arg Gln Pro Asn Lys Lys Ser Arg Ile Trp Leu Gly Thr Phe
             20                  25                  30

Ala Thr Pro Glu Ala Ala Ala Arg Ala His Asp Val Ala Ala Leu Ala
             35                  40                  45

Leu Arg Gly Arg Ala Ala Cys Leu Asn Phe Ala Asp Ser Ala Thr Leu
         50                  55                  60

Leu Ala Val Asp Pro Ala Thr Leu Arg Thr Pro His Asp Ile Arg
65                  70                  75
```

<210> SEQ ID NO 60
<211> LENGTH: 255
<212> TYPE: PRT
<213> ORGANISM: Hordeum vulgare

<400> SEQUENCE: 60

Met Glu Asp Glu Arg Ser Thr Gln Ser Tyr Gln Gly Ala Glu Ala Asp
1               5                   10                  15

Gln Val Glu Val Thr Asp Arg Gly Leu Leu Gly Asn Leu Leu Gly Lys
            20                  25                  30

Lys Lys Glu Glu Asp Lys Lys Glu Glu Glu Leu Val Thr Gly
        35                  40                  45

Met Glu Lys Val Ser Val Glu Glu Pro Glu Val Lys Glu Asp Gly Glu
    50                  55                  60

Lys Lys Glu Thr Leu Phe Ser Lys Leu His Arg Ser Ser Ser Ser
65                  70                  75                  80

Ser Ser Ser Ser Asp Glu Glu Glu Glu Val Ile Asp Glu Asn
                85                  90                  95

Gly Glu Val Ile Lys Arg Lys Lys Lys Gly Leu Lys Glu Lys Leu
            100                 105                 110

Lys Glu Lys Leu Pro Gly His Lys Asp Asn Glu Ala Glu His Val Thr
        115                 120                 125

Gly Leu Pro Ala Pro Met Ala Pro Ala Ser Val Gln Thr His His Asp
    130                 135                 140

Thr Asp Val Val Glu Lys Ile Asp Gly Asp Ala Lys Thr Glu Ala
145                 150                 155                 160

Thr Pro Ala Val Pro Glu Glu Glu Lys Lys Gly Phe Leu Glu Lys Ile
                165                 170                 175

Lys Glu Lys Leu Pro Gly Gly His Lys Lys Pro Glu Asp Ala Ala Ala
            180                 185                 190

Val Pro Val Thr His Ala Ala Pro Ala Pro Val His Ala Pro Ala Pro
        195                 200                 205

Ala Ala Glu Glu Val Ser Ser Pro Asp Ala Lys Glu Lys Lys Gly Leu
    210                 215                 220

Leu Gly Lys Ile Met Asp Lys Leu Pro Gly Tyr His Lys Thr Gly Glu
225                 230                 235                 240

Glu Asp Lys Ala Ala Ala Pro Ser Gly Glu His Lys Pro Arg Ala
                245                 250                 255

<210> SEQ ID NO 61
<211> LENGTH: 290
<212> TYPE: PRT
<213> ORGANISM: Oryza sativa

<400> SEQUENCE: 61

Met Glu Asp Glu Arg Asn Thr Glu Ser His Gln Gly Gly Glu Ala Ala
1               5                   10                  15

Glu Gln Val Glu Val Lys Asp Arg Gly Leu Phe Asp Asn Leu Leu Gly
            20                  25                  30

Arg Lys Lys Asp Asp Gln Pro Glu Glu Lys Lys His Glu Glu Glu Leu
        35                  40                  45

Val Thr Gly Met Glu Lys Val Ser Val Glu Glu Pro Lys Lys Glu Glu
    50                  55                  60

His His Ala Glu Gly Glu Lys Lys Glu Ser Leu Leu Ser Lys Leu His
65                  70                  75                  80

Arg Ser Ser Ser Ser Ser Ser Ser Asp Glu Glu Glu Val
            85                  90              95

Ile Asp Asp Asn Gly Glu Val Val Lys Arg Lys Lys Lys Gly Leu
            100             105             110

Lys Glu Lys Ile Lys Glu Lys Leu Pro Gly His Lys Asp His Ala Gly
        115                 120                 125

Glu His Ala Pro Pro Pro Ala Ala Thr Gly Phe Pro Ala Pro Ala Pro
    130                 135                 140

Pro Ala Ser Val Val Thr Ala Ala Pro Thr Pro Ala Pro Ala Pro Val
145                 150                 155                 160

Val Thr His Gly Asp His His His Asp Thr Ala Val Pro Val Glu Lys
                165                 170                 175

Ile Glu Gly Asp His Ala Lys Thr Glu Ala Thr Leu Pro Arg Ala Pro
            180                 185                 190

Glu Glu Glu Lys Lys Gly Phe Leu Asp Lys Ile Lys Glu Lys Leu Pro
            195                 200                 205

Gly Gly His Lys Lys Pro Glu Asp Ala Thr Ala Val Pro Pro Pro Ala
            210                 215                 220

Ala Ser Pro Ala Ala Pro Ala Thr Thr Pro Ala Pro Ala His Pro Pro
225                 230                 235                 240

Pro Ala Thr Glu Glu Val Ser Ser Pro Asp Gly Lys Glu Lys Lys Gly
                245                 250                 255

Ile Leu Gly Lys Ile Met Glu Lys Leu Pro Gly Tyr His Lys Gly Ser
            260                 265                 270

Gly Glu Glu Asp Lys Thr Ala Ala Ala Thr Gly Glu His Lys Ser
            275                 280                 285

Ser Ala
    290

<210> SEQ ID NO 62
<211> LENGTH: 268
<212> TYPE: PRT
<213> ORGANISM: Triticum aestivum

<400> SEQUENCE: 62

Met Glu Asp Glu Arg Ser Thr Gln Ser Tyr Gln Gly Gly Glu Ala Ala
1               5                   10                  15

Glu Gln Val Glu Val Thr Asp Arg Gly Leu Leu Gly Asn Leu Leu Gly
            20                  25                  30

Lys Lys Lys Ala Glu Glu Asp Lys Glu Lys Lys Glu Glu Leu Val
        35                  40                  45

Thr Gly Met Glu Lys Val Ser Val Glu Pro Glu Val Lys Lys Glu
    50                  55                  60

Glu His Val Asp Gly Lys Lys Glu Thr Leu Phe Ser Lys Leu His
65              70                  75                  80

Arg Ser Ser Ser Ser Ser Ser Ser Asp Glu Glu Glu Glu
            85                  90                  95

Val Ile Asp Asp Asn Gly Glu Val Ile Lys Arg Lys Lys Lys Gly
            100                 105                 110

Leu Lys Glu Lys Leu Gln Glu Lys Leu Pro Gly His Lys Asp Thr Glu
        115                 120                 125

Gly Glu His Val Thr Ala Leu Pro Ala Pro Ala Ala Pro Ala Ser Val
    130                 135                 140

Gln Thr His His Asp Thr Asp Val Val Val Glu Lys Ile Asp Gly Asp

```
                145                 150                 155                 160
Val Lys Thr Glu Ala Thr Pro Ala Val Pro Glu Glu Lys Gly
                    165                 170                 175

Phe Leu Glu Lys Ile Lys Glu Lys Leu Pro Gly Gly His Lys Lys Pro
                    180                 185                 190

Glu Asp Ala Ala Val Pro Val Thr His Ala Ala Pro Ala Pro Val
            195                 200                 205

Thr His Ala Ala Pro Ala Pro Val His Ala Pro Ala Pro Ala Ala Glu
            210                 215                 220

Glu Val Ser Ser Pro Asp Ala Lys Glu Lys Gly Leu Leu Gly Lys
225                 230                 235                 240

Ile Met Asp Lys Leu Pro Gly Tyr His Lys Thr Gly Glu Glu Asp Lys
                    245                 250                 255

Ala Ala Ala Ala Thr Gly Glu His Lys Pro Ser Ala
            260                 265

<210> SEQ ID NO 63
<211> LENGTH: 262
<212> TYPE: PRT
<213> ORGANISM: Triticum aestivum

<400> SEQUENCE: 63

Met Glu Asp Glu Arg Ser Thr Gln Ser Tyr Gln Gly Gly Glu Ala Ala
1               5                   10                  15

Glu Gln Val Glu Val Thr Asp Arg Gly Leu Leu Gly Asn Leu Leu Gly
                20                  25                  30

Lys Lys Lys Ala Glu Glu Asp Lys Glu Lys Glu Glu Leu Val Thr
            35                  40                  45

Gly Met Glu Lys Val Ser Val Glu Glu Pro Val Lys Lys Glu Glu
        50                  55                  60

His Glu Asp Gly Glu Lys Lys Glu Thr Leu Phe Ser Lys Leu His Arg
65                  70                  75                  80

Ser Ser Ser Ser Ser Ser Ser Ser Asp Glu Glu Glu Glu Glu Val
                    85                  90                  95

Ile Asp Asp Asn Gly Glu Val Ile Lys Arg Lys Lys Lys Gly Leu
            100                 105                 110

Lys Glu Lys Leu Gln Gly Lys Leu Pro Gly His Lys Asp Thr Glu Gly
                115                 120                 125

Glu His Val Thr Gly Leu Pro Ala Pro Ala Ala Pro Ala Ser Val Gln
            130                 135                 140

Thr His Gly Gly His His Asp Thr Asp Val Val Val Glu Lys Ile Asp
145                 150                 155                 160

Gly Asp Val Lys Thr Glu Ala Ala Pro Ala Val Pro Glu Glu Lys
                    165                 170                 175

Lys Gly Phe Leu Glu Lys Ile Lys Glu Lys Leu Pro Gly Gly His Lys
                180                 185                 190

Lys Pro Glu Asp Ala Ala Ala Val Pro Val Thr His Ala Ala Pro Ala
            195                 200                 205

Pro Val His Ala Pro Val Pro Ala Pro Glu Glu Val Ser Ser Pro Asp
            210                 215                 220

Ala Lys Glu Lys Lys Gly Leu Leu Gly Lys Ile Met Asp Lys Leu Pro
225                 230                 235                 240

Gly Tyr His Lys Thr Gly Glu Glu Asp Lys Ala Ala Ala Ala Thr Gly
                245                 250                 255
```

Glu His Lys Pro Ser Ala
            260

<210> SEQ ID NO 64
<211> LENGTH: 259
<212> TYPE: PRT
<213> ORGANISM: Triticum aestivum

<400> SEQUENCE: 64

Met Glu Asp Glu Arg Ser Thr Gln Ser Tyr Gln Gly Gly Glu Ala Ala
1               5                   10                  15

Glu Gln Val Glu Val Thr Asp Arg Gly Leu Leu Gly Asn Leu Leu Gly
            20                  25                  30

Lys Lys Lys Ala Glu Glu Asp Lys Glu Lys Gln Glu Glu Leu Val Thr
        35                  40                  45

Gly Met Glu Lys Val Ser Val Glu Glu Pro Glu Val Lys Lys Glu Glu
    50                  55                  60

His Glu Asp Gly Glu Lys Lys Glu Thr Leu Phe Ser Lys Leu His Arg
65                  70                  75                  80

Ser Ser Ser Ser Ser Ser Ser Ser Asp Glu Glu Glu Glu Glu Glu Val
                85                  90                  95

Ile Asp Asp Asn Gly Glu Val Ile Lys Arg Lys Lys Lys Lys Gly Leu
            100                 105                 110

Lys Glu Lys Leu Lys Glu Lys Leu Pro Gly His Lys Asp Thr Glu Gly
        115                 120                 125

Glu His Val Thr Gly Leu Pro Ala Pro Ala Ala Pro Ala Ser Val Gln
    130                 135                 140

Thr His His Asp Thr Asp Val Val Val Glu Lys Ile Asp Gly Asp Val
145                 150                 155                 160

Lys Thr Glu Ala Ala Pro Ala Val Pro Glu Glu Glu Lys Lys Gly Phe
                165                 170                 175

Leu Glu Lys Ile Lys Glu Lys Leu Pro Gly Gly His Lys Lys Pro Glu
            180                 185                 190

Asp Ala Ala Pro Val Pro Val Thr His Ala Ala Pro Ala Pro Val His
        195                 200                 205

Ala Pro Ala Pro Ala Glu Glu Val Ser Ser Pro Asp Ala Lys Glu
    210                 215                 220

Lys Lys Gly Leu Leu Gly Lys Ile Met Asp Lys Leu Pro Gly Tyr His
225                 230                 235                 240

Lys Thr Gly Glu Glu Asp Lys Ala Ala Ala Ala Gly Glu His Lys
                245                 250                 255

Pro Ser Ala

<210> SEQ ID NO 65
<211> LENGTH: 54
<212> TYPE: PRT
<213> ORGANISM: Arabidopsis thaliana

<400> SEQUENCE: 65

Gly Val Arg Lys Arg Pro Trp Gly Arg Tyr Ala Ala Glu Ile Arg Asp
1               5                   10                  15

Pro Val Lys Lys Thr Arg Val Trp Leu Gly Thr Phe Asp Thr Ala Gln
            20                  25                  30

Gln Ala Ala Arg Ala Tyr Asp Ala Ala Ala Arg Asp Phe Arg Gly Val
        35                  40                  45

Lys Ala Lys Thr Asn Phe

<210> SEQ ID NO 66
<211> LENGTH: 11
<212> TYPE: PRT
<213> ORGANISM: Arabidopsis thaliana

<400> SEQUENCE: 66

Leu Asp Leu Asp Leu Asn Leu Ala Pro Pro Ala
1               5                   10

<210> SEQ ID NO 67
<211> LENGTH: 61
<212> TYPE: PRT
<213> ORGANISM: Glycine max

<400> SEQUENCE: 67

Val Lys Glu Val His Phe Arg Gly Val Arg Lys Arg Pro Trp Gly Arg
1               5                   10                  15

Tyr Ala Ala Glu Ile Arg Asp Pro Gly Lys Lys Ser Arg Val Trp Leu
                20                  25                  30

Gly Thr Phe Asp Thr Ala Glu Glu Ala Ala Arg Ala Tyr Asp Ala Ala
            35                  40                  45

Ala Arg Glu Phe Arg Gly Pro Lys Ala Lys Thr Asn Phe
        50                  55                  60

<210> SEQ ID NO 68
<211> LENGTH: 11
<212> TYPE: PRT
<213> ORGANISM: Glycine max

<400> SEQUENCE: 68

Phe Asp Leu Asp Leu Asn His Pro Pro His
1               5                   10

<210> SEQ ID NO 69
<211> LENGTH: 54
<212> TYPE: PRT
<213> ORGANISM: Nicotiana sylvestris

<400> SEQUENCE: 69

Gly Val Arg Lys Arg Pro Trp Gly Arg Tyr Ala Ala Glu Ile Arg Asp
1               5                   10                  15

Pro Gly Lys Lys Ser Arg Val Trp Leu Gly Thr Phe Asp Thr Ala Glu
                20                  25                  30

Glu Ala Ala Lys Ala Tyr Asp Thr Ala Ala Arg Glu Phe Arg Gly Pro
            35                  40                  45

Lys Ala Lys Thr Asn Phe
        50

<210> SEQ ID NO 70
<211> LENGTH: 13
<212> TYPE: PRT
<213> ORGANISM: Nicotiana sylvestris

<400> SEQUENCE: 70

Ile Asp Leu Asp Leu Asn Leu Ala Pro Pro Thr Glu Phe
1               5                   10

<210> SEQ ID NO 71
<211> LENGTH: 54
<212> TYPE: PRT

```
<213> ORGANISM: Arabidopsis thaliana

<400> SEQUENCE: 71

Gly Val Arg Lys Arg Pro Trp Gly Arg Tyr Ala Ala Glu Ile Arg Asp
1               5                   10                  15

Pro Gly Lys Lys Thr Arg Val Trp Leu Gly Thr Phe Asp Thr Ala Glu
            20                  25                  30

Glu Ala Ala Arg Ala Tyr Asp Thr Ala Arg Glu Phe Arg Gly Ser
        35                  40                  45

Lys Ala Lys Thr Asn Phe
    50

<210> SEQ ID NO 72
<211> LENGTH: 11
<212> TYPE: PRT
<213> ORGANISM: Arabidopsis thaliana

<400> SEQUENCE: 72

Leu Asn Leu Asp Leu Asn Leu Ala Pro Pro Val
1               5                   10

<210> SEQ ID NO 73
<211> LENGTH: 54
<212> TYPE: PRT
<213> ORGANISM: Arabidopsis thaliana

<400> SEQUENCE: 73

Gly Val Arg Lys Arg Pro Trp Gly Arg Tyr Ala Ala Glu Ile Arg Asp
1               5                   10                  15

Pro Gly Lys Lys Thr Arg Val Trp Leu Gly Thr Phe Asp Thr Ala Glu
            20                  25                  30

Glu Ala Ala Arg Ala Tyr Asp Thr Ala Ala Arg Asp Phe Arg Gly Ala
        35                  40                  45

Lys Ala Lys Thr Asn Phe
    50

<210> SEQ ID NO 74
<211> LENGTH: 11
<212> TYPE: PRT
<213> ORGANISM: Arabidopsis thaliana

<400> SEQUENCE: 74

Leu Asp Leu Asp Leu Asn Leu Pro Pro Pro Ser
1               5                   10

<210> SEQ ID NO 75
<211> LENGTH: 54
<212> TYPE: PRT
<213> ORGANISM: Arabidopsis thaliana

<400> SEQUENCE: 75

Gly Val Arg Lys Arg Pro Trp Gly Arg Tyr Ala Ala Glu Ile Arg Asp
1               5                   10                  15

Pro Phe Lys Lys Ser Arg Val Trp Leu Gly Thr Phe Asp Thr Pro Glu
            20                  25                  30

Glu Ala Ala Arg Ala Tyr Asp Lys Arg Ala Ile Glu Phe Arg Gly Ala
        35                  40                  45

Lys Ala Lys Thr Asn Phe
    50
```

-continued

```
<210> SEQ ID NO 76
<211> LENGTH: 13
<212> TYPE: PRT
<213> ORGANISM: Arabidopsis thaliana

<400> SEQUENCE: 76

Leu Asp Leu Asp Leu Asn Phe Pro Pro Pro Glu Asn
1               5                   10

<210> SEQ ID NO 77
<211> LENGTH: 54
<212> TYPE: PRT
<213> ORGANISM: Arabidopsis thaliana

<400> SEQUENCE: 77

Gly Val Arg Lys Arg Pro Trp Gly Arg Tyr Ala Ala Glu Ile Arg Asp
1               5                   10                  15

Pro Trp Lys Lys Thr Arg Val Trp Leu Gly Thr Phe Asp Thr Pro Glu
                20                  25                  30

Glu Ala Ala Leu Ala Tyr Asp Gly Ala Ala Arg Phe Leu Arg Gly Ile
            35                  40                  45

Lys Ala Lys Thr Asn Phe
        50

<210> SEQ ID NO 78
<211> LENGTH: 13
<212> TYPE: PRT
<213> ORGANISM: Arabidopsis thaliana

<400> SEQUENCE: 78

Leu Ala Ile Asp Leu Asn Glu Pro Pro Pro Leu Trp Leu
1               5                   10

<210> SEQ ID NO 79
<211> LENGTH: 54
<212> TYPE: PRT
<213> ORGANISM: Triticum aestivum

<400> SEQUENCE: 79

Gly Val Arg Lys Arg Pro Ser Gly Arg Tyr Ala Ala Glu Ile Arg Asp
1               5                   10                  15

Pro Ala Lys Lys Thr Pro Ile Trp Leu Gly Thr Phe Asp Cys Ala Glu
                20                  25                  30

Asp Ala Ala Arg Ala Tyr Asp Ser Ala Ala Arg Ser Leu Arg Gly Pro
            35                  40                  45

Thr Ala Arg Thr Asn Phe
        50

<210> SEQ ID NO 80
<211> LENGTH: 17
<212> TYPE: PRT
<213> ORGANISM: Triticum aestivum

<400> SEQUENCE: 80

Leu Pro Phe Asp Leu Asn Met Pro Pro Gln Asp Gly Ala Leu Asp
1               5                   10                  15

Ala

<210> SEQ ID NO 81
<211> LENGTH: 54
<212> TYPE: PRT
<213> ORGANISM: Triticum aestivum
```

```
<400> SEQUENCE: 81

Gly Val Arg Lys Arg Pro Ser Gly Arg Tyr Ala Ala Glu Ile Arg Asp
1               5                   10                  15

Pro Ala Lys Lys Thr Pro Ile Trp Leu Gly Thr Phe Asp Cys Ala Glu
            20                  25                  30

Asp Ala Ala Arg Ala Tyr Asp Ser Ala Ala Arg Ser Leu Arg Gly Pro
        35                  40                  45

Thr Ala Arg Thr Asn Phe
        50

<210> SEQ ID NO 82
<211> LENGTH: 17
<212> TYPE: PRT
<213> ORGANISM: Triticum aestivum

<400> SEQUENCE: 82

Leu Pro Phe Asp Leu Asn Met Pro Pro Gln Asp Gly Ala Leu Asp
1               5                   10                  15

Ala

<210> SEQ ID NO 83
<211> LENGTH: 54
<212> TYPE: PRT
<213> ORGANISM: Hordeum vulgare

<400> SEQUENCE: 83

Gly Val Arg Arg Arg Pro Ser Gly Arg Tyr Ala Ala Glu Ile Arg Asp
1               5                   10                  15

Pro Ala Lys Lys Thr Pro Ile Trp Leu Gly Thr Phe Asp Ser Ala Glu
            20                  25                  30

Ala Ala Ala Arg Ala Tyr Asp Ala Ala Arg Asn Leu Arg Gly Ala
        35                  40                  45

Ala Ala Arg Thr Asn Phe
        50

<210> SEQ ID NO 84
<211> LENGTH: 11
<212> TYPE: PRT
<213> ORGANISM: Hordeum vulgare

<400> SEQUENCE: 84

Leu Pro Phe Asp Leu Asn Leu Pro Asp Pro Ala
1               5                   10

<210> SEQ ID NO 85
<211> LENGTH: 54
<212> TYPE: PRT
<213> ORGANISM: Arabidopsis thaliana

<400> SEQUENCE: 85

Gly Val Arg Lys Arg Pro Trp Gly Arg Phe Ala Ala Glu Ile Arg Asp
1               5                   10                  15

Pro Leu Lys Lys Ser Arg Val Trp Leu Gly Thr Phe Asp Ser Ala Val
            20                  25                  30

Asp Ala Ala Arg Ala Tyr Asp Thr Ala Ala Arg Asn Leu Arg Gly Pro
        35                  40                  45

Lys Ala Lys Thr Asn Phe
        50
```

<210> SEQ ID NO 86
<211> LENGTH: 15
<212> TYPE: PRT
<213> ORGANISM: Arabidopsis thaliana

<400> SEQUENCE: 86

Phe Gln Phe Asp Leu Asn Phe Pro Pro Leu Asp Gly Val Asp Leu
1               5                   10                  15

<210> SEQ ID NO 87
<211> LENGTH: 54
<212> TYPE: PRT
<213> ORGANISM: Arabidopsis thaliana

<400> SEQUENCE: 87

Gly Val Arg Lys Arg Pro Trp Gly Arg Phe Ala Ala Glu Ile Arg Asp
1               5                   10                  15

Pro Trp Lys Lys Ala Arg Val Trp Leu Gly Thr Phe Asp Ser Ala Glu
            20                  25                  30

Glu Ala Ala Arg Ala Tyr Asp Ser Ala Ala Arg Asn Leu Arg Gly Pro
        35                  40                  45

Lys Ala Lys Thr Asn Phe
    50

<210> SEQ ID NO 88
<211> LENGTH: 14
<212> TYPE: PRT
<213> ORGANISM: Arabidopsis thaliana

<400> SEQUENCE: 88

Phe Gln Phe Asp Leu Asn Phe Pro Pro Leu Asp Cys Val Asp
1               5                   10

<210> SEQ ID NO 89
<211> LENGTH: 60
<212> TYPE: PRT
<213> ORGANISM: Arabidopsis thaliana

<400> SEQUENCE: 89

Lys Glu Val Arg Tyr Arg Gly Val Arg Arg Arg Pro Trp Gly Arg Tyr
1               5                   10                  15

Ala Ala Glu Ile Arg Asp Pro Val Lys Lys Lys Arg Val Trp Leu Gly
            20                  25                  30

Ser Phe Asn Thr Gly Glu Glu Ala Ala Arg Ala Tyr Asp Ser Ala Ala
        35                  40                  45

Ile Arg Phe Arg Gly Ser Lys Ala Thr Thr Asn Phe
    50                  55                  60

<210> SEQ ID NO 90
<211> LENGTH: 9
<212> TYPE: PRT
<213> ORGANISM: Arabidopsis thaliana

<400> SEQUENCE: 90

Pro Asp Leu Asp Leu Asn Ala Ser Pro
1               5

PLANT TRANSCRIPTION FACTORS, PROMOTERS AND USES THEREOF

CROSS REFERENCE

This utility application claims the benefit of priority of PCT Application Number PCT/US13/21939 filed Jan. 17, 2013, and US Provisional Application Ser. No. 61/587,342, filed Jan. 17, 2012, both of which are incorporated herein by reference.

FIELD

This application relates to the field of plant molecular biology.

BACKGROUND

Drought stress in crop plants causes widespread yield loss. In addition, other abiotic stress such as low nitrogen also affects crop growth and yield. Improving agronomic traits in crop plants is beneficial to farmers. Several factors crop yield. Abiotic stress is the primary cause of crop loss worldwide, causing average yield losses of more than 50% for major crops (Boyer, (1982) Science 218:443-448; Bray, et al., (2000) In Biochemistry and Molecular Biology of Plants, Edited by Buchannan, et al., Amer. Soc. Plant Biol., pp. 1158-1249). Among the various abiotic stresses, drought is a major factor that limits crop productivity worldwide. Exposure of plants to a water-limiting environment during various developmental stages appears to activate various physiological and developmental changes. Molecular mechanisms of abiotic stress responses and the genetic regulatory networks of drought stress tolerance have been studied (Valliyodan, and Nguyen, (2006) Curr. Opin. Plant Biol. 9:189-195; Wang, et al., (2003) Planta 218:1-14); Vinocur and Altman, (2005) Curr. Opin. Biotechnol. 16:123-132; Chaves and Oliveira, (2004) J. Exp. Bot. 55:2365-2384; Shinozaki, et al., (2003) Curr. Opin. Plant Biol. 6:410-417; Yamaguchi-Shinozaki and Shinozaki, (2005) Trends Plant Sci. 10:88-94).

Various transcription factors (TFs) have been reported to be associated with a response to abiotic and biotic stress in plants. For example, the drought-responsive element (DRE) binding proteins (DREBs) or C-repeat (CRT) binding factors (CBFs), and the ethylene response factors (ERFs) are such transcription factors. The CBF/DREB proteins can regulate the expression of drought/cold stress-related genes by binding to a CCGAC core motif, while the ERF TFs are known to bind to the GCC box (GCCGCC). Both families of proteins contain the Apetala2 (AP2) domain, while the CBF/DREB proteins are distinguished further by the presence of two regions, PKKP/RAGRxKFxETRHP (SEQ ID NO: 21) (abbreviated PKKPAGR) and DSAWR (SEQ ID NO: 22), which are located immediately upstream and downstream, respectively, of the AP2/ERF DNA-binding domain. Jaglo et al (2001) Plant Physiol. 127:910-917; Canella et al. (2010) Biochim. Biophys. Acta. 1799(5-6):454-462. Although ERF proteins are generally known to bind the GCC box, at least two ERFs, one from pepper and the other from wheat, have been shown to associate with both the GCC box and the CRT/DRE element.

Expression of the dehydrin gene family, a class of Late Embryogenesis Abundant (LEA) proteins, is regulated by exposure to abiotic stress. The promoters of genes encoding dehydrins are strongly activated in vegetative tissues under stress conditions. cis-acting elements and respective TFs responsible for the constitutive and stress-inducible activation of either Wcor410 or Wcor410-like genes from other plants than those mentioned previously, have not yet been reported. The Wcor410 gene from wheat was originally identified as a gene encoding a LEA protein that accumulates to equal levels in root, crown and leaf tissues of freezing-tolerant Gramineae during cold acclimation.

ERF transcription factors, uses thereof and analysis of promoters are presented herein.

SUMMARY

A plant comprising in its genome a recombinant polynucleotide encoding a transcription factor designated ERF4 comprising an EAR motif having the amino acid sequence of KTPIWLGTFD (SEQ ID NO: 20), wherein the transcription factor is an activator of activated upon abiotic stress. In embodiment, the ERF transcription factor comprises the amino sequence that is at least 70% identical to SEQ ID NO: 1. In embodiment, the ERF polypeptide includes the amino sequence that is at least 80% or 95% identical to SEQ ID NO: 1.

Suitable plant species for transgenic manipulation include for example, maize, barley, wheat, soybean, rice, sugarcane, camelina, cotton, sorghum and brassica.

A method of increasing drought tolerance of a plant includes expressing a polynucleotide that suppresses the endogenous expression of a polypeptide, wherein the polypeptide comprises a conserved domain selected from the group consisting of SEQ ID NOS: 1, 3, 5, 7, 9, 11, 13, 15 and 17.

A method of increasing yield of a plant includes altering the endogenous expression level of a polypeptide, wherein the polypeptide comprises an EAR motif having the amino acid sequence of KTPIWLGTFD (SEQ ID NO: 20) and wherein the polypeptide is a transcriptional activator.

An isolated DNA molecule having promoter activity, wherein the DNA molecule includes a nucleotide sequence of SEQ ID NO: 19 or a fragment thereof, the fragment includes at least 95 contiguous nucleotides of SEQ ID NO: 19 having promoter activity. In an embodiment, the DNA molecule is operably linked to a heterologous coding sequence. Functional equivalents of the promoter of SEQ ID NO: 19 are also useful for expression of a heterologous DNA.

A transgenic plant includes a transformed polynucleotide encoding a portion of polypeptide comprising SEQ ID NO: 1, wherein the polypeptide portion has transcriptional activation activity.

BRIEF DESCRIPTION OF THE DRAWINGS AND SEQUENCE LISTING

The disclosure can be more fully understood from the following detailed description and the accompanying drawings and Sequence Listing which form a part of this application.

FIG. 1: (A) Identification of the functional drought-responsive DREs/CRTs by the 5' deletion analysis of the TdCor410b promoter using the transactivation of the GUS reporter gene in a transient expression assay. The full-length TdCor410b promoter and six promoter deletions were linked to the GUS reporter gene and co-transformed via particle bombardment into the cell suspension cultures with either pUbi-GFP (negative control) or pUbi-TaDREB3 (transcription activator). A schematic representation of the 5' terminal deletions of the promoter fused to the GUS gene is shown in the left part of the figure: asterisk (*) denotes the predicted DRE/CRT site. A negative control (a basal level of the full-length promoter activity) is shown in the right panel as an empty box. Error bars represent standard deviations (SD) bar (P<0.05). (B) Activation of promoter fragments by wounding, cold and drought in transgenic barley plants detected by Q-PCR. The indicated portions of the promoter are provided as SEQ ID NOs: 30-35, top to bottom.

Figure 2:
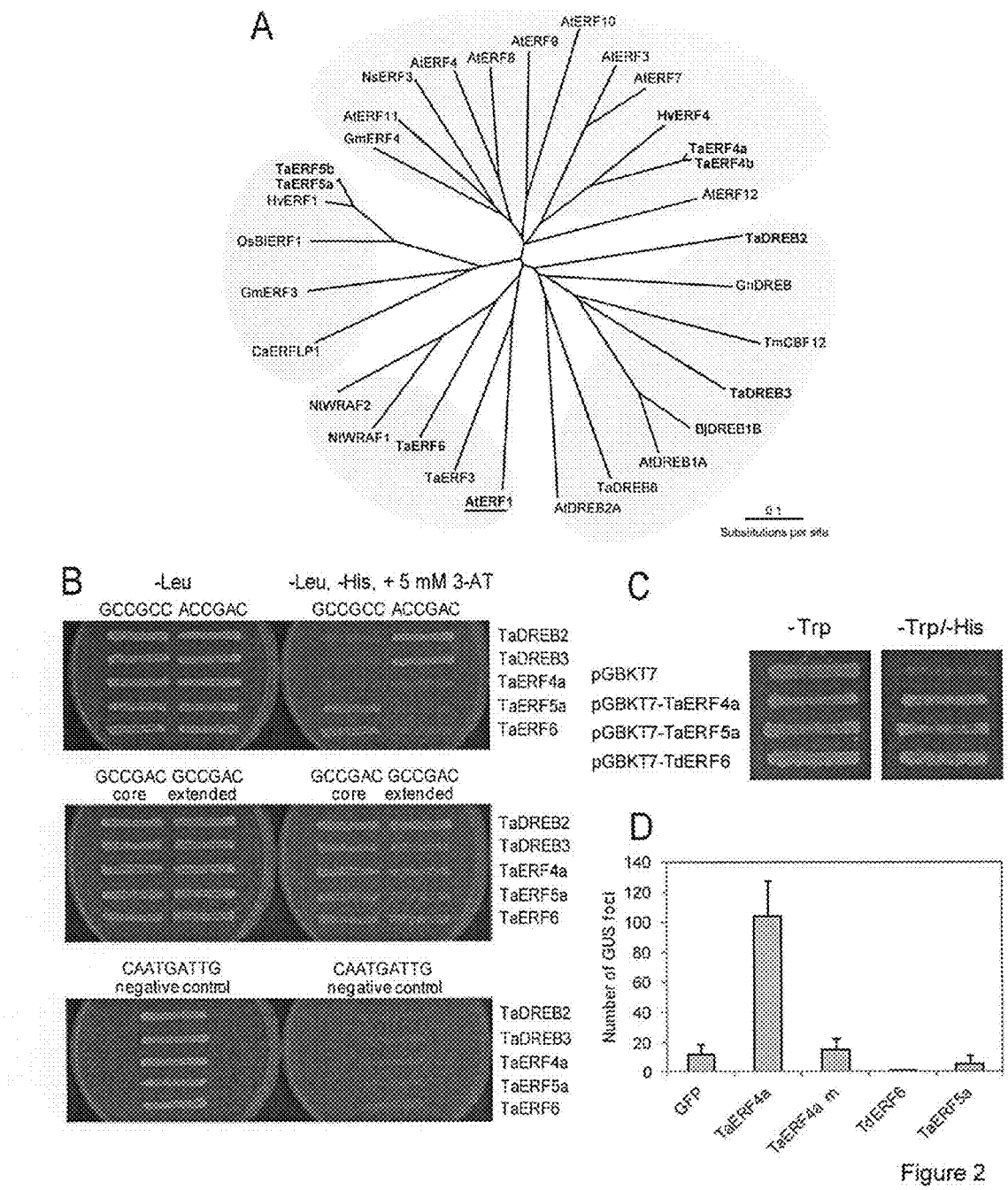

FIG. 2: Transcription factors isolated in the Y1H (yeast one-hybrid) screens and their properties. (A) An unrooted radial phylogenetic tree of the AP2-domain containing TFs. Amino acid sequences of 32 proteins were aligned with ProMals3D (Pei, et al., (2008) *Nucleic Acids Res* 36:2295-2300) and branch lengths were drawn to scale. Two-letter prefixes for sequence identifiers indicate species of origin. TFs isolated in this work are shown in bold. The *Arabidopsis* AtERF1 TF was used for construction of 3D models of the AP2 domains of TaERF4a, TaERF5a and TaDREB3 (B) Specificity of recognition of the known stress-responsive cis-elements by ERF and DREB TFs detected in the Y1H assay. Growth of yeast on selective (-Leu, -His, +5 mM 3-AT) medium indicates protein-DNA interaction. The cis-element for the HD-Zip class II TF was used as a negative control. (C) Demonstration of activator properties using ERFs in the Y2H assay. The presence of their own activation domains in the representatives from each subfamily of ERFs supports the activation of the yeast genes and consequent growth of yeast on the selective (-Leu, -Trp, -His, -Ade) medium. (D) Regulation of the TdCor410b promoter activity by representatives of each isolated subfamily. TFs were tested in a transient expression assay in a wheat cell culture. The pTdCor410b-GUS construct was co-bombarded with, left to right in graph, pUbi-GFP (GFP), pUbi-TaERF4a (TaERF4a), pUbi-TaERF4a mutated in EAR motif (TaERF4a m), pUbi-TaERF6 (TaERF6), and pUbi-TaERF5a (TaERF5a).

Figure 3:
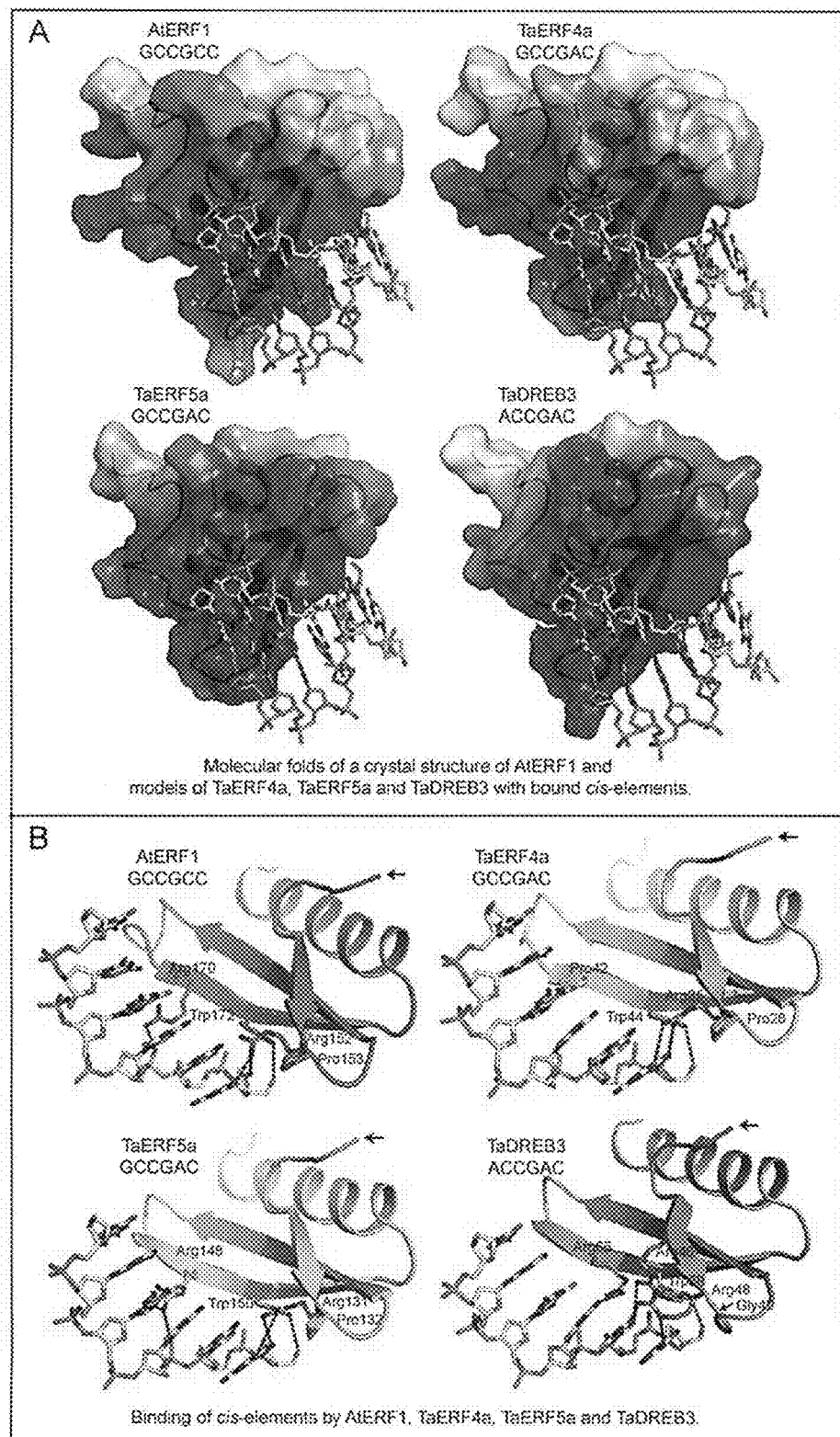

FIG. 3: (A) Molecular surface morphologies of the AP2 domains of the AtERF1, TaERF4a, TaERF5a and TaDREB3 transcription factors in complex with cis-elements. Surface representations indicate protein surfaces that are coded by electrostatic potentials. Double stranded DNA molecules (GCCGCC/GGCGGC, GCCGAC/GTCGGC and ACCGAC/GTCGGT) are indicated in sticks. Patches on protein surfaces indicate electro-neutral, electropositive and electronegative patches; the charged patched are contoured at ±5 kT/e. (B) Molecular folds of the AP2 domains of the AtERF1, TaERF4a, TaERF5a and TaDREB3 TFs in complex with cis-elements. Ribbon representations show the disposition of secondary structure elements, where antiparallel strands carry amino acid residues that mediate contacts between individual cis-elements and the AP2 domains. Ribbons represent AtERF1 (upper left), TaERF4a (upper right), TaERF5a (lower left) and TaDREB3 (lower right). Anrrows points to the $NH_2$-termini of each AP2 domain. The coding strands of cis-elements GCCGCC, GCGGAC and ACCGAC are shown in sticks. The interacting residues are shown in sticks (AtERF1, TaERF4a, TaERF5a and TaDREB3) The distances of ≥3.4 Å between the contacting residues (Arg and Trp) and cis-elements are indicated by dotted lines. The positions of respective Pro or Gly residues, following the Arg residues that contact cis-elements in the AP2 domains of ERF and TaDREB3 are indicated. The interplay of these residues within the structures of TFs suggests that the structural rigidity or flexibility could impact upon the selectivity of binding of individual cis-elements.

Figure 4:
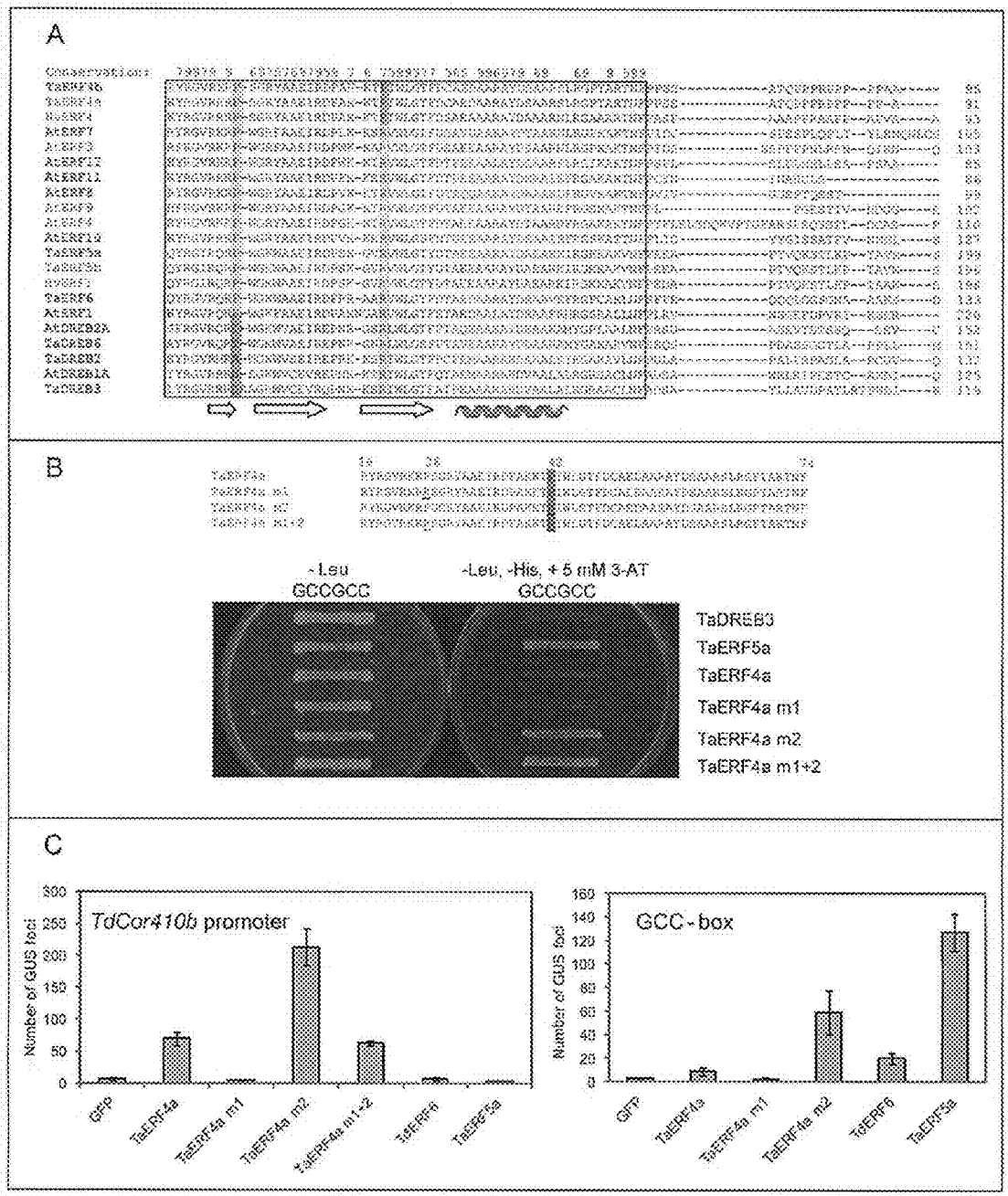

FIG. 4: (A) Multiple sequence alignment of the selected AP2 domains using PROMALS3D (Pei, et al., (2008) *Nucleic Acids Res* 36:2295-2300). Sequences shown are, top to bottom, SEQ ID NO: 39, 40, 41, 45, 46, 47, 48, 49, 50, 51, 52, 42, 43, 53, 44, 54, 55, 56, 57, 58, 59. Representative sequences are marked according to predicted secondary structures (red: alpha-helix, blue: beta-strand). The black box indicates the boundaries of the AP2 domains. The positions of highly conserved Pro residues in the ERF sequences and of variable non-proline residues in the DREB sequences are shown at position 9 in the figure, counting from the left. Pro residues at position 27 of the figure are conserved in TaERF4b, TaERF4a, and HvERF4 and correspond to Arg in remaining sequences of the figure. Consensus of secondary structure elements indicates the position of β-sheets (black arrows) and of an α-helix). The degree of conservation of residues is shown above the sequences by numbers with a conservation index of 5 and higher. (B) Influence of amino acid residue substitutions in the AP2 domain of the TaERF4a (SEQ ID NO: 23) on recognition of the GCC-box. TaDREB3 was used as a negative and TaERF5a as a positive control of interaction with the GCC-box. A mutation of Pro26 to Arg26 (underlined; SEQ ID NO: 24) has no influence on interaction of the TaERF4a variant with cis-element. A mutation of Pro42 to Arg42 (underlined and boxed; SEQ ID NO: 25) led to restoration of interaction and consequent growth of yeast on the selective (-Leu, -His, +5 mM 3-AT) medium; the sequence designated "TaERF4a m1+2" is SEQ ID NO: 26. (C) The artificial promoter, containing three repeats of the GCC-box was weakly activated by wild type TaERF4a. Regulation of the activity of the TdCor410b promoter and of the artificial promoter with substitution of the CRT element for tandem of three GCC-boxes was tested with representatives of each isolated ERF subfamily, and variants of TaERF4a with mutations in the AP2 domain.

Figure 5:
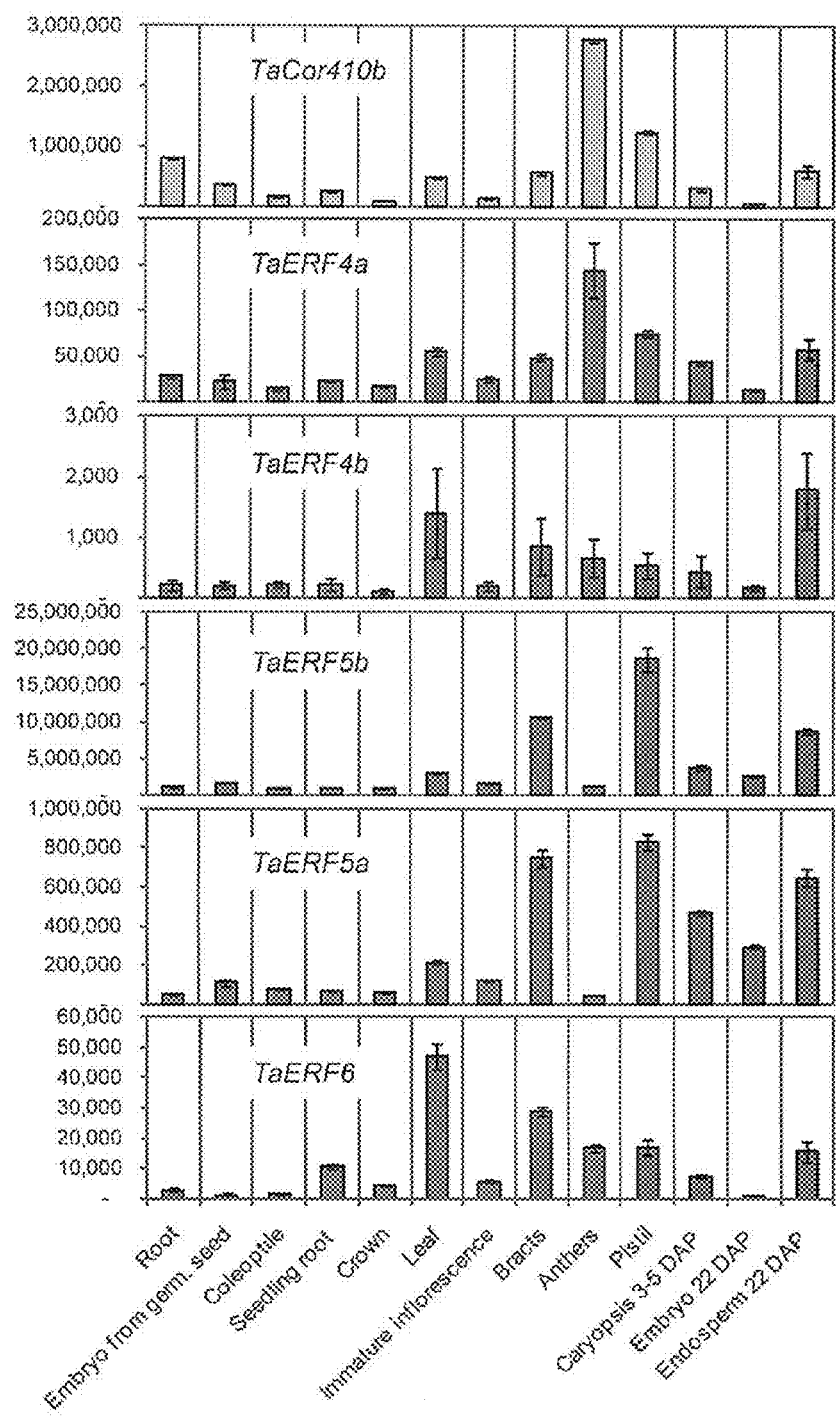

FIG. 5: Expression of TaCor410b and ERF genes in different wheat tissues in the absence of stress. Levels of expression were detected by Q-PCR and are shown as normalized transcription levels in arbitrary units.

Figure 6:
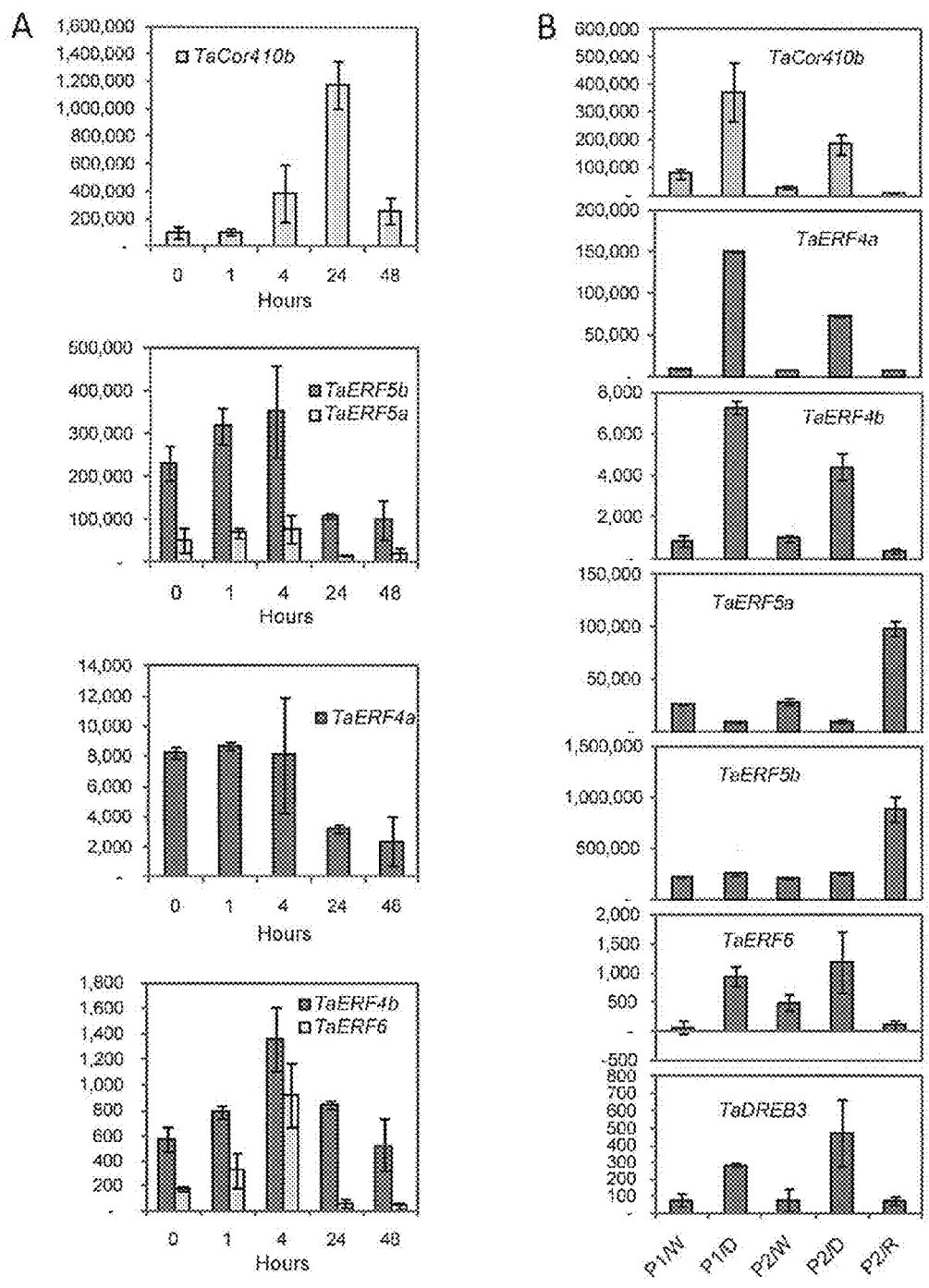

FIG. 6: Stress inducible expression of the TaCor410b and ERF genes in leaves of four-weeks-old seedlings. (A) Expression of the TaCor410b and ERF genes under cold (4° C.) stress. (B) Expression of the TaCor410b and ERF genes in leaves of two different plants (P1 and P2) under well-watered conditions (W), drought (D) and two-weeks after re-watering (R). Levels of expression were detected by Q-PCR and are shown as normalised transcription levels in arbitrary units.

Figure 7:
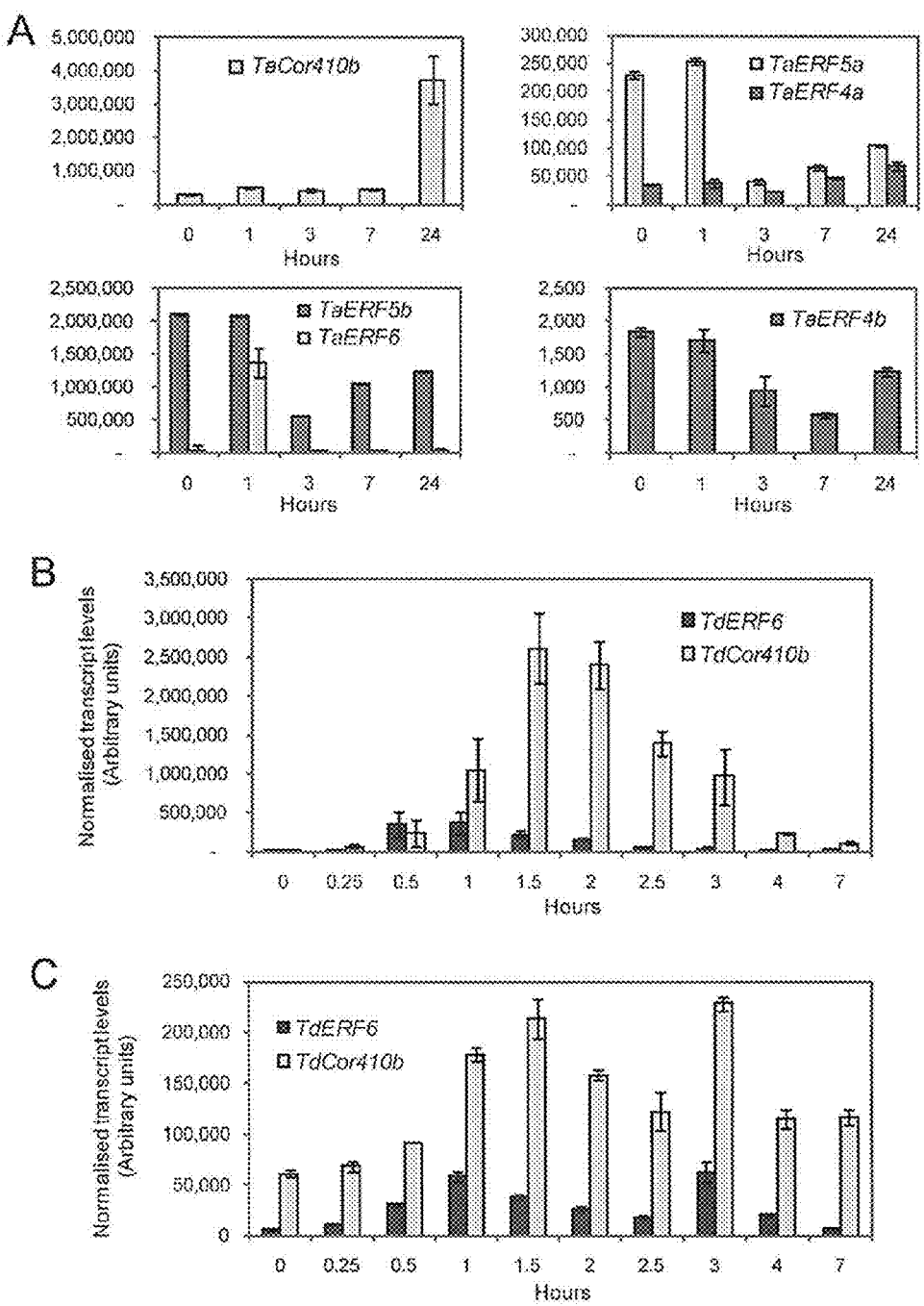

FIG. 7: Expression of the Cor410b and ERF genes in leaves and grain of bread and *durum* wheat subjected to mechanical wounding. (A) Expression of the TaCor410b and TaERF genes in wounded leaves of bread wheat. Levels of expression, detected by Q-PCR, are shown as normalized transcription levels in arbitrary units. (B) Expression of the TdCor410b and TdERF6 genes in wounded leaves of the *durum* wheat plants at flowering. (C) Expression of the TdCor410b and TdERF6 genes in wounded wheat grain, 8-15 days after pollination.

Figure 8:
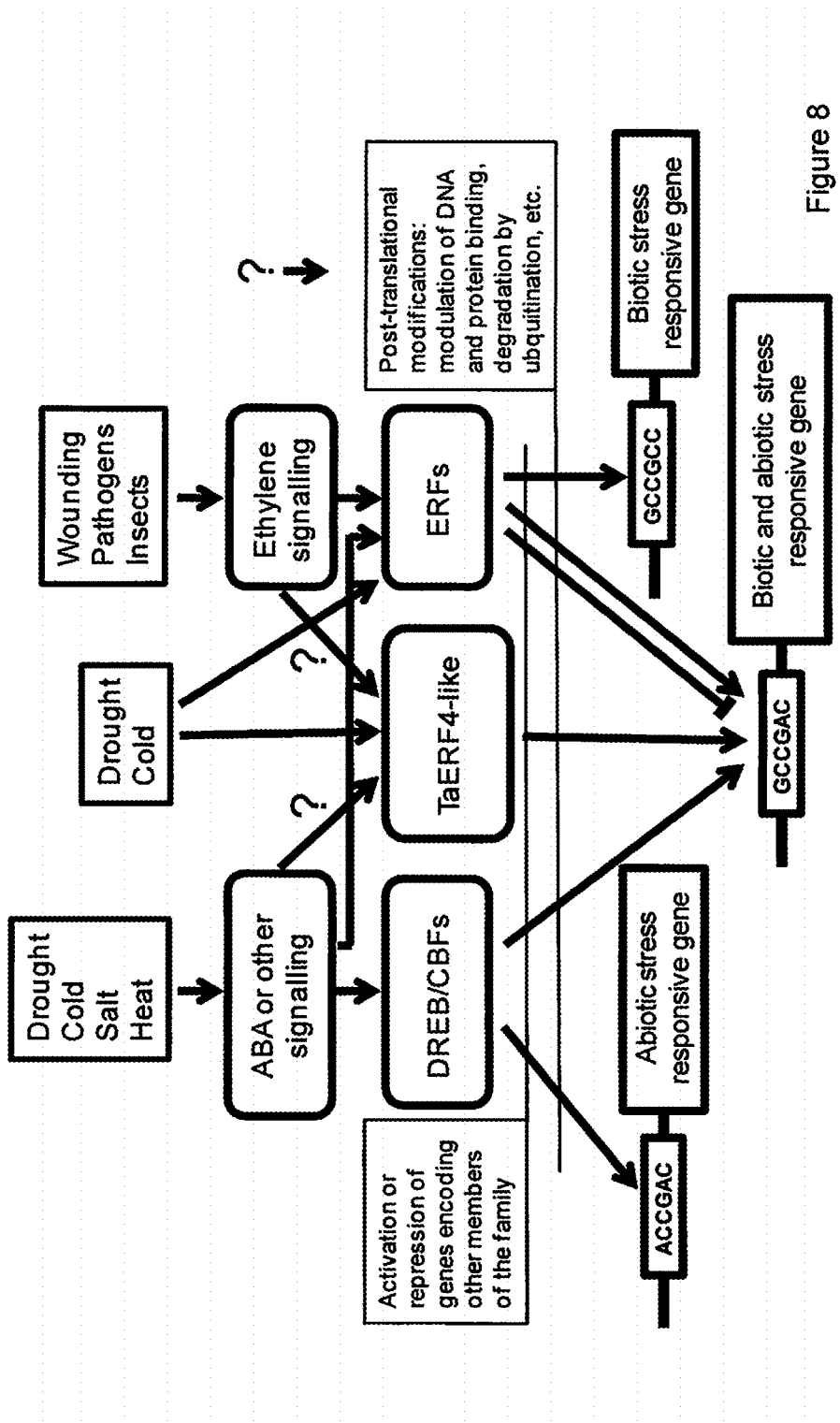

FIG. 8: Schematic representation of regulation of the abiotic and biotic stress-responsive genes by ERF and DREB/CBF TFs through three main types of stress-responsive cis-acting elements.

Figure 9:
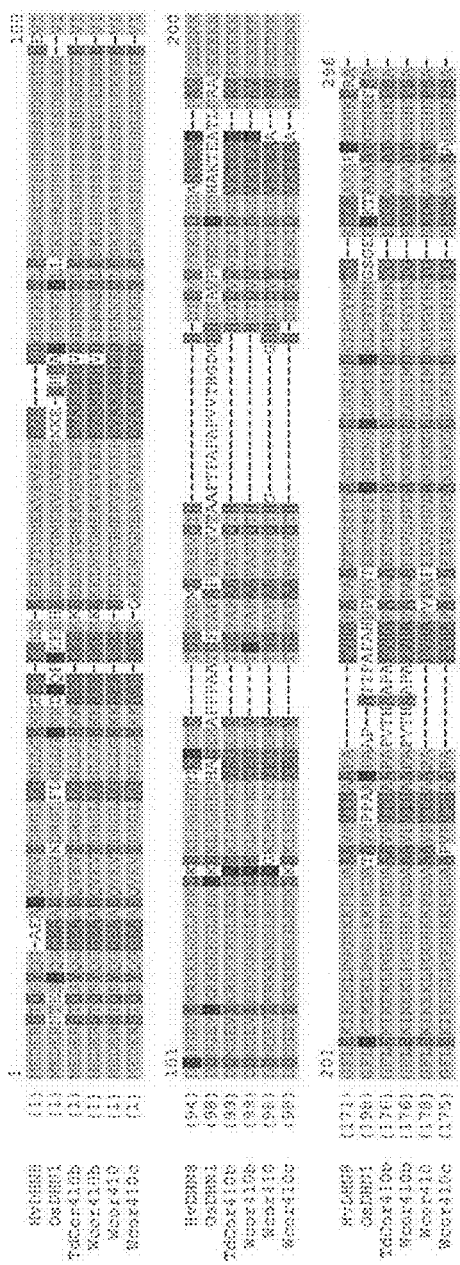

FIG. 9: Multiple sequence alignment of protein sequences of TdCor410b (SEQ ID NO: 3) and products of homoeologous genes from bread wheat and reported homologues from barley and rice: Wcor410 (Acc. AAA20189; SEQ ID NO:

63), Wcor410b (Acc. AAB18201; SEQ ID NO: 62), Wcor410c (Acc. AAB18202; SEQ ID NO: 64), HvDHN8 (Acc. AAD02259; SEQ ID NO: 60), OsDHN1 (Acc. AAV49032; SEQ ID NO: 61). Identical amino acid residues are in light gray boxes, conserved residues are in medium gray boxes, and similar residues are in dark gray boxes.

FIG. 10: The sequence of the TdCor410b promoter (SEQ ID NO: 36) with predicted CRT/DRE/LTREs. The putative TATA-box is in bold and underlined, the predicted elements are in grey boxes, the functional element is in a grey box and underlined. First by of each promoter deletion used in promoter mapping is marked with a black box. Names and sizes (bp) of promoter deletions are shown above the black boxes.

Figure 11:
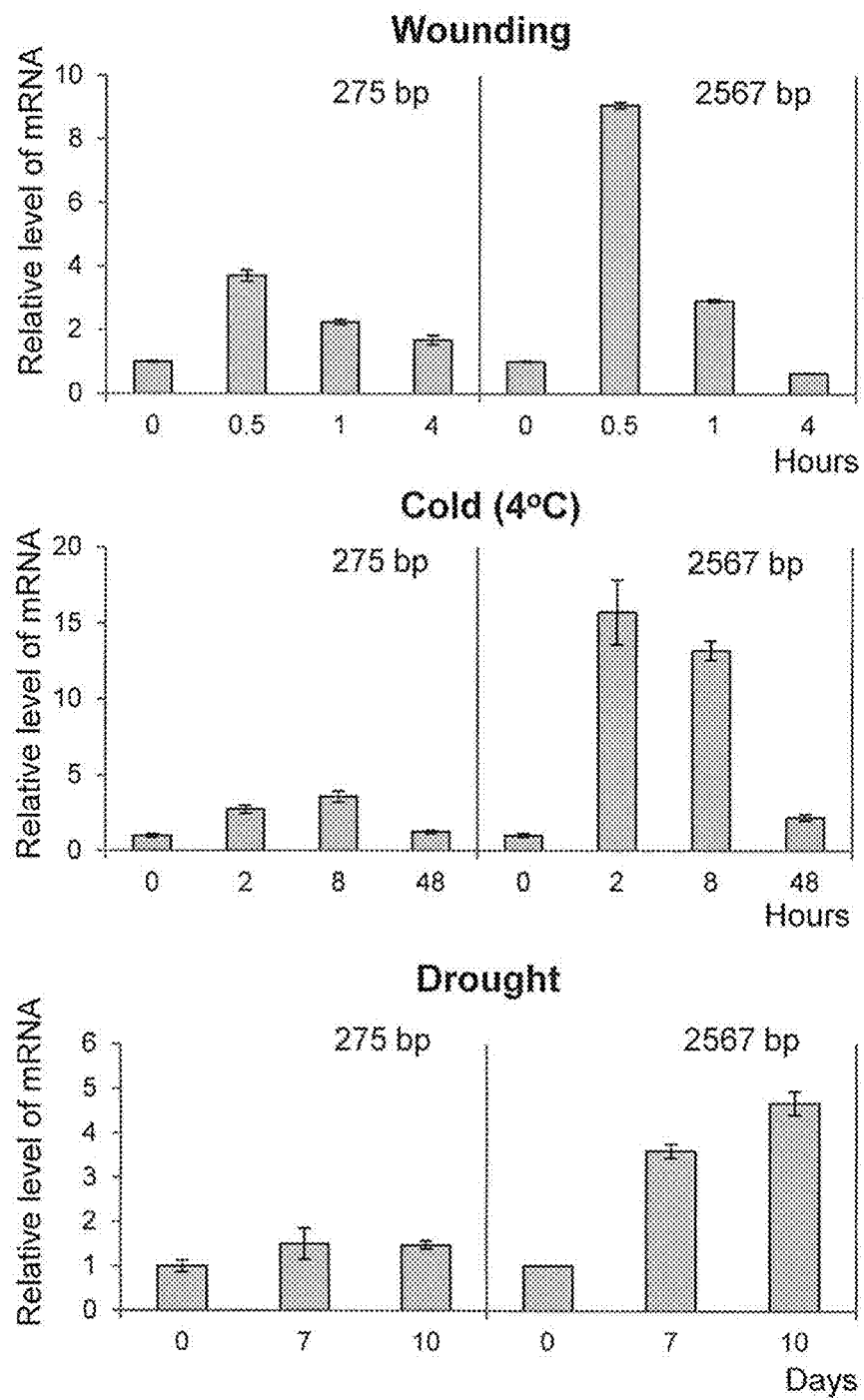

FIG. 11: Influence of point mutations in the functional CRT element on TdCor410b promoter activation demonstrated by transient expression assay. D7 denotes deletion of the CRT-containing element (positive control), D8 and M5 denote promoter deletions without the CRT element (negative controls), M1-M4 denote D7 deletion with single base pair substitutions to T.

Figure 12:
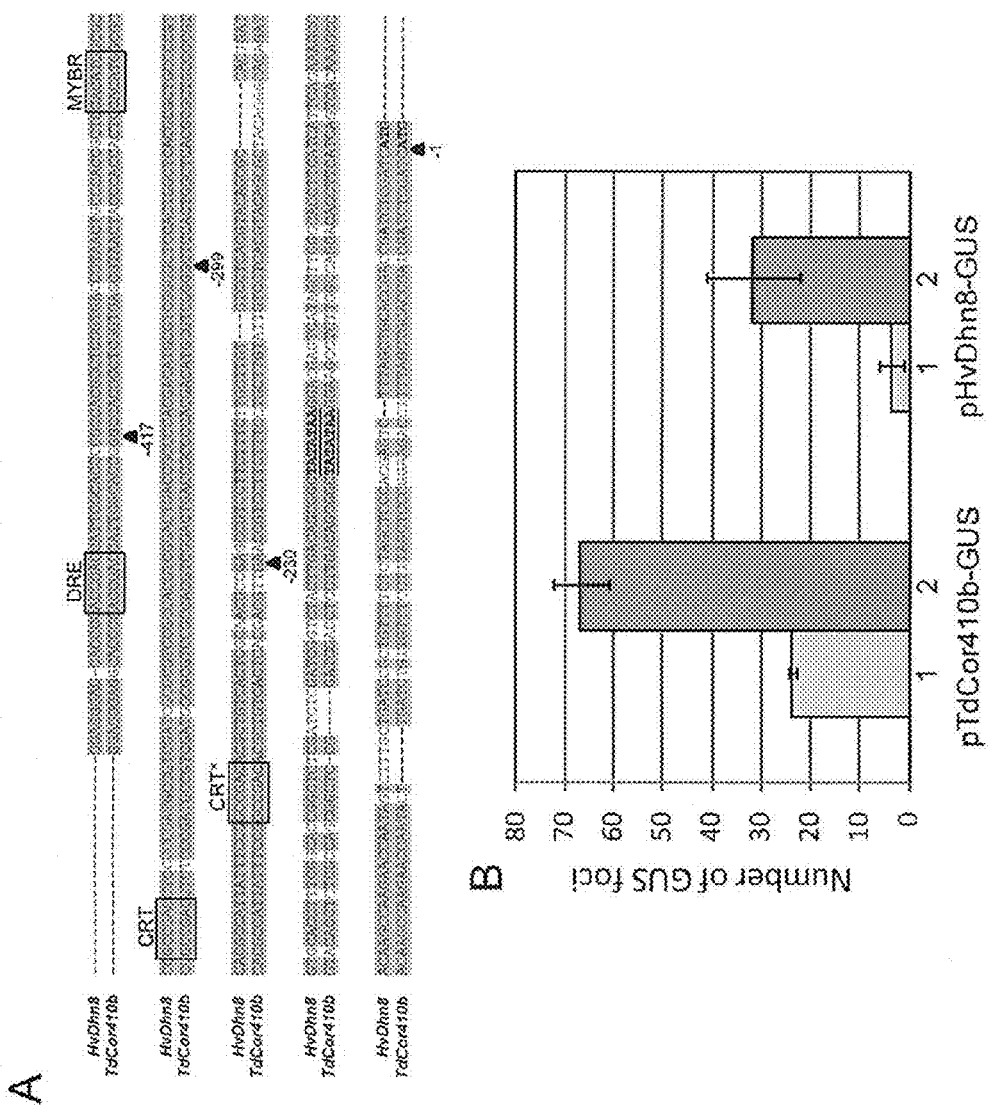

FIG. 12: (A) Pair-wise alignment of nucleotide sequences of the TdCor410b (SEQ ID NO: 37) and HvDHN8 (SEQ ID NO: 38) promoters. Computer-predicted cis-elements common for both promoters are in transparent boxes; sequence of the functional cis-element is encircled. The putative TATA-box and translational start are in grey boxes. (B) Basal activity of the TdCor410b and HvDhn8 promoters (Guo, et al., (2002) *Plant Mol Biol* 49:459-471) and activity induced by overexpression of TaDREB3 (Kizis and Pages, (2002) *Plant J* 30:679-689). The promoter-GUS construct was co-bombarded in the wheat suspension cell culture with either the pUbi-GFP (Guo, et al., (2002) *Plant Mol Biol* 49:459-471) or pUbi-TaDREB3 (Kizis and Pages, (2002) *Plant J* 30:679-689) constructs.

Figure 13:
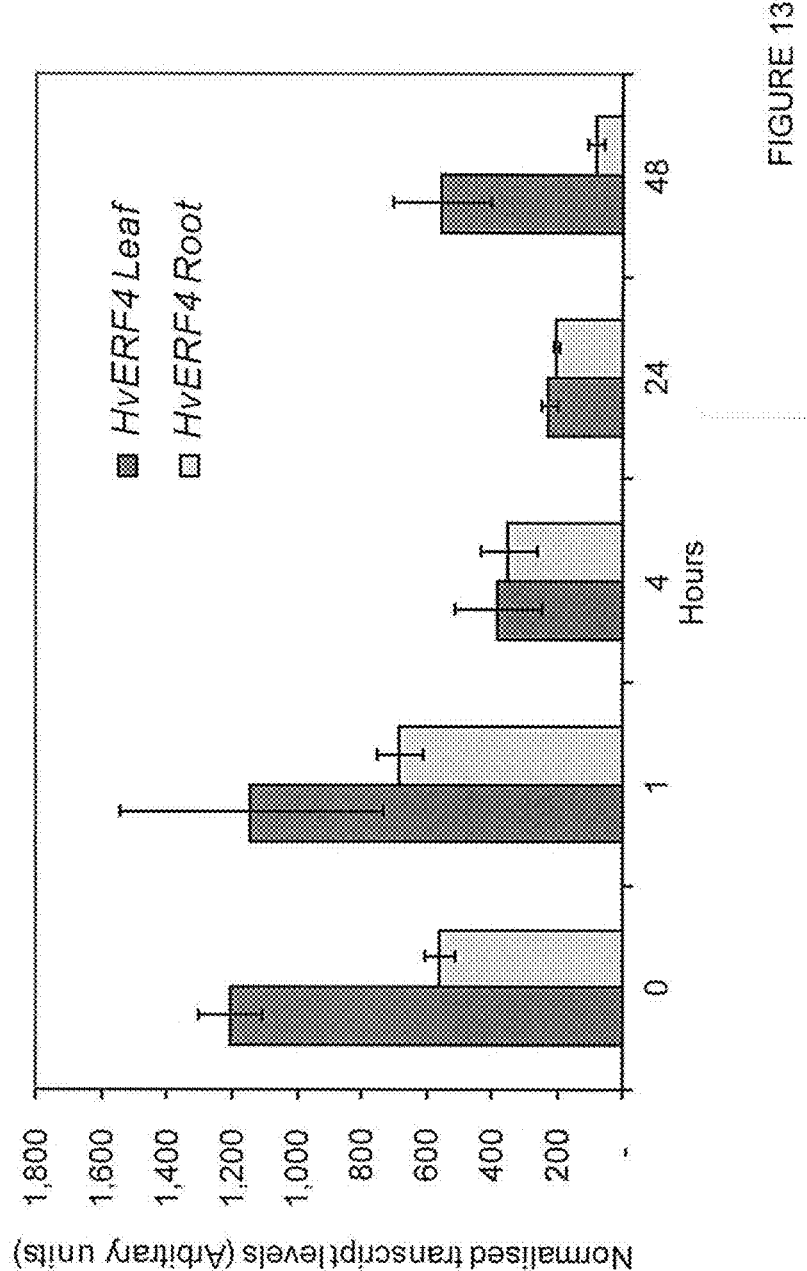

FIG. 13: The Q-PCR analysis of HvERF4 expression in leaves and roots of barley plants subjected to cold (4° C.).

FIG. 14: (A) A multiple sequence alignment of thirteen AP2 domains (top to bottom: SEQ ID NO: 65, 67, 69, 71, 73, 75, 77, 79, 81, 83, 85, 87, 89) of the ERF sequences using PROMALS3D (Ginalski, et al., (2003) *Nucleic Acids Res* 31:3804-3807). The positions of highly conserved Pro residues in the ERF sequences are highlighted in light gray and the positions of three Pro residues conserved in the selected cereal ERF sequences are highlighted in darker gray (B) The conserved regions of the COOH-terminal EAR sequence (top to bottom: SEQ ID NO: 66, 68, 70, 72, 74, 76, 78, 80, 82, 84, 86, 88, 90) underlying the importance of four conserved residues Asp, Leu, Asn and Pro, are highlighted.

SEQUENCE LISTING TABLE

| Sequence Name | SEQ ID NO |
|---|---|
| TaERF4a amino acid | 1 |
| TaERF4a cDNA | 2 |
| TdCor410b amino acid | 3 |
| TdCor410b | 4 |
| TaERF4b amino acid | 5 |
| TaERF4b cDNA | 6 |
| HvERF4 amino acid | 7 |
| HvERF4 cDNA | 8 |
| TaERF5a amino acid | 9 |
| TaERF5a cDNA | 10 |
| TaERF5b amino acid | 11 |
| TaERF5b cDNA | 12 |
| TaERF6 amino acid | 13 |
| TaERF6 cDNA | 14 |
| TdERF6 amino acid | 15 |
| TdERF6 cDNA | 16 |
| ZmERF5 amino acid | 17 |
| ZmERF5 cDNA | 18 |
| TdCor410b promoter | 19 |
| EAR motif | 20 |
| PKKPAGR region | 21 |
| DSAWR region | 22 |
| TaERF4a (FIG. 4 portion) | 23 |
| TaERF4a mut 1 (FIG. 4 portion) | 24 |
| TaERF4a mut 2 (FIG. 4 portion) | 25 |
| TaERF4a mut 1 + 2 (FIG. 4 portion) | 26 |
| EAR repression motif | 27 |
| Cis element | 28 |
| Recognition element + 10 | 29 |

DETAILED DESCRIPTION

Promoter of the stress-inducible gene TdCor410b was isolated and used for mapping of the functional DRE/CRT elements in transient expression assays. Activation of the truncated promoter containing the single functional CRT element by abiotic stresses and wounding was demonstrated, using stably transformed barley plants. Tandem repeats from the core of the identified functional CRT element, with and without adjacent nucleotide sequences, were used as baits in Y1H screens. TFs were isolated from cDNA libraries, which were prepared from the developing grain or whole spikes of unstressed or drought/cold stressed wheat and barley plants. These TFs were predominantly of the ERF family, and one of seven isolated factors belonged to the CBF/DREB class. Regulation of the TdCor410b promoter by some of the isolated TFs has been confirmed using transient expression assays. A series of 3D models of protein-DNA complexes were generated, which assisted explaining the specificity of the interactions between AP2 domains and the GCCGAC, ACCGAC and GCCGCC core elements. The results of the transient expression assays and analyses of spatial and stress-inducible expression of the isolated ERFs show that TaERF4a is suitable candidate for the regulation of Wcor410 during plant development and under drought stress. Some of the isolated ERF genes can also be involved in regulation of the Wcor410 gene under cold stress. One of the six isolated TFs, TaERF6, is a candidate for wound inducible activation of Wcor410b. One functional cis-acting element, the core of which is GCCGAC and which is situated within the –299 and –230 bp promoter region, was identified using transient activation by TaDREB3. Ten potential DRE/CRT/LTR elements were predicted in the TdCor410b promoter. Interaction with TaDREB3 was demonstrated with the CRT element closest to the potential TATA-box. Basal activity of the TdCor410b promoter was mapped to the same –299 bp fragment of the promoter, indicating that the same cis-element may be responsible for both constitutive and inducible activation of the TdCor410b promoter (FIG. 1A).

Furthermore, comparison of sequences of the TdCor410b and HvDhn8 promoters revealed high conservation of the position of the GCCGAC elements and of the adjacent sequences in both promoters (FIG. 12).

Barley plants were stably transformed with TaDREB3 under regulation of the 2,567 bp and 275 bp regions of the TdCor410b promoter. Analysis of transgenic lines demonstrated that, both promoter regions had basal expression levels and were activated by cold, drought and wounding (FIG. 1B). Results confirmed the role of the CRT element proximal to the TATA box as an universal element, which could regulate TdCor410b promoter activity during plant development under optimal growth conditions and under a variety of stresses.

To better understand the mechanism of promoter activation through the single cis-element, TFs which were able to bind and potentially regulate expression through the CRT element were isolated. The GCCGAC element (CRT1) was used as bait in the Y1H screens of cDNA libraries that were prepared from either unstressed or stressed wheat and barley tissues with the aims of 1) finding if any other DREBs/CBFs will bind the mapped DRE/CRT and 2) identifying TFs which would be responsible for promoter activation in the absence of stress (basal TdCor410b promoter activity). To determine the influence of adjacent sequences on the binding specificity of the core element, the extended core sequence, with 10 adjacent bp, was also used in a Y1H screen as bait (CRT2). Seven different AP2 domain-containing TFs were isolated in the screen with these core elements as baits (FIG. 2A). Surprisingly, TaDREB2 belonged to the DREB subfamily. The other six TFs belonged to the subfamily of ethylene responsive members of the AP2 domain family. Surprisingly, only two types of ERFs were able to bind the GCC-box and neither of the ERFs interacted with the ACCGAC element (FIG. 2B). No difference in specificity of binding to CRT1 or CRT2 was detected for any of the isolated TFs, suggesting that no involvement of sequences adjacent to the core element took place. The functionality of such interactions was confirmed by demonstration of the ability of TaERF4a to activate the TdCor410b promoter in transient expression assays (FIG. 2C). In contrast to TaERF4a, two other types of ERFs, TaERF5a and TaERF6, did not activate the TdCor410b promoter (FIG. 2D). However, substitution of the CRT element for a three-fold repeat of GCC-box in the same promoter led to activation; weak activation by TaERF4a, strong by TaERF5a and moderate by TaERF6). All three ERFs behaved as activators in an auto-activation test in yeast (FIG. 2C).

The most abundant among the independent clones isolated in the Y1H screen were clones which encoded sequences of the close homologues TaERF4a, TaERF4b and HvERF4. All three TFs belong to the same subfamily of ERF factors that had some structural and sequence homologies to AtERF3 and AtERF4 from *Arabidopsis* (FIG. 2A; FIG. 14). Products of all these genes contain a C-terminal EAR repression motif [(L/F)DLN(L/F)(X)P (SEQ ID NO: 27) ERF-associated amphiphilic repression] (FIG. 14B). ERF repressors display differential expression patterns in plant tissues and some are shown to be induced by hormones, ethylene, jasmonate and ABA, and by abiotic and biotic stresses. However, in contrast to TaERF4a, TaERF4b and HvERF4, repressors from tobacco and Arabidosis that contain Arg42 instead of Pro42 in the AP2 domain were shown to strongly interact with the GCC-box. Alignment and conservation analysis of more than 500 ERFs from databases revealed that Pro42 can only be found within ERFs of monocotyledonous plants. It was demonstrated that Pro42 changed the specificity of protein-DNA binding.

TaERF4a and TaCor410b expression displayed a strong correlation in all tested wheat tissues and under drought, indicating that TaERF4a functions as a specific regulator of the TdCor410b promoter. TaERF4a, a potential repressor, behaved as a transcription activator in yeast and in transient expression assays with wheat cell culture (FIGS. 2C and 2D). EAR motif of TaERF4a was required in activation of the TdCor410b promoter. The substitution of four key amino acid residues in the EAR motif for alanine residues strongly decreased the promoter activation properties of TaERF4a in both Y2H and transient expression assays (FIG. 2D). The DNA binding specificity of TaERF4a-like TFs indicated selective regulation of genes, which are activated by both biotic and abiotic stresses through the 'promiscuous' GCCGAC element, while genes that are specifically induced by wounding and pathogens through the GCC-box, seemed to be excluded from the influence of TaERF4a, as they were unable to bind the GCC-box (FIG. 8).

The 3D models of the AP2 domains of TaERF5a, TaERF4a and TaDREB3 were constructed using spatial restraints from the in-solution structure of the DNA-binding domain of AtERF1 solved by NMR in complex with the 5'-GCTAGCCGCCAGC cis-element (SEQ ID NO: 28). The 1gcc:A structure from *Arabidopsis* was identified as a suitable template for molecular modeling by several prediction servers that are listed herein. Based on the data from molecular modeling it could be concluded that the mutual interplay of residues, within the secondary structure elements of the AP2 domains that form a β-sheet secondary structure, could impact structural rigidity or flexibility of AP2 domains. This structural property of the AP2 domains of ERFs or DREBs could in turn impact DNA binding selectivity. Further, overall shape variability and disparity in surface electrostatic potentials exist among individual AP2 domains of ERFs and DREBs, which could contribute to differences in binding selectivity of cis-elements.

Attempts to restore the ability of TaERF4a to bind the GCCGCC cis-element, through molecular modeling and site-directed mutagenesis, (FIG. 4B) needs to be discussed in connection with recent molecular dynamics simulation (Wang, et al., (2009) *J. Mol. Recognit.* 22:474-479). Wang, et al., (2009) reported that the significance of the Arg150, Arg152, Arg170 and Trp172 residues in the AP2 of AtERF1 for binding the GCC-box differs between AtERF1, C-repeat/dehydration-responsive element binding factor 1 (Lee, et al., (2004) *Plant Mol. Biol.* 55:61-81) and AtERF4. From the Arg150, Arg152, Arg170 and Trp172 residues that are iso-positional to Arg23, Arg25, Pro42 and Trp44 in AP2 of TaERF4a, only the two highly conserved residues Arg23 and Arg25 directly contact the first G in GCCGAC in the coding strand and two GG bases in the complementary strand GTCGGC. The two latter residues thus provide primary DNA binding capacity for the GCCGAC/GTCGGC cis-element. In the AP2 domain of TaERF4a, Pro42 is not interacting with either of the base pairs of GCCGAC, and thus if this residue were mutated to Arg, the variant form of AP2 could potentially bind base C of GCCGCC, which was achieved in the current work. ERF binding domains that mediate contacts with DNA bases or their phosphate backbones, share common features. These features thus indicate that DNA binding properties and specificity could be modified.

In summary, the structural comparisons of molecular models of the AP2 domains of TaERFs and TaDREBs in complex with cis-elements highlighted the fact that, the specific variations of amino acid residues, which affect flexibility of secondary structure β-sheet elements, influence properties of protein structures and lead to differences in recognition selectivity of cis-elements. As a consequence, these differences could impact upon selectivity of binding of individual cis-elements by TaERFs or TaDREB binding domains. Variant TaERF and TaDREB AP2 domains are created through site-directed mutagenesis and plant transformation.

Wcor410 genes are most likely regulated by members of at least several families of ERFs and DREB/CBFs through a single GCCGAC element. The stress responsive induction of TdCor410b demonstrated a complex interplay of different ERFs and/or DREB/CBFs with possible participation of other TFs and other modifying factors (FIG. 8). A suitable gene for the constitutive (developmental) and drought-inducible up-regulation of TdCor410b expression is TaERF4a. This TF possessed properties that were atypical of ERFs such as unusual DNA-binding specificity and behavior as a transcriptional activator, even though it contained the EAR motif known to be associated with transcriptional repressors. Potential modifications of the TdCor410b promoter may be successfully used in transgenic applications. For example, the specificity of the promoter could be changed by substitution of CRT for the GCC-box. These substitutions abolished activation of TaERF4a-like TFs and improved activation of other tested wheat ERF TFs. Substitution of the GCCGAC element with ACCGAC would likely eradicate, or at least strongly decrease, the binding of the ERF factors and increase the binding of the DREB/CBF factors, which are usually in low abundance in the absence of stress.

The terms "monocot" and "monocotyledonous plant" are used interchangeably herein. A monocot of the current disclosure includes the *Gramineae*.

The terms "dicot" and "dicotyledonous plant" are used interchangeably herein. A dicot of the current disclosure includes the following families: Brassicaceae, Leguminosae and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"*Arabidopsis*" and "*Arabidopsis thaliana*" are used interchangeably herein, unless otherwise indicated.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence" and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

Nitrogen utilization efficiency (NUE) genes affect yield and have utility for improving the use of nitrogen in crop plants, especially maize. Increased nitrogen use efficiency can result from enhanced uptake and assimilation of nitrogen fertilizer and/or the subsequent remobilization and reutilization of accumulated nitrogen reserves, as well as increased tolerance of plants to stress situations such as low nitrogen environments. The genes can be used to alter the genetic composition of the plants, rendering them more productive with current fertilizer application standards or maintaining their productive rates with significantly reduced fertilizer or reduced nitrogen availability. Improving NUE in corn would increase corn harvestable yield per unit of input nitrogen fertilizer, both in developing nations where access to nitrogen fertilizer is limited and in developed nations where the level of nitrogen use remains high. Nitrogen utilization improvement also allows decreases in on-farm input costs, decreased use and dependence on the non-renewable energy sources required for nitrogen fertilizer production and reduces the environmental impact of nitrogen fertilizer manufacturing and agricultural use "Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability or translation of the associated coding sequence. Regulatory sequences may include, but are not limited to, promoters, translation leader sequences, introns and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The percent identity between two amino acid or nucleic acid sequences may be determined by visual inspection and mathematical calculation.

Sequence alignments and percent identity calculations may be determined using a variety of comparison methods designed to detect homologous sequences including, but not limited to, the MEGALIGN® program of the LASER- GENE® bioinformatics computing suite (DNASTAR® Inc., Madison, Wis.). Unless stated otherwise, multiple alignment of the sequences provided herein were performed using the Clustal W method of alignment (Thompson, et al., (1994). *Nucleic Acids Research* 22:4673-80) with the default parameters (GAP PENALTY=10, GAP LENGTH PENALTY=0.2, DELAY DEVERGENT SEQS(%)=30%, DNA TRANSITION WEIGHT=0.5, PROTEIN WEIGHT MATRIX "Gonnet Series"). Default parameters for pairwise alignments using the Clustal W method were SLOW-ACCURATE, GAP PENALTY=10, GAP LENGTH=0.10, PROTEIN WEIGHT MATRIX "Gonnet 250". After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner.

Alternatively, sequence alignments and percent identity calculations may be determined using a variety of comparison methods designed to detect homologous sequences including, but not limited to, the Clustal V method of alignment (Higgins and Sharp (1989) CABIOS. 5:151 153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Alternatively, the percent identity of two protein sequences may be determined by comparing sequence information based on the algorithm of Needleman and Wunsch, (*J. Mol. Biol.* 48:443-453 1970) and using the GAP computer program available from the University of Wisconsin Genetics Computer Group (UWGCG). The preferred default parameters for the GAP program include: (1) a scoring matrix, blosum62, as described by Henikoff and Henikoff, (*Proc. Natl. Acad. Sci. USA* 89:10915-10919 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul, et al., (*Nucl. Acids. Res.* 25:3389-3402 1997). This program is available on the Internet at the web site of the National Center for Biotechnology Information (NCBI) or the DNA Data Bank of Japan (DDBJ). The details of various conditions (parameters) for identity search using the BLAST program are shown on these web sites and default values are commonly used for search although part of the settings may be changed as appropriate. Alternatively, the percent identity of two amino acid sequences may be determined by using a program such as genetic information processing software GENETYX Ver.7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG®; Madison, Wis.) WISCONSIN PACKAGE® version 10.0 program, "GAP" (Devereux, et al., (1984) *Nucl. Acids Res.* 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG® implementation of a unary comparison matrix (containing a value of 1 for identities and 0 for non-identities) for nucleotides, and the weighted amino acid comparison matrix of Gribskov and Burgess, (1986) *Nucl. Acids Res.* 14:6745, as described by Schwartz and Dayhoff, eds., "Atlas of Polypeptide Sequence and Structure," National Biomedical Research Foundation, pp. 353-358 (1979) or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps and (4) no maximum penalty for long gaps. Other programs used by those skilled in the art of sequence comparison can also be used, such as, for example, the BLASTN program version 2.2.7, available for use via the National Library of Medicine website, or the WU-BLAST 2.0 algorithm (Advanced Biocomputing, LLC). In addition, the BLAST algorithm uses the BLOSUM62 amino acid scoring matrix and optional parameters that can be used are as follows: (A) inclusion of a filter to mask segments of the query sequence that have low compositional complexity (as determined by the SEG program of Wootton and Federhen (Computers and Chemistry, 1993); also see, Wootton and Federhen, (1996) *Methods Enzymol.* 266:5545-71) or segments consisting of short-periodicity internal repeats (as determined by the XNU program of Claverie and States (Computers and Chemistry, 1993)) and (B) a statistical significance threshold for reporting matches against database sequences or E-score (the expected probability of matches being found merely by chance, according to the stochastic model of Karlin and Altschul, (1990); if the statistical significance ascribed to a match is greater than this E-score threshold, the match will not be reported); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75 or 1e-100.

Standard recombinant DNA and molecular cloning techniques used herein are well known in the art and are described more fully in Sambrook, et al., *Molecular Cloning: A Laboratory Manual*; Cold Spring Harbor Laboratory Press: Cold Spring Harbor, 1989 (hereinafter "Sambrook").

The term "consisting essentially of" in the context of a polypeptide sequence generally refers to the specified portion of the amino acid sequence and those other sequences that do not materially affect the basic and novel characteristics of the disclosed sequences herein. For example, in the context of the polypeptide sequences disclosed herein, the term consisting essentially generally refers to that portion of the polypeptide sequence (e.g., ERF4a) and those other polypeptide sequences that do not materially affect the transcriptional activation functions described herein. Optionally, the expression of the polypeptide sequences increase drought tolerance and/or grain yield.

Embodiments include isolated polynucleotides and polypeptides, recombinant DNA constructs useful for conferring drought tolerance, compositions (such as plants or seeds) that include these recombinant DNA constructs, and methods utilizing these recombinant DNA constructs.

Isolated Polynucleotides and Polypeptides:

The present disclosure includes the following isolated polynucleotides and polypeptides:

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 1, 3, 5, 7, 9, 11, 13, 15 and 17. The polypeptide is preferably an ERF4a polypeptide.

An isolated polypeptide wherein the amino acid sequence is a sequence selected from the group consisting of SEQ ID NOS: 1, 3, 5, 7, 9, 11, 13, 15 and 17; by alteration of one or more amino acids by at least one method selected from the group consisting of: deletion, substitution, addition and insertion and (c) a polypeptide wherein the amino acid sequence of the polypeptide comprises a sequence selected from the group consisting of SEQ ID NOS: 1, 3, 5, 7, 9, 11, 13, 15 and 17. The polypeptide is preferably a ERF4a polypeptide.

An isolated polynucleotide comprising a nucleotide sequence encoding a polypeptide with e.g., drought tolerance and/or increased nitrogen use efficiency, wherein the nucleotide sequence is hybridizable under stringent conditions with a DNA molecule comprising the full complement of a sequence selected from the group consisting of SEQ ID NOS: 1, 3, 5, 7, 9, 11, 13, 15 and 17.

An isolated polynucleotide comprising a nucleotide sequence encoding a polypeptide with e.g., drought tolerance and/or increased nitrogen use efficiency, wherein the nucleotide sequence is a sequence selected from the group consisting of SEQ ID NOS: 1, 3, 5, 7, 9, 11, 13, 15 and 17; and those polynucleotides comprising alteration of one or more nucleotides by at least one method selected from the group consisting of: deletion, substitution, addition and insertion.

Recombinant DNA Constructs:

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 1, 3, 5, 7, 9, 11, 13, 15 and 17; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes an ERF4a polypeptide. The ERF4a polypeptide may be from *Arabidopsis thaliana*, *Zea mays*, *Sorghum bicolor*, *Oryza sativa*, *Medicago truncatula*, *Hordeum vulgare*, *Triticum aestivum*, *Triticum durum*, *Glycine max*, *Glycine tabacina*, *Glycine soja* and *Glycine tomentella*, *Camelina*.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as *glycine*, or a more hydrophobic residue, such as valine, leucine or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The protein of the current disclosure may also be a protein which comprises an amino acid sequence comprising deletion, substitution, insertion and/or addition of one or more amino acids in an amino acid sequence selected from the group consisting of SEQ ID NOS: 1, 3, 5, 7, 9, 11, 13, 15 and 17. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., *Nucleic Acid Research* 10(20):6487-6500 (1982), which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen and those in which a gene is selectively cleaved to remove, substitute, insert or add a selected nucleotide or nucleotides and then ligated.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook, et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling and detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

The protein of the present disclosure is preferably a protein with e.g., drought tolerance and/or increased nitrogen use efficiency.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "increasing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

Genome editing or genome engineering through site-directed mutagenesis by custom meganucleases with unique DNA-recognition and cleavage properties is possible (e.g., WO 2007/047859 and WO 2009/114321). This technique provides the ability to specifically modify a defined target of interest within a genome, e.g., ERF4a genomic region. Another site-directed engineering is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. These citations are incorporated herein to the extent they relate to materials and methods to enable genome editing through site-specific modification.

Regulatory Sequences:

A recombinant DNA construct of the present disclosure may comprise at least one regulatory sequence. A regulatory sequence may be a promoter.

A number of promoters can be used in recombinant DNA constructs of the present disclosure. The promoters can be selected based on the desired outcome and may include constitutive, tissue-specific, inducible or other promoters for expression in the host organism.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga, et al., (1999) *Nature Biotechnol.* 17:287-91).

Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611. Diurnal promoters disclosed in U.S. patent Ser. No. 12/985,413 filed Jan. 6, 2011 are incorporated herein by reference.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, (1989) *Plant Cell* 1:1079-1093), patatin (potato tubers) (Rocha-Sosa, et al., (1989) *EMBO J.* 8:23-29), convicilin, vicilin, and legumin (pea cotyledons) (Rerie, et al., (1991) *Mol. Gen. Genet.* 259:149-157; Newbigin, et al., (1990) *Planta* 180:461-470; Higgins, et al., (1988) *Plant. Mol. Biol.* 11:683-695), zein (maize endosperm) (Schemthaner, et al., (1988) *EMBO J.* 7:1249-1255), phaseolin (bean cotyledon) (Segupta-Gopalan, et al., (1985) *Proc. Natl. Acad. Sci. U.S.A.* 82:3320-3324), phytohemagglutinin (bean cotyledon) (Voelker, et al., (1987) *EMBO J.* 6:3571-3577), B-conglycinin and glycinin (soybean cotyledon) (Chen, et al., (1988) *EMBO J.* 7:297-302), glutelin (rice endosperm), hordein (barley endosperm) (Marris, et al., (1988) *Plant Mol. Biol.* 10:359-366), glutenin and gliadin (wheat endosperm) (Colot, et al., (1987) *EMBO J.* 6:3559-3564) and sporamin (sweet potato tuberous root) (Hattori, et al., (1990) *Plant Mol. Biol.* 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderckhove, et al., (1989) *Bio/Technology* 7:L929-932), bean lectin and bean beta-phaseolin promoters to express luciferase (Riggs, et al., (1989) *Plant Sci.* 63:47-57) and wheat glutenin promoters to express chloramphenicol acetyl transferase (Colot, et al., (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical and/or developmental signals. Inducible or regulated promoters include, for example, promoters regulated by light, heat, stress, flooding or drought, phytohormones, wounding or chemicals such as ethanol, jasmonate, salicylic acid or safeners.

Promoters for use in the current disclosure include the following: 1) the stress-inducible RD29A promoter (Kasuga, et al., (1999) *Nature Biotechnol.* 17:287-91); 2) the barley promoter, B22E; expression of B22E is specific to the pedicel in developing maize kernels (Klemsdal, et al., (1991) *Mol. Gen. Genet.* 228(1/2):9-16) and 3) maize promoter, Zag2 (Schmidt, et al., (1993) *Plant Cell* 5(7):729-737; Theissen, et al., (1995) *Gene* 156(2):155-166; NCBI GenBank Accession Number X80206)). Zag2 transcripts can be detected 5 days prior to pollination to 7 to 8 days after pollination ("DAP") and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional promoters for regulating the expression of the nucleotide sequences of the present disclosure in plants are stalk-specific promoters. Such stalk-specific promoters include the alfalfa S2A promoter (GenBank Accession Number EF030816; Abrahams, et al., (1995) *Plant Mol. Biol.* 27:513-528) and S2B promoter (GenBank Accession Number EF030817) and the like, herein incorporated by reference.

Promoters may be derived in their entirety from a native gene, or be composed of different elements derived from different promoters found in nature, or even comprise synthetic DNA segments.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank Accession Number EF030816) and S2B (Genbank Accession Number EF030817) and the constitutive promoter GOS2 from *Zea mays*. Other promoters include root preferred promoters, such as the maize NAS2 promoter, the maize Cyclo promoter (U.S. Pat. No. 7,268,226), the maize ROOTMET2 promoter (WO 2005/063998, published Jul. 14, 2005), the CR1B10 promoter (WO2006/055487, published May 26, 2006), the CRWAQ81 (WO 2005/035770, published Apr. 21, 2005) and the maize ZRP2.47 promoter (NCBI Accession Number: U38790; GI Number 1063664), Recombinant DNA constructs of the present disclosure may also include other regulatory sequences, including but not limited to, translation leader sequences, introns and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) *Mol. Cell Biol.* 8:4395-4405; Callis, et al., (1987) *Genes Dev.* 1:1183-1200.

Any plant can be selected for the identification of regulatory sequences and polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, *eucalyptus*, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, *papaya*, parsley, parsnip, pea, peach, peanut, pear, pepper, persimmon, pine, pineapple, plantain, plum, pomegranate, poplar, potato, pumpkin, quince, *radiata* pine, radicchio, radish, rapeseed, raspberry, rice, rye, *sorghum*, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams and zucchini.

Compositions:

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature inbred transgenic plants, can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions) or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize, rice or soybean plant, such as a maize hybrid plant or a maize inbred plant. The plant may also be sunflower, *sorghum*, canola, wheat, alfalfa, cotton, barley, millet, sugarcane, switchgrass, tobacco, potato or sugar beet.

"Drought" refers to a decrease in water availability to a plant that, especially when prolonged, can cause damage to the plant or prevent its successful growth (e.g., limiting plant growth or seed yield).

"Drought tolerance" is a trait of a plant which contributes to its ability to survive under drought conditions over prolonged periods of time without exhibiting substantial physiological or physical deterioration.

"Increased drought tolerance" of a plant is measured relative to a reference or control plant and is a trait of the plant which contributes to its ability to survive under drought conditions over prolonged periods of time, without exhibiting the same degree of physiological or physical deterioration relative to the reference or control plant grown under similar drought conditions. Typically, when a transgenic plant comprising a recombinant DNA construct in its genome exhibits increased drought tolerance relative to a reference or control plant, the reference or control plant does not comprise in its genome the recombinant DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic—acute2" is a measure of the percent change in total area determined by remote visible spectrum imaging between the first day of chronic stress and the day of the second acute stress The variable "% area chg_start chronic—end chronic" is a measure of the percent change in total area determined by remote visible spectrum imaging between the first day of chronic stress and the last day of chronic stress.

The variable "% area chg_start chronic—harvest" is a measure of the percent change in total area determined by remote visible spectrum imaging between the first day of chronic stress and the day of harvest.

The variable "% area chg_start chronic—recovery24 hr" is a measure of the percent change in total area determined by remote visible spectrum imaging between the first day of chronic stress and 24 hrs into the recovery (24 hrs after acute stress 2).

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress—(variable fluorescence difference between the maximum and minimum fluorescence/maximum fluorescence).

The variable "fv/fm_acute2" is a measure of the optimum quantum yield (Fv/Fm) at the end of the second acute stress—(variable flourescence difference between the maximum and minimum fluorescence/maximum fluorescence).

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area over a single day ($Y(t)=Y0*e^{r*t}$). $Y(t)=Y0*e^{r*t}$ is equivalent to % change in $Y/\Delta t$ where the individual terms are as follows: $Y(t)$=Total surface area at t; $Y0$=Initial total surface area (estimated); r=Specific Growth Rate day$^{-1}$, and t=Days After Planting ("DAP").

The variable "shoot dry weight" is a measure of the shoot weight 96 hours after being placed into a 104° C. oven.

The variable "shoot fresh weight" is a measure of the shoot weight immediately after being cut from the plant.

The Examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% yield) in field testing under simulated or naturally-occurring drought conditions (e.g., by measuring for substantially equivalent yield under drought conditions compared to non-drought conditions, or by measuring for less yield loss under drought conditions compared to a control or reference plant).

One of ordinary skill in the art would readily recognize a suitable control or reference plant to be utilized when assessing or measuring an agronomic characteristic or phenotype of a transgenic plant in any embodiment of the present disclosure in which a control plant is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99% or 100% sequence identity of nuclear genetic material compared to the plant comprising the recombinant DNA construct. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s) and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods:

Methods include but are not limited to methods for increasing drought tolerance in a plant, methods for evaluating drought tolerance in a plant, methods for altering an agronomic characteristic in a plant, methods for determining an alteration of an agronomic characteristic in a plant and methods for producing seed. The plant may be a monocotyledonous or dicotyledonous plant, for example, a maize, rice or soybean plant. The plant may also be sunflower, sorghum, canola, wheat, alfalfa, cotton, barley or millet. The seed may be a maize, rice or soybean seed, for example, a maize hybrid seed or maize inbred seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell or prokaryotic, e.g., a bacterial cell.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory sequence and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure and (b) growing the transformed host cell under conditions that are suitable for expression of the recombinant DNA construct wherein expression of the recombinant DNA construct results in production of altered levels of the polypeptide of the disclosure in the transformed host cell.

A method of increasing drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 1, 3, 5, 7, 9, 11, 13, 15 and 17 and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of increasing drought tolerance in a plant, comprising: (a) introducing into a regenerable plant cell a recombinant DNA construct comprising a polynucleotide operably linked to at least one regulatory element, wherein said polynucleotide comprises a nucleotide sequence encoding a polypeptide with e.g., drought tolerance and/or increased nitrogen use efficiency, wherein the nucleotide sequence is: (a) hybridizable under stringent conditions with a DNA molecule comprising the full complement of a sequence selected from the group consisting of SEQ ID NOS: 2, 4, 6, 8, 10, 12, 14, 16 and 18 or (b) a sequence selected from the group consisting of SEQ ID NOS: 2, 4, 6, 8, 10, 12, 14, 16 and 18; by alteration of one or more nucleotides by at least one method selected from the group consisting of: deletion, substitution, addition and insertion and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

A method of evaluating drought tolerance in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 1, 3, 5, 7, 9, 11, 13, 15 and 17; (b) obtaining a progeny plant derived from said transgenic plant, wherein the progeny plant comprises in its genome the recombinant DNA construct and (c) evaluating the progeny plant for drought tolerance compared to a control plant not comprising the recombinant DNA construct.

A method of evaluating drought tolerance in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with e.g., drought tolerance and/or increased nitrogen use efficiency, wherein the nucleotide sequence is: (a) hybridizable under stringent conditions with a DNA molecule comprising the full complement of a sequence selected from the group consisting of SEQ ID NOS: 2, 4, 6, 8, 10, 12, 14, 16 and 18 or (b) a sequence selected from the group consisting of SEQ ID NOS: 2, 4, 6, 8, 10, 12, 14, 16 and 18; by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct and (c) evaluating the progeny plant for drought tolerance compared to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 81%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal W method of alignment, when compared to a sequence selected from the group consisting of SEQ ID NOS: 1, 3, 5, 7, 9, 11, 13, 15 and 17; (b) obtaining a progeny plant derived from said transgenic plant, wherein the progeny plant comprises in its genome the recombinant DNA construct and (c) determining whether the progeny plant exhibits an alteration in at least one agronomic characteristic when compared, optionally under water limiting conditions, to a control plant not comprising the recombinant DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory element, wherein said polynucleotide comprises a nucleotide sequence encoding a polypeptide with e.g., drought tolerance and/or increased nitrogen use efficiency, wherein the nucleotide sequence is: (a) hybridizable under stringent conditions with a DNA molecule comprising the full complement of a sequence selected from the group consisting of SEQ ID NOS: 2, 4, 6, 8, 10, 12, 14, 16 and 18 or (b) a sequence selected from the group consisting of SEQ ID NOS: 2, 4, 6, 8, 10, 12, 14, 16 and 18; by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct and (c) determining whether the progeny plant exhibits an alteration in at least one agronomic characteristic when compared, optionally under water limiting conditions, to a control plant not comprising the recombinant DNA construct.

A method of producing seed (for example, seed that can be sold as a drought tolerant product offering) comprising any of the preceding methods, and further comprising obtaining seeds from said progeny plant, wherein said seeds comprise in their genome said recombinant DNA construct.

In any of the preceding methods or any other embodiments of methods of the present disclosure, in said introducing step said regenerable plant cell may comprise a callus cell, an embryogenic callus cell, a gametic cell, a meristematic cell or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone and (iii) subculturing said transformed plant cells after step (ii) onto a second media, to allow for shoot elongation, root development or both.

In any of the preceding methods or any other embodiments of methods of the present disclosure, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. The alteration of at least one agronomic characteristic may be an increase in yield, greenness or biomass.

In any of the preceding methods or any other embodiments of methods of the present disclosure, the plant may exhibit the alteration of at least one agronomic characteristic when compared, under water limiting conditions, to a control plant not comprising said recombinant DNA construct.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

Transgenic plants comprising or derived from plant cells or native plants with increased polypeptide expression or activity of this disclosure can be further enhanced with stacked traits, e.g., a crop plant having an enhanced trait resulting from expression of DNA disclosed herein in combination with herbicide tolerance and/or pest resistance traits. For example, plants with increased ERF4a expression can be stacked with other traits of agronomic interest, such as a trait providing herbicide resistance and/or insect resistance, such as using a gene from *Bacillus thuringensis* to provide resistance against one or more of lepidopteran, coliopteran, homopteran, hemiopteran and other insects. Known genes that confer tolerance to herbicides such as e.g., auxin, HPPD, glyphosate, dicamba, glufosinate, sulfonylurea, bromoxynil and norflurazon herbicides can be stacked either as a molecular stack or a breeding stack with plants expressing the traits disclosed herein. Polynucleotide molecules encoding proteins involved in herbicide tolerance include, but are not limited to, a polynucleotide molecule encoding 5-enolpyruvylshikimate-3-phosphate synthase (EPSPS) disclosed in U.S. Pat. Nos. 39,247; 6,566,587 and for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Pat. Nos. 7,622,641; 7,462,481; 7,531,339; 7,527,955; 7,709,709; 7,714,188 and 7,666,643 also for providing glyphosate tolerance; dicamba monooxygenase disclosed in U.S. Pat. No. 7,022,896 and WO 2007/146706A2 for providing dicamba tolerance; a polynucleotide molecule encoding AAD12 disclosed in US Patent Application Publication Number 2005/731044 or WO 2007/053482A2 or encoding AAD1 disclosed in US Patent Application Publication Number 2011/0124503A1 or U.S. Pat. No. 7,838,733 for providing tolerance to auxin herbicides (2,4-D); a polynucleotide molecule encoding hydroxyphenylpyruvate dioxygenase (HPPD) for providing tolerance to HPPD inhibitors (e.g., hydroxyphenylpyruvate dioxygenase) disclosed in e.g., U.S. Pat. No. 7,935,869; US Patent Application Publication Numbers 2009/0055976 A1 and 2011/0023180 A1, each publication is herein incorporated by reference in its entirety.

Other examples of herbicide-tolerance traits that could be combined with the traits disclosed herein include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616 and 5,879,903. Plants containing an exogenous phosphinothricin acetyltransferase can exhibit improved tolerance to glufosinate herbicides, which inhibit the enzyme glutamine synthase. Other examples of herbicide-tolerance traits include those conferred by polynucleotides conferring altered protoporphyrinogen oxidase (protox) activity, as described in U.S. Pat. Nos. 6,288,306 B1; 6,282,837 B1 and 5,767,373 and International Patent Publication Number WO 2001/12825. Plants containing such polynucleotides can exhibit improved tolerance to any of a variety of herbicides which target the protox enzyme (also referred to as "protox inhibitors").

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment or *Agrobacterium*-mediated transformation. Techniques for plant transformation and regeneration have been described in International Patent Publication Number WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants may be crossed to seed-grown plants of agronomically important lines. Conversely, pollen from plants of these important lines may be used to pollinate regenerated plants. A transgenic plant of the present disclosure containing a desired polypeptide is cultivated using methods well known to one skilled in the art.

EXAMPLES

The present disclosure is further illustrated in the following Examples, in which parts and percentages are by weight and degrees are Celsius, unless otherwise stated. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Identification of Functional DRE/CRT in the TdCor410b Promoter and Confirmation of its Involvement in Response to Different Stresses The *T. durum* homolog of Wcor410 and the regulatory sequence starting 2,685 bp upstream of the translational start codon was isolated from a BAC library prepared from *Triticum durum* cv. Langdon (Grossi, et al., (1995) *Plant Sci.* 105:71-80). The cloned gene contained a single 111 bp long intron. The alignment of the deduced protein to Wcor410 homoeologs and similar proteins from rice and barley demonstrated that the gene product from *T. durum* has the highest level of protein sequence identity (difference in a single amino acid residue) to Wcor410b (FIG. 9), and was therefore designated as TdCor410b.

TaDREB3 was used to activate deletions in the TdCor410b promoter in transient expression assays with the aim of identifying functional cis-element(s). Mixtures of equal amounts of pUbi-GFP (negative control) or pUbi-TaDREB3 with the pTdCor410b-GUS plasmid(s), containing deletions in the TdCor410b promoter, were used to co-transform a cell suspension culture of *T. monnoccocum*. Deletions of the promoter were generated based on putative cis-acting elements at −1872, −945, −556, −417, −299, and −230 bp (FIG. 10). Each of these deletions, except deletion −945, decreased the number of putative DRE/CRT elements by one, thus creating the opportunity to evaluate individual elements for functionality (FIG. 1A). Cell cultures transformed with −1872, −945, −556, −417, and −299 deletions in the promoter showed similar levels of GUS expression (2.1-2.9 fold increases in activity). However, the −230 bp promoter deletion could not activate the reporter gene, indicating that the promoter was regulated by TaDREB3 through the putative DRE/CRT located between −299 and −230 bp (FIG. 1A). The element responsible for the basal level of promoter activity was evidently located on the same segment of the promoter, because the −230 bp long deletion could provide only about a quarter of the basal activity of the full-length promoter. The sequence of the DRE/CRT element recognized by TaDREB3 is TTCCGGCCGACACGCT (SEQ ID NO: 29). The GCCGAC core element is referred to as a cold responsive element that functions in *Arabidopsis* as the GGCCGACAT element. The GCCGAC core element differs from the originally identified DRE element, TACCGAC (Liu, et al., (1998) *Plant Cell* 10:1391-1406; Yamaguchi-Shinozaki and Shinozaki, (1994) *Plant Cell* 6:251-264), used for the isolation of TaDREB3 (Lopato, et al., (2006) *Plant Methods* 2:3-17), in the first base pair of the core element. However, the GCCGAC and ACCGAC elements have different protein-binding specificity, and therefore these elements are designated as CRT and DRE, respectively. It is possible that other upstream CRT(s) could become functional, at least partially, if the primary element was lost or mutated. Alternatively, other DREB/CBFs may target other DRE/CRT elements within the same promoter.

Several single by mutations introduced into the core sequence of the mapped functional CRT element on the −263 bp deletion of the TdCor410b promoter were used in transient expression assays to verify functionality of the identified cis-element (FIG. 11). Activation of GUS fused to each of the mutant fragments was compared with activity of the D7 (−263) (positive control) and D8 (−242) (negative control) deletions after co-bombardment with the pUbi-TaDREB3 construct. Each of the four tested mutations strongly decreased the activity of the −253 promoter deletion. However, substitution of the second C and last C of the core element for Ts was required for DNA-protein binding. These mutations decreased the activity of the −253 deletion to the level of the negative control (FIG. 11). The HvDhn8 promoter sequence available from the databases (Acc. AF043093) was compared with that of the TdCor410b. Co-bombardment of pHvDhn8-GUS with pUbi-TaDREB3 constructs demonstrated a 6-fold activation of the promoter with TaDREB3 compared to the activation of the negative control (FIG. 12B).

Analysis of transgenic barley plants overexpressing TaDREB3 under the 2,685 bp and 275 bp fragments of the TdCor410b promoter revealed the presence of basal activity and inducibility by cold, drought and wounding for both promoter fragments. This analysis confirmed that activation of the TdCor410b promoter in the absence of stress and under different stresses occurred through the same CRT element that was proximal to the TATA box. The strength of activation of the 275 bp long promoter fragment in transgenic plants seems to be lower than that of the full-length promoter, an observation that remains to be investigated more conclusively in stable transgenic plants (FIG. 1B).

Example 2

Isolation of TFs Using a CRT Element as Bait and Confirmation of Involvement of TFs in the TdCor410b Promoter Activation The core sequence GCCGAC repeated five times (CRT1) or a fragment of the TdCor410b promoter containing the GCCGAC core sequence with five adjacent base pairs, TTCCGGCCGACACGCT (SEQ ID NO: 29), repeated three times (CRT2), were used to screen three separate prey libraries. These included 1) WENDL, a library prepared from wheat un-stressed endosperm; 2) WHSL, a library prepared from drought/heat-stressed wheat flag leaf and spikes and 3) BCG, a library prepared from cold/frost-stressed barley floral tissues and flag leaf. Five different AP2-domain containing TFs were isolated with the core element from WENDL, but only one of them was a DREB factor (TaDREB2). The remaining four TFs encoded TaERF5a, TaERF4a, TaERF5b and TaERF6, all belonging to the subfamily of the ethylene-responsive element (GCC-box) binding factors (EREBFs or ERFs). In addition to these six TFs, TaERF4a and TaERF4b were isolated using the CRT1 and CRT2 elements from the WHSL library and HvERF4 from the BCG library. Only two TFs, TaERF4a and HvERF4b were isolated using a CRT2 promoter fragment as bait. One of the isolated TFs, TaERF5a, had been isolated with the GCC-box as bait from the WHSL library. A TaERF5b, had been isolated with the GCC-box as bait from wheat roots, subjected to drought in soil. However, no TaERF4-like TFs have been isolated with the GCC-box from any of five diverse cDNA libraries (our unpublished data). The unrooted phylogenetic tree (FIG. 2A) indicates an evolutionary relationship of isolated wheat TFs (marked in bold characters) with respect to their known plant homologues.

TaERF4a, TaERF5a and TaERF6 were tested in a yeast two-hybrid assay for the presence of activation domains and their ability to activate a yeast reporter gene. All three proteins behaved as activators (FIG. 2C). Each of these proteins, when fused to the binding domain of the yeast GAL4 TF, could activate downstream reporter genes and consequently support yeast growth on selective media (FIG. 2).

Full-length coding regions of the representatives from each subfamily of ERF genes, i.e., TaERF4a, TaERF5a and TdERF6, were cloned into the pUbi vector and examined for their ability to activate the TdCor410b promoter in a transient expression assay. Here it was found that TaERF4a activated the full-length promoter of the TdCor410b gene and this activation was about 6-7 fold higher than the basal level of promoter activity (FIG. 2D). However, the mutations that were introduced into a predicted ERF-associated amphiphilic repression (EAR) motif of TaERF4a (FIG. 14B), strongly decreased promoter activation. These mutations consisted of substitutions of four amino acid residues in the EAR motif (see FIG. 14B) for the alanine residue. TaERF5a had no influence on the TdCor410b promoter activity, which remained at the lower level of basal activity, while TdERF6 completely inhibited the basal activity of the TdCor410b promoter in several independent experiments (FIG. 2D).

Altogether seven different AP2-domain-containing TFs were isolated but only one of them was DREB TF (TaDREB2). The remaining six TFs encoded TaERF4a, TaERF4b, HvERF4, TaERF5a, TaERF5b, and TaERF6, all belonging to the subfamily of the ethylene-responsive element (GCC-box) binding TFs (EREBPs or ERFs). Only two TFs, TaERF4a and HvERF4b, were isolated using a CRT2 as bait. TaERF5a, TaERF5b, and TaERF6 had been isolated previously with the GCC-box as bait from the same cDNA libraries. However, no TaERF4-like TFs have been isolated with the GCC-box from any of the five screened cDNA libraries.

Example 3

Phylogenetic Analysis of TFs Isolated in Y1H Screens

The unrooted phylogenetic tree of 32 entries of the selected TF proteins containing the AP2 domains from mono- and dicotyledonous species was constructed to establish a phylogenetic relationship among the individual proteins (FIG. 2A). The phylogeny between the AP2 domain of AtERF1 from *Arabidopsis* (in bold characters and underlined) was established to use as a template for molecular modeling of the AP2 domains of TaERF4a, TaERF5a and TaDREB3. The phylogeny of three major branches indicated that the full-length sequence of the selected mono- and dicotyledonous ERF and DREB proteins clustered into four independent branches, highlighting their functional roles (FIG. 2A). This clustering is in agreement with their DNA binding selectivity as demonstrated by Y1H assay (FIG. 2B). The analysis of selectivity of binding of cis-elements confirmed that all tested TFs from wheat could bind the GCCGAC core element. No differences in binding of any of the tested factors to the CRT1 (GCCGAC) and CRT2 (TTCCGGCCGACACGCT (SEQ ID NO: 29); the bold type indicates the GCCGAC core element) sequences in the Y1H assay were observed. Thus, the core element itself is likely sufficient to confer specificity of binding, and influence of adjacent sequences is considered to be minimal, if any. The analysis also established that the DREB factors could only bind the DRE (ACCGAC) motif, but could not bind the GCC-box (GCCGCC). TaERF5a and TaERF6 could interact with the GCC-box, but could not bind DRE. Surprisingly, TaERF4a could bind neither the GCC-box nor DRE and only possessed specific binding to CRT (FIG. 2B).

Example 4

Domain Organization and Structural Alignments of AtERF1 (1gcc:A) with AP2 Domains of TaERF4a, TaERF5a and TaDREB3

The AP2 domain (or the GCG-box binding domain) of the AtERF1 from *Arabidopsis*, (PDB accession 1gcc:A), was used for comparative structural analysis and modeling of the ERF and DREB transcription factors isolated in our studies, due to the presence of this domain in both classes of TFs. Analysis of entries available through the GenBank database with ProDom (Corpet, et al., (1998) *Nucleic Acids Res.* 26:323-326) demonstrated that the DNA-binding domain of approximately 62 residues was present in the TaERF4a, TaERF5a and TaDREB3 TFs, although their precise dispositions within the full-length sequences differed. Structural alignment of 32 sequences provided information about the conservation of the AP2 domains at the amino acid levels within the selected TFs. Analysis indicated that the sequences could be divided into two major groups, based on conservation of a Pro residue following Arg152 in 1gcc:A; Arg152 makes close interactions with a coding DNA strand (Allen, et al., (1998) *EMBO J.* 17:5484-5496). While this Pro residue was highly conserved in the ERF sequences, a highly variable residue that never involved Pro was present in the corresponding position in the DREB sequences (see FIG. 4A). Further examination of the alignment revealed that the ERF sequences could be sub-divided into two additional subgroups. The first subgroup comprised the members of the subfamily of TaERF4a-like proteins, which contained Pro42 in the TPI motif in position 42, whereas all other examined ERFs contained Arg in the corresponding position (the regions highlighted in cyan and grey in FIG. 4A). This analysis indicated the significance of Arg42 in a recognition selectivity of the GCC-box by ERFs. The observation that Pro42 found in the TaERF4a-like proteins occurred exclusively in monocotyledonous species was surprising, as confirmed by analysis of 501 sequences through ConSurf (Ashkenazy, et al., (2010) *Nucleic Acids Res.* 38:W529-533).

Example 5

Molecular Modeling of the AP2 Domains of TaERF4a, TaERF5a and TaDREB3 to Reveal Selectivity of Binding of Cis-Elements The suitable structural template for all TFs was identified to be the AP2 domain (or the GCC-box binding domain) of ERF, designated here as 1gcc:A from *A. thaliana* (AtERF1). The suitability of the 1 gcc:A template was confirmed through the searches by PsiPred (McGuffin, et al., (2000) *Bioinformatics* 16:404-405), SAM-T08 (Karplus, (2009) *Nucleic Acids Res.* 37:W492-W497), STRIDE (Frishman and Argos, (1995) *Proteins* 23:566-579), DSSP (Kabsch and Sander, (1983) *Febs Lett.* 155:179-182), PROMALS3D (Pei, et al., (2008) *Nucleic Acids Res.* 36:2295-2300) and Robetta (Kim, et al., (2004) *Nucleic Acids Res.* 32:W526-W531). The sequence of 1gcc:A (Lascombe, et al., (2008) *Protein Sci.* 17:1522-1530) was aligned with the TaERF4a, TaERF5a and TaDREB3 sequences, whereby care was taken that during alignments the positions of secondary structures of proteins remained undisturbed. The positional sequence identity and similarity between AtERF1 (1gcc:A) and TaERF4a, TaERF5a and TaDREB3, determined by an Epprofile algorithm (Smith and Waterman, (1981) *J. Mol. Biol.* 147:195-197), were 40% and 55%, 31% and 50%, and 38% and 53%, respectively. The sequence identity between 1gcc:A and TaERF5a was close to the so-called 'twilight zone' and this fact emphasized a high complexity of modeling (Sali, et al., (2004) *Proteins* 23:318-326). Pairwise alignments between the template and the target sequences, TaERF4a, TaERF5a and TaDREB3, indicated that there was one single-residue deletion (corresponding to Asn167 in1gcc:A) in all three alignments.

Analyses through PROCHECK (Corpet, et al., (1998) *Nucleic Acids Res* 26:323-326) and Prosa2003 (Sippl, (1993) *Proteins-Struct Funct. Genet* 17:355-362) indicated that the 3D models generated by comparative modeling were reliable and that the stereochemistry of protein structures was satisfactory. As the sequence identities between the TaERF4a, TaERF5a and TaDREB3 AP2 domains were within similar ranges, similar protein folds as well as a high degree of conservation of residues in all 3D models (FIG. 3A) were observed. It was evident from FIG. 3A that the three TFs contained an α-helix and a three-stranded antiparallel β-sheet. This type of architecture is characteristic of a global 'alpha and beta protein' class, which contains entries that bind DNA, according to SCOP protein classification (Pasquato, et al., (2005) *Supramol. Chem.* 17:163-171). Calculations of electrostatic potentials revealed the presence of a highly positively-charged depression within the structure of AP2 domains, where the double stranded cis-element is expected to bind (FIG. 3A). As the molecular models of the AP2 domains of TaERF4a, TaERF5a and TaDREB3 were generated in the presence of their respective cis-elements, how the individual DNA hexamers bind within the AP2 grooves and what structural determinants precisely underline the recognition selectivity of the respective cis-elements (FIG. 3) were envisioned. Here, modelling revealed that the coding strand of DNA molecules were bound through a series of highly conserved residues exposed on the two longer anti-parallel β-sheets and that conserved Arg and Trp residues mediated the contacts between cis-elements and the AP2 domains in all instances (FIG. 3). It was of note that, from all residues within the AP2 domains, the conservation of two Pro residues in TaERF4a, TaERF5a and HvERF4 was most observable, as well as the presence of variable residues in DREBs at the end of a short β-sheet and in the middle of the β-sheet (see FIG. 4A). These comparisons indicated that the β-sheets in the ERF or DREB AP2 domains could flex to a higher or lesser degree, due to the presence or absence of Pro, and that this β-sheet flexibility could affect the overall geometry of the AP2 domains, or more or less favourably affect orientation of individual cis-elements, thus leading to their tighter or weaker binding to cis-elements. The comparisons of TaDREB3 in complex with GCCGAC and ACCGAC indicated that Arg48, which is positioned next to Gly49 (FIG. 3B), had significant flexibility and could reach out and mediate close contacts with both cis-elements. On the contrary, flexibility of Arg131 in TaERF5a that binds GCCGCC or GCCGAC, could be severely restricted due to the presence of neighboring Pro132. It was investigated as to why the GCCGCC cis-element is only recognized by the AP2 domain of TaERF5a but not by TaDREB3. The modeling studies indicate that the recognition selectivity of TaDREB3 could be decided by several structural features. Firstly, the overall length of the sequence spanning Gly49 and Arg66 (16 residues) might be of importance, and secondly, the environment around Arg48 and Arg66 might be critical, thus preventing binding of the GCC-box by TaDREB3. On the other hand, the environment around Arg131 in the AP2 of TaERF5a (iso-positional to Arg48 in AP2 of TaDREB3), and a shorter β-sheet region comprising 15 residues between Pro132 and Arg148 (iso-positional to the Gly49-Arg66 region in TaDREB3's AP2), would allow binding of both cis-elements GCCGCC and GCCGAC. However, the length of a β-sheet segment that forms the DNA binding region in TaERFs might not be due to only structural requirements for binding of the GCC-box. For example, in the AP2 domain of TaERF4a, although the β-sheet contains a shorter region, comprising 15 residues between Pro26 and Pro42, the presence of the two relatively closely positioned Pro residues could restrict flexibility of the β-sheet, thus prevent binding of the GCC-box by TaDREB3 (FIG. 3B). Conversely, binding of GCCGAC by the AP2 domain of TaERF4a could be favourable, because an amino group of the purine ring of adenine could mediate productive interactions with AP2.

Example 6

Site-Directed Mutagenesis of Amino Acid Residues to Establish Recognition Selectivity of the AP2 Domain of TaERF4a with the GCCGCC Cis-Element A molecular model of the AP2 domain of TaERF4a, and its comparison with the AP2 models of TaERF5a and TaDREB3 in complex with a variety of cis-elements (FIG. 3) allowed generation of variant proteins of the AP2 domain of TaERF4a with potentially modified selectivity for binding the GCCGCC element, or the GCC box (FIG. 3B). Through site-directed mutagenesis, two mutants, each affecting one of two Pro residues were generated, namely, the Pro26Arg mutant (designated as TaERF4a mut1; FIG. 4B) or the Pro42Arg mutant (designated as TaERF4a mut 2; FIG. 4B). The TaERF4a mutant 1+2 (Pro26Arg+Pro42Arg) thus represented a double variant in both Pro residues (FIG. 4B). The latter mutant was designed to modify flexibilities of cognate β-sheets through the side-chain residue variations to mimic properties of respective β-sheets and disposition of residues within TaDREB3.

A complete restoration of binding to the GCC-box by the AP2 domain of TaERF4a was obtained by replacing Pro42 with Arg42 (TaERF4a mut 2) (FIG. 4B). The yeast GCC-box bait strain grew on the selective medium when TaERF4a mut 2 was expressed, while this was not the case for TaERF4a mut 1 (FIG. 4B). The ability of the double mutant, TaERF4a mutant 1+2, to grow on the selective medium was clearly due to the Pro42Arg mutation (FIG. 4B). The expression of wild type TaERF4a could not support growth of the yeast GCC-box bait strain under the same selective conditions (FIG. 4B).

These data were further confirmed in planta using transient expression assay in wheat cell culture. The artificial promoter, containing three repeats of the GCC-box was weakly activated by wild type TaERF4a. Regulation of the activity of the TdCor410b promoter and of the artificial promoter with substitution of the CRT element for tandem of three GCC-boxes was tested with representatives of each isolated ERF subfamily, and variants of TaERF4a with mutations in the AP2 domain. TFs were tested in a transient expression assay in a wheat cell culture. Either pTdCor410b-GUS or 3xGCCbox-GUS constructs were co-bombarded with pUbi-GFP (GFP), pUbi-TaERF4a (TaERF4a), pUbi-TaERF4a mutated in Pro26 (TaERF4a m1), pUbi-TaERF4a mutated in Pro42 (TaERF4a m2), pUbi-TaERF4a mutated in Pro26 and Pro42 (TaERF4a m1+2), pUbi-TaERF6 (TaERF6) and pUbi-TaERF5a (TaERF5a).

This promoter was not activated by TaERF4a mut 1, but it was strongly activated by TaERF4a mut 2. The functionality of the artificial promoter was confirmed by activation of this promoter with TaERF5a and TaERF6 TFs. These findings demonstrated the activation behaviour of the last two ERF TFs in planta and confirmed the results that were earlier obtained in yeast (FIG. 2C). Surprisingly, the wild type TdCor410b promoter was also strongly activated by TaERF4a mutant 2, but was not activated by mutant 1 and was only weakly activated by mutant 1+2. In contrast to TaERF4a mutant 2, both TaERF5a and TaERF6 TFs were not able to activate the wild type TdCor410b promoter in transient expression assay.

Example 7

Expression Patterns of TaCor410b and ERFs in Different Tissues and Under Different Stress Conditions Spatial expression patterns of TaCor410b and five ERF genes, isolated through a Y1H screen were analysed using Q-PCR. In the absence of stress, expression of TaCor410b was detected in all tissues analysed, with strongest expression in anthers and pistils shortly before fertilization. TaDREB3, which weakly activated TaCor410b in transgenic wheat plants and the TdCor410b promoter in transient assays, was also expressed in reproductive tissues. Although strongest expression of TaDREB3 was detected in pistil, with low expression in anthers, it was concluded that TaDREB3 can regulate expression of Wcor410b.

TaERF4b, the closest homologue of TaERF4a, and possibly a homoeologue of TaERF4a, was about 100-fold less abundant than TaERF4a and was expressed mostly in leaves, mature grain and floral tissues. The expression pattern of TaERF4b showed very little correlation with the expression pattern of TaERF4a and TaCor410b, but closely resembled that of TaERF6 (FIG. 5). The close homologues, possibly homoeologues, TaERF5a and TaERF5b, had very similar expression patterns, although expression of TaERF5b was about 20-fold higher than that of TaERF5a. Characteristic features of these two genes are the relatively low levels of expression in anthers and in most other tested tissues and very high levels of expression in bracts, pistil and grain (FIG. 5).

Cold stress, imposed as a constant treatment at 4° C., strongly induced TaCor410b by about eleven-fold (FIG. 6A). Expression of the gene started to increase within several hours, reached maximum levels after 24 hours of plant exposure to cold and nearly returned to control levels at the end of the second day (FIG. 6A). The wheat and barley ERF genes (FIGS. 6A and 13), as well as TaDREB3 and TaDREB2 (Morran, et al., (2011) *Plant Biotechnol. J.* 9:230-249) showed a weak to mild induction by cold during the first four hours. The expression of ERFs and DREBs by cold treatment always preceded induction of the downstream TaCor410b gene (FIG. 6A).

Under stringent drought conditions, where leaf wilting was observable and volumetric water content in soil was 53%, TaCor410b was up-regulated 4-fold (FIG. 6B). Its expression returned to a normal level after re-watering and two weeks of recovery. Under similar drought stress, induction of expression was observed for TaERF4a, TaERF4b and TaERF6. Re-watering followed by two weeks of recovery led to gene-expression levels comparable to those under well-watered conditions. On the contrary, expression of TaERF5a under stringent drought conditions decreased relative to well-watered conditions, while expression of TaERF5b remained nearly unchanged under water deficit. Both genes demonstrated several fold increases in their expression upon re-watering and a two-week plant recovery.

Wounding of leaves of a three-week-old seedling produced 1.5 fold activation of TaCor410b after one hour of stress. After 24 hours, the levels of expression were 12-fold higher than those in the control leaf (FIG. 7A). The expression patterns of all tested ERFs, except TaERF6, were very similar with strong reduction in expression after one hour, and partial or complete restoration to normal expression levels after 24 hours. TaERF6 and TdERF6 were quickly and strongly induced to about 20-30 fold by wounding within the first hour and expression returned to control levels by three hours after wounding (FIG. 7). TdERF6 induction preceded that of TdCor410b and this temporal pattern correlated well throughout treatments by wounding (FIGS. 7B and 7C).

We claim:

1. A plant comprising in its genome a polynucleotide encoding a transcription factor designated ERF4 comprising an amino acid sequence that has at least 95% sequence identity to SEQ ID NO:1 and comprising an EAR motif having the amino acid sequence of KTPIWLGTFD (SEQ ID NO:20), wherein the polynucleotide is operably linked to a heterologous regulatory element, and wherein said plant has increased drought tolerance when compared to a plant lacking said polynucleotide.

2. The plant of claim 1, wherein the polynucleotide encodes the polypeptide comprising SEQ ID NO:1 or a polypeptide having at least 98% sequence identity to SEQ ID NO:1.

3. The plant of claim 1 selected from the group consisting of maize, barley, wheat, soybean, cotton, *sorghum* and *brassica*.

4. A transgenic plant comprising a polynucleotide encoding a polypeptide having at least 98% sequence identity to SEQ ID NO:1, wherein the polynucleotide is operably linked to a heterologous regulatory element, and wherein said plant has increased drought tolerance when compared to a plant lacking said polynucleotide.

* * * * *